United States Patent
Park et al.

(10) Patent No.: US 9,278,996 B2
(45) Date of Patent: Mar. 8, 2016

(54) DOLASTATIN-10 DERIVATIVE, METHOD OF PRODUCING THE SAME AND ANTICANCER DRUG COMPOSITION CONTAINING THE SAME

(71) Applicant: CELLTRION, INC., Incheon (KR)

(72) Inventors: Young Jun Park, Gyeonggi-do (KR); Jin-kyo Jeong, Seoul (KR); Young Mi Choi, Gyeonggi-do (KR); Min Seob Lee, Incheon (KR); Joon hun Choi, Gyeonggi-do (KR); Eun Joo Cho, Gyeonggi-do (KR); Hyunnam Song, Gyeonggi-do (KR); Sung Jun Park, Gyeonggi-do (KR); Jong-hyoup Lee, Gyeonggi-do (KR); Seung Suh Hong, Seoul (KR)

(73) Assignee: CELLTRION, INC., Incheon (KR)

( * ) Notice: Subject to any disclaimer, the term of this patent is extended or adjusted under 35 U.S.C. 154(b) by 0 days.

(21) Appl. No.: 14/430,059

(22) PCT Filed: Sep. 16, 2013

(86) PCT No.: PCT/KR2013/008371
§ 371 (c)(1),
(2) Date: Mar. 20, 2015

(87) PCT Pub. No.: WO2014/046441
PCT Pub. Date: Mar. 27, 2014

(65) Prior Publication Data
US 2015/0225455 A1    Aug. 13, 2015

(30) Foreign Application Priority Data
Sep. 20, 2012   (KR) .................. 10-2012-0104710

(51) Int. Cl.
| | | |
|---|---|---|
| A61K 38/00 | (2006.01) |
| A61P 35/00 | (2006.01) |
| C07K 7/06 | (2006.01) |
| C07D 207/12 | (2006.01) |
| C07D 401/12 | (2006.01) |
| C07D 409/12 | (2006.01) |
| C07K 5/062 | (2006.01) |
| A61K 31/40 | (2006.01) |
| C07K 5/02 | (2006.01) |

(52) U.S. Cl.
CPC . *C07K 7/06* (2013.01); *A61K 31/40* (2013.01); *C07D 207/12* (2013.01); *C07D 401/12* (2013.01); *C07D 409/12* (2013.01); *C07K 5/0205* (2013.01); *C07K 5/06052* (2013.01); *A61K 38/00* (2013.01)

(58) Field of Classification Search
CPC ......... A61K 38/00; A61K 31/40; C07K 1/006
See application file for complete search history.

(56) References Cited

U.S. PATENT DOCUMENTS

| | | |
|---|---|---|
| 5,599,902 A | 2/1997 | Pettit et al. |
| 6,004,934 A | 12/1999 | Sakakibara et al. |
| 6,569,834 B1 | 5/2003 | Pettit et al. |

FOREIGN PATENT DOCUMENTS

| | | |
|---|---|---|
| EP | 2 260 858 | 5/2004 |
| KR | 10-2014-0038324 | 3/2014 |
| WO | WO 03/008378 | 1/2003 |

OTHER PUBLICATIONS

Pettit et al., Anti-Cancer Drug Design, 1998, 13, 243-277, published on 1998.*
Shnyder et al. "Auristatin PYE, a novel synthetic derivative of dolastatin 10, is highly effective in human colon tumour models," International Journal of Oncology, pp. 353-360, Jan. 2007.
Yamamoto et al., Phase I study of TZT-1027, a novel synthetic dolastatin 10 derivative and inhibitor of tubulin polymerization, given weekly to advanced solid tumor patients for 3 weeks, Cancer Science, pp. 316-321, Feb. 2009.
Pettit et al., The Isolation and Stucture of a Remarkable Marine Animal Antineoplastic Constituent: Dolastatin 10, J. Am. Chem Soc, pp. 8663-6885, Apr. 1987.
Jaspars, Testing the Water, Chemistry and Industry, Jan. 1999.
Poncet, "The Dolastatins, A Family of Promising Antineoplastic Agents", Current Pharmaceutical Design, pp. 139-162, 1999.
Madden et al., "Novel Marine-derived Anticancer Agents: A Phase I Clinical, Pharmacological, and Pharmacodynamic Study of Dolastain 10 (NSC 376128) in Patients with Advanced Solid Tumors", Clinical Cancer Research, pp. 1293-1301, Apr. 2000.
Auristatin PE., "TZT-1027 (Antineoplastic)," Drugs of the Future, pp. 404-409, 1999.

* cited by examiner

*Primary Examiner* — James H Alstrum Acevedo
*Assistant Examiner* — Kaipeen Yang
(74) *Attorney, Agent, or Firm* — Baker & Hostetler LLP

(57) ABSTRACT

The present invention provides a dolastatin-10 derivative having excellent anticancer activity, a method of producing the same and anticancer drug composition containing the same as an active ingredient.

14 Claims, No Drawings

DOLASTATIN-10 DERIVATIVE, METHOD OF PRODUCING THE SAME AND ANTICANCER DRUG COMPOSITION CONTAINING THE SAME

CROSS-REFERENCE TO RELATED APPLICATIONS

This application is the National Stage of International Application No. PCT/KR2013/008371, filed Sep. 16, 2013, which claims the benefit of and priority to Korean application No. 10-2012-0104710, filed Sep. 20, 2012, the entireties of which applications are incorporated herein by reference for any and all purposes.

TECHNICAL FIELD

The present invention relates to a dolastatin-10 derivative with excellent anticancer activity, a method for preparing the same, and an anticancer drug composition containing the same as an active ingredient.

BACKGROUND ART

Dolastatin-10 was isolated from the Indian Ocean sea hare *Dolabella auricularia* in 1987 and identified to have the following chemical structure [J. Am. Chem. Soc., 1987, 109, 6883-6885]. Dolastatin-10 exhibits physiological activity as an antimicrotuble agent similar to taxane and vinca alkaloid, but is a structurally different peptide [Chem. Ind., 1999, 51-55; Curr. Pharm. Des., 1999, 5, 139-162].

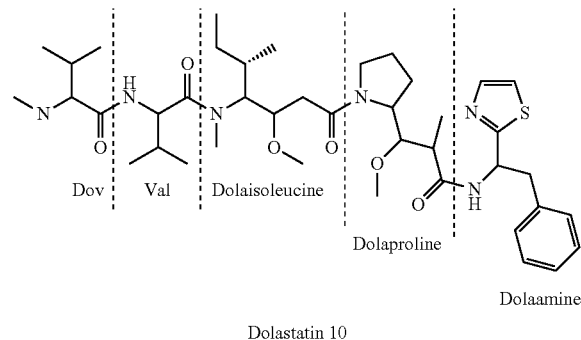 [SMILES: CC[C@H](C)C(C(CC(=O)N1CCCC1C(OC)C(C)C(=O)NC(Cc1ccccc1)c1nccs1)OC)N(C)C(=O)C(NC(=O)C(NC)C(C)C)C(C)C]

Dolastatin 10

Different in structure from taxane and vinca alkaloid as well as proven to have inhibitory activity against various human tumors in in vitro and animal model experiments in pre-clinical trials, dolastatin-10 was expected to not exhibit the side effects found in taxane and vinca alkaloid, such as myelotoxicity. In spite of the structural difference, however, dolastatin-10 was found to have myelotoxicity, neurotoxicity, and other side effects, such as taxane and vinca alkaloid, in clinical studies [Clin. Cancer Res., 2000, 6, 1293-1301; Drugs of the Future, 1999, 24(4), 404-409].

A variety of dolastatin-10 derivatives were synthesized, with derivatization conducted on the five moieties Dov (dolavaline), Val (valine), dolaisoleucine, dolaproline, and dolaamine. Of them, the dolaproline and dolaamine moieties have been intensively studied while dolastatin-10 derivatives were disclosed in WO 2003/008378 where the methoxy of the dolaproline moiety was substituted with thiomethoxy and in U.S. Pat. No. 5,599,902 where the dolaamine moiety was modified. Meanwhile, EP No. 260 858 discloses a derivative in which the dimethylvaline of the Dov moiety is substituted with monomethylvaline.

DISCLOSURE

Technical Problem

Leading to the present invention, intensive and thorough research into a dolastatin-10 derivative with more potent cytotoxicity against cancer cells resulted in the finding that the dolastatin-10 derivative, represented by the following Chemical Formula I, in which the pyrrolidine ring of the dolaproline moiety is modified, exhibits excellent anticancer activity.

It is therefore an object of the present invention to provide a dolastatin-10 derivative of Chemical Formula I with excellent anticancer activity, or a pharmaceutically acceptable salt thereof.

It is another object of the present invention to provide a method of producing a dolastatin-10 derivative of Chemical Formula I or a pharmaceutically acceptable salt thereof.

It is a further object of the present invention to provide an anticancer drug composition containing a dolastatin-10 derivative of Chemical Formula I, or a pharmaceutically acceptable salt thereof.

Technical Solution

In accordance with an aspect thereof, the present invention addresses a dolastatin-10 derivative of Chemical Formula I, or a pharmaceutically acceptable salt thereof:

[Chemical Formula I]

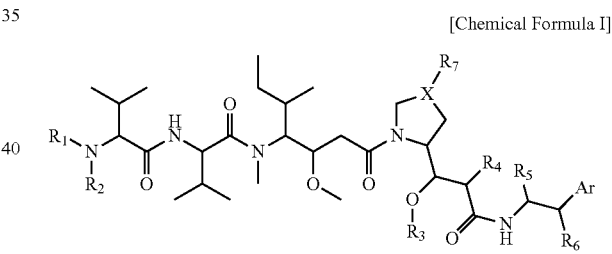

wherein, $R_1$, $R_2$, $R_3$, $R_4$, and $R_5$ are each independently hydrogen or $C_1$-$C_4$ alkyl, $R_6$ is hydrogen, hydroxy, $C_1$-$C_4$ alkoxy, amino, oxo(=O), or hydroxyimino(=N—OH), Ar is aryl, X is a carbon, oxygen or sulfur atom, and $R_7$ is hydroxy, amino, $C_1$-$C_4$ alkoxy, $C_1$-$C_4$ alkylamino, or oxo (=O) when X is a carbon atom, and is absent when X is an oxygen or sulfur atom.

The term "$C_1$-$C_4$ alkyl," as used herein, is intended to encompass straight or branched hydrocarbons of 1 to 4 carbon atoms, including, but is not to limited to, methyl, ethyl, n-propyl, i-propyl, n-butyl, i-butyl, and t-butyl.

As used herein, the term "aryl" is intended to encompass all of aromatic groups, heteroaromatic groups, and partially reduced derivatives thereof. The term "aromatic groups" refers 5 to 15-membered single or fused rings, preferably 6, 10 or 14-membered single or fused rings, and the term "heteroaromatic groups" refers to aromatics having at least one heteroatom such as oxygen, sulfur or nitrogen. Representative examples of aryl include phenyl, naphthyl, pyridinyl, furanyl, thiophenyl, indolyl, quinolinyl, imidazolinyl, oxazolyl, thiazolyl, and tetrahydronaphthyl, but are not limited thereto.

The term "$C_1$-$C_4$ alkoxy," as used herein, is intended to encompass straight or branched alkoxy of 1 to 4 carbon atoms, and includes, but is not limited to, methoxy, ethoxy, and n-propanoxy.

The term "$C_1$-$C_4$ alkylamino," as used herein, refers to an amino group with a substituent of $C_1$-$C_4$ alkyl, and includes, but is not limited to, methylamino, ethylamino, and n-propylamino.

In the $C_1$-$C_4$ alkyl, the aryl, the $C_1$-$C_4$ alkoxy, and the $C_1$-$C_4$ alkylamino group, at least one hydrogen may be substituted by $C_1$-$C_4$ alkyl, $C_2$-$C_4$ alkenyl, $C_2$-$C_4$ alkynyl, $C_3$-$C_{10}$ cycloalkyl, $C_1$-$C_4$ haloalkyl, $C_1$-$C_4$ alkoxy, $C_1$-$C_4$ thioalkoxy, aryl, acyl, hydroxy, thio, halogen, amino, alkoxycarbonyl, carboxy, carbamoyl, cyano, or nitro.

In a preferred embodiment of the dolastatin-10 derivative according to the present invention $R_1$, $R_3$ and $R_4$ are each $C_1$-$C_4$ alkyl, $R_2$ and $R_5$ are each independently hydrogen or $C_1$-$C_4$ alkyl, $R_6$ is hydrogen, hydroxy, $C_1$-$C_4$ alkoxy, amino, oxo(=O) or hydroxyimino(=N—OH), Ar is phenyl unsubstituted or substituted with at least one selected from the group consisting of $C_1$-$C_4$ alkyl, $C_1$-$C_4$ alkoxy, and halogen, X is a carbon atom, and $R_7$ is hydroxy, amino, $C_1$-$C_4$ alkoxy or $C_1$-$C_4$ alkylamino.

In a more preferred embodiment of the dolastatin-10 derivative according to the present invention, $R_1$, $R_3$ and $R_4$ are each methyl, $R_2$ and $R_5$ are each independently hydrogen or methyl, $R_6$ is hydrogen, hydroxy, methoxy, amino, oxo (=O) or hydroxyimino (=N—OH), Ar is phenyl unsubstituted or substituted with at least one selected from the group consisting of methyl, methoxy and halogen, X is a carbon atom, and $R_7$ is hydroxy, amino, methoxy, or N-methylamino All stereoisomers of the dolastatin-10 derivative, including the compound of the following Chemical Formula Ia, fall within the scope of the present invention.

[Chemical Formula Ia]

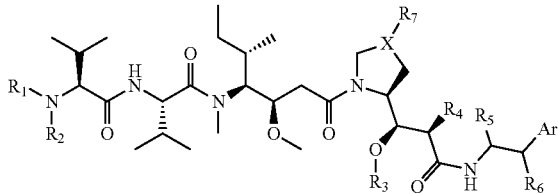

wherein, $R_1$, $R_2$, $R_3$, $R_4$, $R_5$, $R_6$, Ar, X, and $R_7$ are as defined in Chemical Formula I, respectively.

In Chemical Formula Ia, $R_5$, $R_6$, and $R_7$ are each independently in an (R)-form, in an (S)-form or in a racemic mixture.

As used herein, the term "pharmaceutically acceptable salt" is intended to encompass non-toxic salts whether inorganic or organic, and includes, but is not limited to, for example, hydrochloride, sulfate, nitrate, phosphate, acetate, benzenesulfate, citrate, etc.

Concrete examples of the dolastatin-10 derivative according to the present invention include:

(S)—N-((3R,4S,5S)-1-((2R,4R)-2-((1R,2R)-3-((2,6-difluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-1);

(S)—N-((3R,4S,5S)-1-((2R,4R)-2-((1R,2R)-3-(3-fluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-2);

(S)—N-((3R,4S,5S)-1-((2R,4R)-2-((1R,2R)-3-(4-fluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-3);

(S)—N-((3R,4S,5S)-1-((2R,4R)-2-((1R,2R)-3-(2,4-dichloro-5-fluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-4);

(2S)—N-((3R,4S)-3-methoxy-1-((2R,4R)-4-methoxy-2-((1R,2R)-1-methoxy-3-((2-(4-methoxyphenyl)-2-oxoethyl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-5);

(2S)—N-((3R,4S)-3-methoxy-1-((2R,4R)-4-methoxy-2-((1R,2R)-1-methoxy-2-methyl-3-oxo-3-(((R)-1-oxo-1-phenylpropan-2-yl)amino)propyl)pyrrolidin-1-yl)-5-methyl-1-oxoheptan-4-yl)-N,3-dimethyl-2-((S)-3-methyl-2-(methylamino)butaneamido)butanamide (I-6);

(2S)—N-((3R,4S)-3-methoxy-1-((2S,4R)-4-methoxy-2-((1R,2R)-1-methoxy-2-methyl-3-oxo-3-(((S)-1-oxo-1-phenylpropan-2-yl)amino)propyl)pyrrolidin-1-yl)-5-methyl-1-oxoheptan-4-yl)-N,3-dimethyl-2-((S)-3-methyl-2-(methylamino)butaneamido)butanamide (I-7);

(S)-2-((S)-2-(dimethylamino)-3-methylbutaneamido)-N-((3R,4S,5S)-1-((2R,4R)-4-hydroxy-2-((1R,2R)-1-methoxy-2-methyl-3-oxo-3-(phenethylamino)propyl)pyrrolidin-1-yl)-3-methoxy-5-methyl-1-oxoheptan-4-yl)-N,3-dimethylbutanamide (I-8);

(S)-2-((S)-2-(dimethylamino)-3-methylbutaneamido)-N-((3R,4S,5 S)-3-methoxy-1-((R)-2-((1R,2R)-1-methoxy-2-methyl-3-oxo-3-(phenethylamino)propyl)-4-oxopyrrolidin-1-yl)-5-methyl-1-oxoheptan-4-yl)-N,3-dimethylbutanamide (I-9);

(S)-2-((S)-2-(dimethylamino)-3-methylbutaneamido)-N-((3R,4S,5 S)-3-methoxy-1-((2R,4S)-4-methoxy-2-((1R,2R)-1-methoxy-2-methyl-3-oxo-3-(phenethylamino)propyl)pyrrolidin-1-yl)-5-methyl-1-oxoheptan-4-yl)-N,3-dimethylbutanamide (I-10);

(S)—N-((3R,4S,5S)-1-((2R,4R)-2-((1R,2R)-3-(((R)-1-(4-fluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-11);

(S)—N-((3R,4S,5S)-1-((2R,4R)-2-((1R,2R)-3-(((S)-1-(4-fluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-12);

(S)—N-((3R,4S,5S)-3-methoxy-1-((2R,4R)-4-methoxy-2-((1R,2R)-1-methoxy-3-(((R)-1-(2-methoxyphenyl)-1-oxopropan-2-yl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-13);

(S)—N-((3R,4S,5S)-3-methoxy-1-((2R,4R)-4-methoxy-2-((1R,2R)-1-methoxy-3-(((R)-1-(3-methoxyphenyl)-1-oxopropan-2-yl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-14);

(S)—N-((3R,4S,5S)-3-methoxy-1-((2R,4R)-4-methoxy-2-((1R,2R)-1-methoxy-3-(((R)-1-(4-methoxyphenyl)-1-oxopropan-2-yl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-15);

(S)—N-((3R,4S,5S)-1-((2R,4R)-2-((1R,2R)-3-(((S)-1-(3,5-difluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-16);

(S)—N-((3R,4S,5S)-1-((2R,4R)-2-((1R,2R)-3-(((S)-1-(2,6-difluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-17);

(S)—N-((3R,4S,5S)-1-((2R,4R)-2-((1R,2R)-3-(((R)-1-(2,6-difluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-18);

(S)—N-((3R,4S,5S)-1-((2R,4R)-2-((1R,2R)-3-(((R,Z)-1-(hydroxyimino)-1-(3-methoxyphenyl)propan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-19);

(S)-2-((S)-2-(dimethylamino)-3-methylbutaneamido)-N-((3R,4S,5S)-1-((2R,4R)-2-((1R,2R)-3-(((R)-1-(hydroxyimino)-1-(3-methoxyphenyl)propan-2-yl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-20);

(S)-2-((S)-2-(dimethylamino)-3-methylbutaneamido)-N-((3R,4S,5S)-1-((2R,4R)-2-((1R,2R)-3-(((R)-1-(4-fluorophenyl)-1-(hydroxyimino)propan-2-yl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-21);

(S)—N-((3R,4S,5S)-1-((2R,4R)-2-((1R,2R)-3-((2-(5-bromo-2-methylphenyl)-2-(hydroxyimino)ethyl)amino)-1-methoxy-2-methyl-3-oxopropyl)-4-methoxypyrrolidin-1-yl)-3-methoxy-5-methyl-1-oxoheptan-4-yl)-2-((S)-2-(dimethylamino)-3-methylbutaneamido)-N,3-dimethylbutanamide (I-22);

(S)-2-((S)-2-(dimethylamino)-3-methylbutaneamido)-N-((3R,4S,5S)-1-((2R,4R)-2-((1R,2R)-3-((2-(4-fluoro-2-methylphenyl)-2-(hydroxyimino)ethyl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-23);

(S)—N-((3R,4S,5S)-1-((2R,4R)-2-((1R,2R)-3-((2-(4-fluoro-2-methylphenyl)-2-(hydroxyimino)ethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-24);

(S)—N-((3R,4S,5S)-1-((2S,4R)-2-((1R,2R)-3-(((E)-2-(2-fluoro-4-methoxyphenyl)-2-hydroxyimino)ethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-25);

(S)-2-((S)-2-(dimethylamino)-3-methylbutaneamido)-N-((3R,4S,5S)-1-((2R,4R)-2-((1R,2R)-3-((2-(4-fluoro-2-methylphenyl)-2-(oxoethyl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-26);

(S)—N-((3R,4S,5S)-1-((2R,4R)-2-((1R,2R)-3-((2-(4-fluoro-2-methylphenyl)-2-(oxoethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-27);

(S)—N-((3R,4S,5S)-3-methoxy-1-((2S,4R)-4-methoxy-2-((1R,2R)-1-methoxy-2-methyl-3-oxo-3-((2-oxo-2-(o-tolyl)ethyl)amino)propyl)pyrrolidin-1-yl)-5-methyl-1-oxoheptan-4-yl)-N,3-dimethyl-2-((S)-3-methyl-2-(methylamino)butaneamido)butanamide (I-28);

(S)—N-((3R,4S,5S)-3-methoxy-1-((2S,4R)-4-methoxy-2-((1R,2R)-1-methoxy-2-methyl-3-oxo-3-((2-oxo-2-(p-tolyl)ethyl)amino)propyl)pyrrolidin-1-yl)-5-methyl-1-oxoheptan-4-yl)-N,3-dimethyl-2-((S)-3-methyl-2-(methylamino)butaneamido)butanamide (I-29);

(S)—N-((3R,4S,5S)-1-((2S,4R)-2-((1R,2R)-3-(2-(4-fluorophenyl)-2-oxoethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-30);

(S)—N-((3R,4S,5S)-1-((2S,4R)-2-((1R,2R)-3-(2-(2-fluoro-4-methoxyphenyl)-2-oxoethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-31);

(S)—N-((3R,4S,5S)-1-((S)-4-((1R,2R)-3-((2,6-difluorophenethyl)amino)-1-methoxy-2-methyl-3-oxopropyl)thiazolidin-3-yl)-3-methoxy-5-methyl-1-oxoheptan-4-yl)-N,3-dimethyl-2-((S)-3-methyl-2-(methylamino)butaneamido)butanamide (I-32);

(2S)—N-((3R,4S)-3-methoxy-1-((2S,4S)-4-methoxy-2-((1R,2R)-1-methoxy-2-methyl-3-oxo-3-(phenethylamino)propyl)pyrrolidin-1-yl)-5-methyl-1-oxoheptan-4-yl)-N,3-dimethyl-2-((S)-3-methyl-2-(methylamino)butaneamido)butanamide (I-33);

(2S)—N-((3R,4S)-3-methoxy-1-((2S,4R)-4-methoxy-2-((1R,2R)-1-methoxy-2-methyl-3-oxo-3-((2-oxo-2-phenylethyl)amino)propyl)pyrrolidin-1-yl)-5-methyl-1-oxoheptan-4-yl)-N,3-dimethyl-2-((S)-3-methyl-2-(methylamino)butaneamido)butanamide (I-34);

(2S)—N-((3R,4S)-1-((2S,4R)-2-((1R,2R)-3-(2-(2-hydroxy-2-phenylethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-35);

(2S)—N-((3R,4S)-1-((2S)-2-((1R,2R)-3-(((2R)-1-amino-1-phenylpropan-2-yl)amino)-1-methoxy-2-methyl-3-oxopropyl)-4-methoxypyrrolidin-1-yl)-3-methoxy-5-methyl-1-oxoheptan-4-yl)-2-((S)-2-(dimethylamino)-3-methylbutanamido)-N,3-dimethylbutanamide (I-36);

(2S)—N-((3R,4S)-1-((2S,4R)-2-((1R,2R)-3-(((2S)-1-amino-1-phenylpropan-2-yl)amino)-1-methoxy-2-methyl-3-oxopropyl)-4-methoxypyrrolidin-1-yl)-3-methoxy-5-methyl-1-oxoheptan-4-yl)-2-((S)-2-
(dimethylamino)-3-methylbutaneamido)-N,3-
dimethylbutanamide (I-37);

(2S)—N-((3R,4S)-3-methoxy-1-((2S,4R)-4-methoxy-2-
((1R,2R)-1-methoxy-2-methyl-3-oxo-3-((2-(pyridin-2-
yl)ethyl)amino)propyl)pyrrolidin-1-yl)-5-methyl-1-oxo-
heptan-4-yl)-N,3-dimethyl-2-((S)-3-methyl-2-
(methylamino)butaneamido)butanamide (I-38);

(2S)—N-((3R,4S)-3-methoxy-1-((2S,4R)-4-methoxy-2-
((1R,2R)-1-methoxy-2-methyl-3-oxo-3-((2-(thiophen-2-
yl)ethyl)amino)propyl)pyrrolidin-1-yl)-5-methyl-1-oxo-
heptan-4-yl)-N,3-dimethyl-2-((S)-3-methyl-2-
(methylamino)butaneamido)butanamide (I-39);

(2S)—N-((3R,4S)-1-((2S,4S)-2-((1R,2R)-3-((2,6-difluo-
rophenethyl)amino)-1-methoxy-2-methyl-3-oxopropyl)-
4-hydroxypyrrolidin-1-yl)-3-methoxy-5-methyl-1-oxo-
heptan-4-yl)-2-((S)-2-(dimethylamino)-3-
methylbutaneamido)-N,3-dimethylbutanamide (I-40);

(2S)-2-((S)-2-(dimethylamino)-3-methylbutaneamido)-N-
((3R,4S)-1-((2S,4S)-2-((1R,2R)-3-(((S)-1-(4-fluorophe-
nyl)-1-oxopropan-2-yl)amino)-1-methoxy-2-methyl-3-
oxopropyl)-4-hydroxypyrrolidin-1-yl)-3-methoxy-5-
methyl-1-oxoheptan-4-yl)-N,3-dimethylbutanamide
(I-41);

(2S)—N-((3R,4S)-1-((2S,4S)-2-((1R,2R)-3-(2,6-difluo-
rophenethyl)amino)-1-methoxy-2-methyl-3-oxopropyl)-
4-hydroxypyrrolidin-1-yl)-3-methoxy-5-methyl-1-oxo-
heptan-4-yl)-N,3-dimethyl-2-((S)-3-methyl-2-
(methylamino)butaneamido)butanamide (I-42);

(2S)—N-((3R,4S)-1-((2S,4S)-2-((1R,2R)-3-(((S)-1-(4-fluo-
rophenyl)-1-oxopropan-2-yl)amino)-1-methoxy-2-me-
thyl-3-oxopropyl)-4-hydroxypyrrolidin-1-yl)-3-methoxy-
5-methyl-1-oxoheptan-4-yl)-N,3-dimethyl-2-((S)-3-
methyl-2-(methylamino)butaneamido)butanamide (I-43);

(2S)—N-((3R,4S)-1-((2S,4S)-4-amino-2-((1R,2R)-3-((2,6-
difluorophenethyl)amino)-1-methoxy-2-methyl-3-oxo-
propyl)pyrrolidin-1-yl)-3-methoxy-5-methyl-1-oxohep-
tan-4-yl)-2-((S)-2-(dimethylamino)-3-
methylbutaneamido)-N,3-dimethylbutanamide (I-44); and (2S)—N-((3R,4S)-1-((2S,4S)-2-((1R,2R)-3-(2,6-difluo-
rophenethyl)amino)-1-methoxy-2-methyl-3-oxopropyl)-
4-(methylamino)pyrrolidin-1-yl)-3-methoxy-5-methyl-1-
oxoheptan-4-yl)-2-((S)-2-(dimethylamino)-3-
methylbutaneamido)-N,3-dimethylbutanamide (I-45).

In accordance with another aspect thereof, the present invention addresses a method of producing a dolastatin-10 derivative represented by the following Chemical Formula I, comprising condensing a compound represented by the following Chemical Formula II with a compound represented by the following Chemical Formula III, and deprotecting the condensate if a protecting group exists.

[Chemical Formula II]

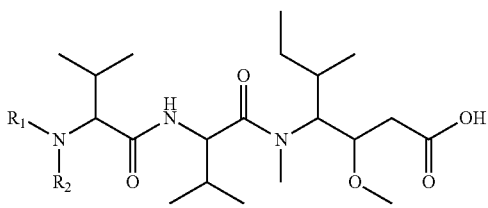

[Chemical Formula III]

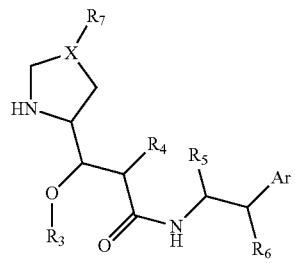

wherein, $R_1$ and $R_2$ are each independently hydrogen, $C_1$-$C_4$ alkyl, or an amino protecting group, $R_3$, $R_4$ and $R_5$ are each independently hydrogen or $C_1$-$C_4$ alkyl, $R_6$ is hydrogen, protected or unprotected hydroxy, $C_1$-$C_4$ alkoxy, protected or unprotected amino, oxo(=O), or hydroxyimino (=N—OH), Ar is aryl, X is a carbon, oxygen or sulfur atom, and $R_7$ is protected or unprotected hydroxy, protected or unprotected amino, $C_1$-$C_4$ alkoxy, protected or unprotected $C_1$-$C_4$ alkylamino, or oxo(=O) when X is a carbon atom, and is absent when X is an oxygen or sulfur atom.

As the amino protecting group, t-butoxycarbonyl (t-Boc), carbobenzyloxy(Cbz), 9-fluorenylmethoxycarbonyl(Fmoc), or benzyl(Bn) may be used, but with no limitations thereto.

For protecting hydroxy, t-butyldimethylsilyl may be used, but with no limitations thereto.

The compound of Chemical Formula III may be in the form of salts including, but not limited to, hydrochloride, and trifluoroacetate (TFA).

The condensation reaction may be carried out in the presence of a condensing agent. Examples of available condensing agents include, but are not limited to, dicyclohexylcarbodiimide (DCC), diphenylphosphorylazide (DPPA), diethyl cyanophosphonate (DEPC), and benzotriazol-1-yl-oxy-tris (dimethylamino)phosphoniumhexafluorophosphate (BOP reagent).

For the condensation reaction, an organic base, such as triethylamine or diisopropylethylamine (DIPEA) may be used as needed, together with the condensing agent.

As a reaction solvent, a halogenated aliphatic hydrocarbon, such as chloroform and dichloromethane, ethylacetate, tetrahydrofuran (THF), dimethylformamide (DMF), and/or acetonitrile may be employed, and the reaction temperature may be preferably set to be 0 to 50° C. and more preferably 0° C. to room temperature.

The deprotection of the amino protecting group may be carried out using 10% palladium carbon or 20% palladium hydroxide.

For the deprotection of the hydroxy protecting group, tetrabutylammonium fluoride may be employed.

The compound of Chemical Formula II may be synthesized as previously disclosed [U.S. Pat. No. 5,654,399; Tetrahedron Letters, Vol. 32, No. 21, pp 2395-2398].

Meanwhile, the compound of Chemical Formula III can be synthesized as illustrated in the following Reaction Scheme I, which is a modification of the previously disclosed method [Tetrahedron, Vol. 49, No. 9, pp. 1913-1924]. The modality described in the following Reaction Scheme is a representative illustration, and can be modified as much as needed with regard to procedure order, reaction reagents, conditions, etc.

[Reaction Scheme I]

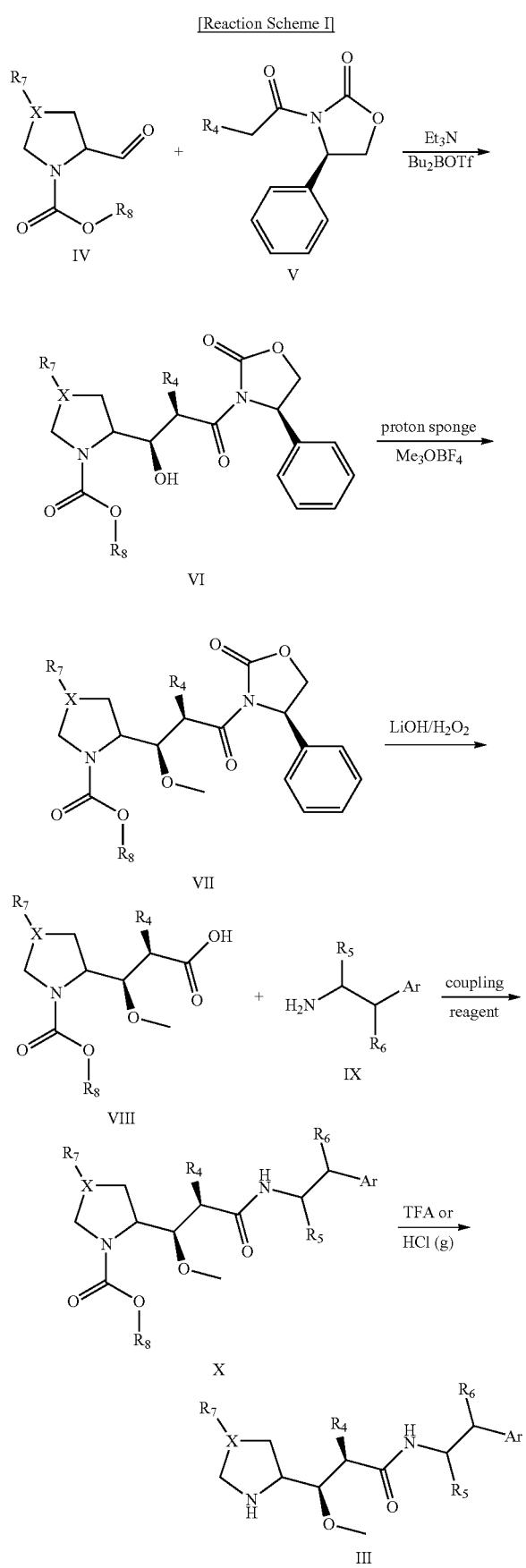

wherein, $R_4$ and $R_5$ are each independently hydrogen or $C_1$-$C_4$ alkyl, $R_6$ is hydrogen, protected or unprotected hydroxy, $C_1$-$C_4$ alkoxy, protected or unprotected amino, oxo (=O), or hydroxyimino (=N—OH), Ar is aryl, X is a carbon, oxygen or sulfur atom, $R_7$ is protected or unprotected hydroxy, protected or unprotected amino, $C_1$-$C_4$ alkoxy, protected or unprotected $C_1$-$C_4$ alkylamino, or oxo (=O) when X is a carbon atom, and is absent when X is an oxygen or sulfur atom, and $R_8$ is $C_1$-$C_4$ alkyl.

As illustrated in Reaction Scheme I, the compound of Chemical Formula IV is reacted with the compounds of Chemical Formula V in the presence of triethylamine as a base and dibutylboron triflate as a Lewis acid to synthesize the compound of Chemical Formula VI. In this regard, the stereochemistry of the compound of Chemical Formula VI can be controlled according to the order of adding the base and the Lewis acid.

Then, the compound of Chemical Formula VI is methylated with trimethyloxonium tetrafluoroborate in the presence of 1,8-bis(dimethylamino)naphthalene (proton sponge) to give the compound of Chemical Formula VII that is then converted into the compound of Chemical Formula VIII in the presence of hydrogen peroxide and lithium hydroxide.

Subsequently, the compound of Chemical Formula VIII is coupled with the compound of Chemical Formula IX to afford the compound of Chemical Formula X. The compound of Chemical Formula IX may be used in the form of salts including, but not limited to, hydrochloride, trifluoroacetate (TFA), etc.

For the condensation reaction (coupling), the same reagents and conditions as in the condensation reaction between the compounds of Chemical Formulas II and III may be employed.

Finally, the amino protecting group of the compound of Chemical Formula X is deprotected with hydrochloric acid or trifluoroacetic acid to produce the compound of Chemical Formula III.

The dolastatin-10 derivative of the present invention exhibits excellent antitumor activity (Test Example 1).

Contemplated in accordance with a further aspect of the present invention is therefore an anticancer agent comprising the dolastatin-10 derivative of Chemical Formula I or a pharmaceutically acceptable salt thereof, and a pharmaceutically acceptable carrier, which is especially therapeutic of breast cancer.

The anticancer agent according to the present invention can be administered non-parenterally (for example, orally or by inhalation) or parenterally (for example, injection, deposition, transplantation, suppository). For injection, administration may be performed, intravenously, subcutaneously, intramuscularly, or intraperitoneally. According to administration route, the anticancer drug of the present invention may be formulated into a tablet, a capsule, a granule, a fine subtilae, a powder, a sublingual tablet, a suppository, a paste, an injection, an emulsion, a suspension, a syrup, a sprayer, etc. When the anticancer drug of the present invention is prepared into various formulations, pharmaceutically acceptable carriers typical of each formulation may be used. Examples of the pharmaceutically acceptable carriers include excipients, binders, disintegrating agents, lubricants, preservatives, antioxidants, isotonic agents, buffers, coating agents, sweeteners, solubilizers, bases, dispersants, humectants, suspending agents, stabilizers, colorants, etc.

In the anticancer drug of the present invention, a content of the compound of the present invention or a pharmaceutically acceptable salt thereof, although varying depending on the formulation, ranges from approximately 0.01 to 95% by weight.

The effective dosage of the anticancer drug of the present invention depends on various factors, including the kind, weight, gender, severity of diseases of the mammal subjects including humans. Typically, the compound according to the present invention may be administered at a daily dose ranging from 0.01 to 50 mg per kg of weight for a non-parenteral route and from 0.01 to 10 mg per kg of weight for a non-parenteral route. The compound may be administered in a single dose or may be divided into multiple doses per day according to the instructions of a physician or pharmacist.

Advantageous Effects

The dolastatin-10 derivatives of the present invention are novel compounds that can be effectively used for treating cancer and inhibiting tumor growth. For example, the compounds are effectively suppressive or preventive of the growth of premalignant and malignant cells, and find useful applications in the treatment of blood cancer as well as carcinoma solid tumors, especially colorectal cancer, lung cancer, breast cancer, stomach cancer, uterine cervical cancer, and bladder cancer.

BEST MODE

A better understanding of the present invention may be obtained through the following examples which are set forth to illustrate, but are not to be construed as the limit of the present invention.

Preparation Example 1

Preparation of Compound of Chemical Formula IV

Preparation Example 1-1

N-t-butoxycarbonyl-L-prolinal (IV-1)

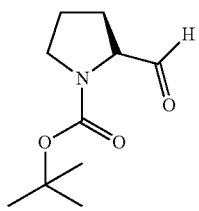

A solution of N-t-butoxycarbonyl-L-prolinol (2 g, 9.9 mmol) in 12 mL of dimethylsulfoxide was cooled to 5~10° C., and mixed with triethylamine (4.8 mL, 34.7 mmol) for 15 min at the same temperature while stirring. To the reaction solution was added a sulfur trioxide-pyridine complex (5.5 g, 34.7 mmol) at 0° C., followed by stirring for 2 hrs.

After completion of the reaction, 50 mL of water was added to the reaction mixture that was then extracted three times with 20 mL of dichloromethane. The organic layers thus obtained were pooled and washed with 50 mL of aqueous 50% citric acid solution, 50 mL of water, and 50 mL of saturated sodium hydrogen carbonate, dried over anhydrous magnesium sulfate, and concentrated in a vacuum. The residue was isolated and purified by column chromatography to afford the title compound. 1.87 g (94%).

$^1$H NMR (400 MHz, CDCl$_3$): δ 1.4~31.46 (m, 9H), 2.18~1.79 (m, 4H), 3.59~3.40 (m, 2H), 4.05~4.20 (m, 1H), 9.46~9.56 (s, 1H)

Preparation Example 1-2

N-t-butoxycarbonyl-trans-4-methoxy-L-prolinal (IV-2)

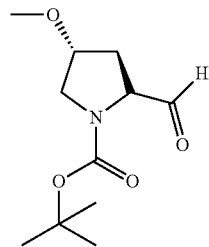

With the exception that N-t-butoxycarbonyl-trans-4-methoxy-L-prolinol, instead of N-t-butoxycarbonyl-L-prolinol, was used, the same procedure as in Preparation Example 1-1 was repeated to afford the title compound. 40.8 g (97%).

$^1$H NMR (400 MHz, CDCl$_3$): δ 1.45 (s, 9H), 1.96~1.98 (m, 1H), 2.1~2.2 (m, 1H), 3.29 (S, 3H), 3.51~3.53 (m, 1H), 3.71~3.73 (m, 1H), 3.93~3.94 (m, 1H), 4.19~4.29 (m, 1H), 9.43 (S, 1H)

Preparation Example 1-3

N-t-butoxycarbonyl-cis-4-methoxy-L-prolinal (IV-3)

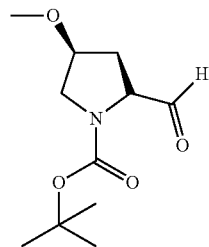

With the exception that N-t-butoxycarbonyl-cis-4-methoxy-L-prolinol, instead of N-t-butoxycarbonyl-L-prolinol, was used, the same procedure as in Preparation Example 1-1 was repeated to afford the title compound. 6.94 g (65%).

$^1$H NMR (400 MHz, CDCl$_3$): δ 1.43 (s, 9H), 2.04~2.17 (m, 1H), 2.7 (m, 1H), 3.24 (S, 3H), 3.43~3.47 (m, 1H), 3.56~3.71 (m, 1H), 3.89~3.91 (m, 1H), 4.05~4.18 (m, 1H), 9.51 (S, 1H)

Preparation Example 1-4

N-t-butoxycarbonyl-cis-4-(t-butyldimethylsilyl)oxy-L-prolinal (IV-4)

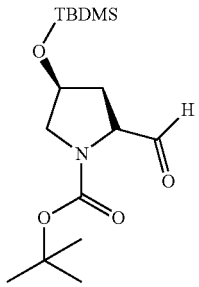

With the exception that N-t-butoxycarbonyl-cis-4-(t-butyldimethylsilyl)oxy-L-prolinol, instead of N-t-butoxycarbonyl-L-prolinol, was used, the same procedure as in Preparation Example 1-1 was repeated to afford the title compound. 3.8 g (52%).

$^1$H NMR (400 MHz, CDCl$_3$): δ 0.04 (s, 3H), 0.07 (s, 3H), 0.85 (s, 9H), 1.45 (s, 9H), 2.04~2.08 (m, 1H), 2.15~2.24 (m, 1H), 3.38~3.52 (m, 2H), 4.06~4.20 (m, 1H), 4.36~4.36 (m, 1H), 9.55 (s, 1H)

Preparation Example 1-5

N-t-butoxycarbonyl-trans-4-(t-butyldimethylsilyl)oxy-L-prolinal (IV-5)

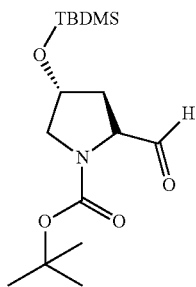

With the exception that N-t-butoxycarbonyl-trans-4-(t-butyldimethylsilyl)oxy-L-prolinol, instead of N-t-butoxycarbonyl-L-prolinol, was used, the same procedure as in Preparation Example 1-1 was repeated to afford the title compound. 9.64 g (66%).

$^1$H NMR (400 MHz, CDCl$_3$): δ 0.07 (s, 6H), 0.87 (s, 9H), 1.45 (s, 9H), 1.89~2.08 (m, 2H), 3.34~3.56 (m, 2H), 4.12~4.37 (m, 2H), 9.43 (S, 1H)

Preparation Example 1-6

(S)-t-butyl 4-formylthiazolidine-3-carboxylate (IV-6)

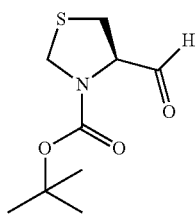

With the exception that (R)-t-butyl-4-(hydroxymethyl)thiazolidine-3-carboxylate, instead of N-t-butoxycarbonyl-L-prolinol, the same procedure as in Preparation Example 1-1 was repeated to afford the title compound. 9.21 g (44%).

$^1$H NMR (400 MHz, CDCl$_3$): δ 1.47 (s, 9H), 3.16~3.23 (m, 2H), 4.27~4.65 (m, 3H), 9.57 (s, 1H)

Preparation Example 2

Preparation of Compound of Chemical Formula VI

Preparation Example 2-1

(S)-t-butyl 2-((1R,2R)-1-hydroxy-2-methyl-3-oxo-3-((R)-2-oxo-4-phenyloxazolidin-3-yl)propyl)pyrrolidine-1-carboxylate (VI-1)

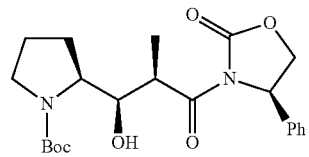 [SMILES: C[C@@H](C(=O)N1C(=O)OC[C@H]1c1ccccc1)[C@@H](O)[C@@H]1CCCN1C(=O)OC(C)(C)C]

To a solution of (R)-4-phenyl-3-propionyloxazolidin-2-one (605 mg, 2.7 mmol) in 8 mL of dichloromethane that was cooled to 0° C., triethyl amine (0.5 mL, 3.7 mmol) was added. Then, dibutylboron triflate was added dropwise and stirred drops of dibutylboron triflate were added before stirring for 45 min. The resulting solution was cooled to −78° C., added dropwise of a solution of the compound (IV-1) (500 mg, 2.5 mmol), obtained in Preparation Example 1-1, in 5 mL of dichloromethane, and stirred for 1 hr. Stirring was further conducted at 0° C. for an additional 1 hr, and at 20~25° C. for an additional 1 hr.

The reaction was terminated with a phosphate buffer (pH 7.2, 3 mL) and 9 mL of methanol. The reaction mixture was cooled to 0° C. before a mixture of methanol: 33% hydrogen peroxide (2:1, 9 mL) was dropwise added thereto. It was stirred for 1 hr, and concentrated in a vacuum. The concentrate was dissolved in ether, washed with saturated sodium chloride, dried over anhydrous sodium sulfate, and concentrated in a vacuum to give a yellow oil. Recrystallization in ethyl acetate afforded the title compound as a white solid. 0.59 g (59%).

MS (EI) m/z: 419 [M+H]$^+$ $^1$H NMR (400 MHz, CDCl$_3$): δ 1.10 (m, 3H), 1.39 (s, 9H), 1.67~1.84 (m, 7H), 3.01 (m, 1H), 3.67~3.81 (m, 3H), 4.14 (m, 1H), 4.70 (m, 1H), 5.03 (m, 1H), 5.43 (m, 1H), 7.26~7.41 (m, 5H)

Preparation Example 2-2

(2S,4R)-t-butyl 2-((1R,2R)-1-hydroxy-2-methyl-3-oxo-3-((R)-2-oxo-4-phenyloxazolidin-3-yl)propyl)-4-methoxypyrrolidine-1-carboxylate (VI-2)

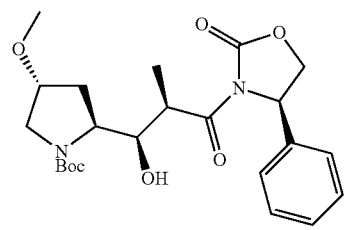 [SMILES: CO[C@@H]1C[C@@H]([C@H](O)[C@@H](C)C(=O)N2C(=O)OC[C@H]2c2ccccc2)N(C(=O)OC(C)(C)C)C1]

With the exception that the compound (IV-2) obtained in Preparation Example 1-2, instead of the compound (IV-1) obtained in Preparation Example 1-1, was used, the same procedure as in Preparation Example 2-1 was repeated to afford the title compound. 3.6 g (28%).

$^1$H NMR (400 MHz, CDCl$_3$): δ 1.24 (m, 3H), 1.47 (m, 9H), 1.98 (m, 1H), 2.25 (m, 1H), 3.28 (s, 3H), 3.35 (m, 1H), 3.48 (m, 3H), 3.61 (m, 1H), 3.92~4.07 (m, 4H), 4.24 (m, 1H), 4.69 (m, 1H), 5.42 (m, 1H), 7.37 (m, 5H)

Preparation Example 2-3

(2S,4R)-t-butyl 4-((t-butyldimethylsilyl)oxy)-2-((1R,2R)-1-hydroxy-2-methyl-3-oxo-3-((R)-2-oxo-4-phenyloxazolidin-3-yl)propyl)pyrrolidine-1-carboxylate (VI-3)

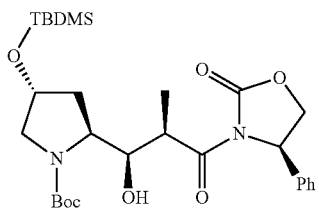

With the exception that the compound (IV-5) obtained in Preparation Example 1-5, instead of the compound (IV-1) obtained in Preparation Example 1-1, was used, the same procedure as in Preparation Example 2-1 was repeated to afford the title compound. 8.9 g (71%).

$^1$H NMR (400 MHz, CDCl$_3$): δ 0.05 (s, 6H), 0.86 (s, 9H), 1.22~1.25 (m, 6H), 1.50 (s, 9H), 1.87 (m, 1H), 2.16~2.18 (m, 1H), 3.22~3.25 (m, 1H), 3.43~3.45 (m, 1H), 3.61 (m, 1H), 3.91~3.92 (m, 1H), 4.13 (m, 1H), 4.25~4.27 (m, 1H), 4.33 (m, 1H), 4.66~4.70 (m, 1H), 5.41~5.45 (m, 1H), 7.26~7.39 (m, 5H)

Preparation Example 3

Preparation of Compound of Chemical Formula VII

Preparation Example 3-1

(S)-t-butyl 2-((1R,2R)-1-methoxy-2-methyl-3-oxo-3-((R)-2-oxo-4-phenyloxazolidin-3-yl)propyl)pyrrolidine-1-carboxylate (VII-1)

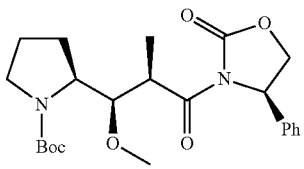 [SMILES: CO[C@H]([C@@H](C)C(=O)N1C(=O)OC[C@H]1c1ccccc1)[C@@H]1CCCN1C(=O)OC(C)(C)C]

In 100 mL of dichloromethane, the compound (VI-1) (5 g, 12.0 mmol) obtained in Preparation Example 2-1, and 4-Å molecular sieves were mixed for 15 min at room temperature while stirring. The resulting solution was cooled to 0° C., added with proton sponge (6.7 g, 31.0 mmol) and trimethyloxoniumtetrafluoroborate (4.4 g, 30.0 mmol), and stirred for 2 hrs. After the temperature was elevated to 20~25° C., stirring was conducted for an additional 46 hrs.

When the reaction was completed, filtration was performed with celite, followed by vacuum concentration. The residue was isolated and purified by column chromatography (n-hexane:ethylacetate=5:1) to afford the title compound. 5.1 g (57%).

MS (EI) m/z: 433 [M+H]$^+$ $^1$H NMR (400 MHz, CDCl$_3$): δ 1.21 (m, 3H), 1.45 (m, 9H), 1.79~1.91 (m, 3H), 3.20-3.55 (m, 5H), 3.80 (m, 2H), 4.09 (m, 2H), 4.24 (m, 1H), 4.66 (m, 1H), 5.43 (m, 1H), 7.36 (m, 5H)

Preparation Example 3-2

(2S,4R)-t-butyl 4-methoxy-2-((1R,2R)-1-methoxy-2-methyl-3-oxo-3-((R)-2-oxo-4-phenyloxazolidin-3-yl)propyl)pyrrolidine-1-carboxylate (VII-2)

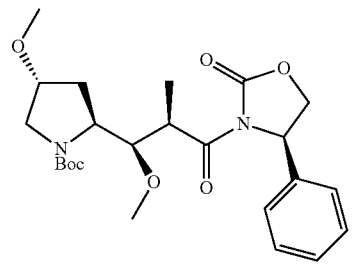 [SMILES: CO[C@@H]1C[C@@H]([C@H](OC)[C@@H](C)C(=O)N2C(=O)OC[C@H]2c2ccccc2)N(C(=O)OC(C)(C)C)C1]

With the exception that the compound (VI-2) obtained in Preparation Example 2-2 was used instead of the compound (VI-1) obtained in Preparation Example 2-1, the same procedure as in Preparation Example 3-1 was repeated to afford the title compound. 1.6 g (45%).

$^1$H NMR (400 MHz, CDCl$_3$): δ 1.21 (m, 3H), 1.47 (m, 9H), 1.92 (m, 1H), 2.16 (m, 1H), 3.33 (m, 3H), 3.47 (m, 3H), 3.76-4.10 (m, 6H), 4.24 (m, 1H), 4.66 (m, 1H), 5.30-5.39 (m, 1H), 7.33 (m, 5H)

Preparation Example 3-3

(2S,4R)-t-butyl 4-((t-butyldimethylsilyl)oxy)-2-((1R,2R)-1-methoxy-2-methyl-3-oxo-3-((R)-2-oxo-4-phenyloxazolidin-3-yl)propyl)pyrrolidine-1-carboxylate (VII-3)

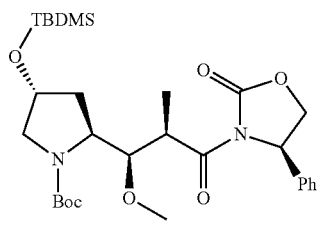

With the exception that the compound (VI-3) obtained in Preparation Example 2-3 was used instead of the compound (VI-1) obtained in Preparation Example 2-1, the same procedure as in Preparation Example 3-1 was repeated to afford the title compound. 6.5 g (71%).

$^1$H NMR (400 MHz, CDCl$_3$): δ 0.05 (s, 6H), 0.86 (s, 9H), 1.18~1.20 (d, 3H), 1.45~1.49 (d, 9H), 1.87 (m, 1H), 2.16~2.18 (m, 1H), 3.29~3.30 (m, 1H), 3.41 (s, 3H), 3.69~3.80 (m, 1H), 3.89~3.93 (m, 1H), 3.99~4.07 (m, 1H), 4.23~4.26 (m, 1H), 4.38 (m, 1H), 4.63~4.66 (m, 1H), 5.38~5.49 (m, 1H), 7.26~7.39 (m, 5H)

Preparation Example 4

Preparation of Compound of Chemical Formula VIII

Preparation Example 4-1

(2R,3R)-3-((S)-1-(t-butoxycarbonyl)pyrrolidin-2-yl)-3-methoxy-2-methylpropanoic acid (VIII-1)

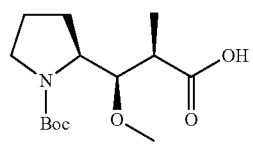 [SMILES: CO[C@H]([C@@H](C)C(=O)O)[C@@H]1CCCN1C(=O)OC(C)(C)C]

A solution of the compound (VII-1) (5.7 g, 13.2 mmol) obtained in Preparation Example 3-1 in 65 mL of tetrahydrofuran was cooled to 0° C., added with 30% hydrogen peroxide (6.6 mL, 66.0 mmol) and 0.4 N lithium hydroxide (66 mL, 26.4 mmol), and stirred for 3 hrs.

The reaction was completed with 1 M sodium sulfite (72.6 mL, 72.6 mmol), and the reaction mixture was stirred at 20-25° C. for 16 hrs and then extracted with saturated sodium hydrogen carbonate and dichloromethane, both cold to 0~5° C. Using 1 N HCl, the aqueous layer was adjusted to a pH of 2, followed by three rounds of extraction with ethylacetate. The organic layers thus obtained were pooled, dried over anhydrous magnesium sulfate, and concentrated in a vacuum to afford the title compound. 3.8 g (99%).

$[\alpha]_D$ 25=−57° (c=1, MeOH)

$^1$H NMR (400 MHz, CDCl$_3$): δ 1.28 (m, 3H), 1.45 (m, 9H), 1.75 (m, 1H), 1.95 (m, 1H), 2.50 (m, 1H), 3.25 (m, 1H), 3.45 (s, 3H), 3.97 (m, 1H), 3.80-3.98 (m, 2H), 11.1 (br, 1H)

Preparation Example 4-2

(2R,3R)-3-((2S,4R)-1-(t-butoxycarbonyl)-4-methoxypyrrolidin-2-yl)-3-methoxy-2-methylpropanoic acid (VIII-2)

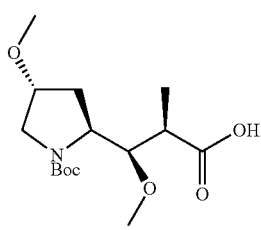 [SMILES: CO[C@@H]1C[C@@H]([C@H](OC)[C@@H](C)C(=O)O)N(C(=O)OC(C)(C)C)C1]

With the exception that the compound (VII-2) obtained in Preparation Example 3-2 was used instead of the compound (VII-1) obtained in Preparation Example 3-1, the same procedure as in Preparation Example 4-1 was repeated to afford the title compound. 1.5 g (93%).

$^1$H NMR (400 MHz, CDCl$_3$): δ 1.28 (m, 3H), 1.47 (m, 9H), 1.99-2.55 (m, 4H), 3.30 (s, 3H), 3.46 (s, 3H), 3.55~4.15 (m, 4H)

Preparation Example 4-3

(2R,3R)-3-((2R,4R)-1-(t-butoxycarbonyl)-4-((t-butyldimethylsilyl)oxy)pyrrolidin-2-yl)-3-methoxy-2-methylpropanoic acid (VIII-3)

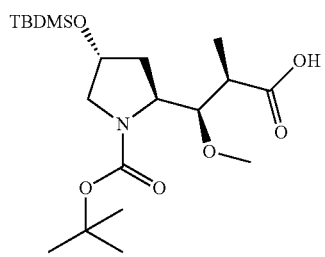 [SMILES: CO[C@H]([C@@H](C)C(=O)O)[C@@H]1C[C@@H](O[Si](C)(C)C(C)(C)C)CN1C(=O)OC(C)(C)C]

With the exception that the compound (VII-3) obtained in Preparation Example 3-3 was used instead of the compound (VII-1) obtained in Preparation Example 3-1, the same procedure as in Preparation Example 4-1 was repeated to afford the title compound. 1.04 g (100%).

$^1$H NMR (400 MHz, CDCl$_3$): δ 0.05 (s, 6H), 0.86 (s, 9H), 1.26 (d, 3H), 1.48 (s, 9H), 1.84 (m, 1H), 2.07 (m, 1H), 2.45~2.57 (m, 1H), 3.27~3.30 (m, 1H), 3.34~3.53 (m, 1H), 3.46 (S, 3H), 3.86~3.87 (m, 1H), 4.05 (m, 1H), 4.37 (m, 1H)

Preparation Example 4-4

(2R,3R)-3-((2S,4S)-1-(t-butoxycarbonyl)-4-hydroxypyrrolidin-2-yl)-3-methoxy-2-methylpropanoic acid (VIII-4)

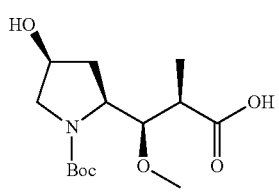 [SMILES: CO[C@H]([C@@H](C)C(=O)O)[C@@H]1C[C@H](O)CN1C(=O)OC(C)(C)C]

To a solution of the compound (VII-3) (6.4 g, 11.55 mmol) obtained in Preparation Example 3-3 in 50 mL of tetrahydrofuran was slowly added pyridine hydrofluoride (1.0 ml, 69.3 mmol) while stirring at 20~25° C. for 3 hrs. After completion of the reaction, the reaction mixture was added with 50 mL of an aqueous saturated sodium hydrogen carbonate solution, and then extracted with 50 mL of ethylacetate. The organic layer thus formed was washed with 50 mL of 1 N HCl, dried over anhydrous sodium sulfate, and concentrated in a vacuum to afford (2S,4R)-t-butyl 4-hydroxy-2-((1R,2R)-1-methoxy-2-methyl-3-oxo-3-((R)-2-oxo-4-phenyloxazolidin-3-yl)propyl)pyrrolidine-1-carboxylate. 5.4 g (104%).

The concentrate was dissolved in 120 mL of tetrahydrofuran in an argon atmosphere, added with triphenylphosphine (4.71 g, 17.75 mmol), and cooled to 0~5° C. The reaction solution was mixed with formic acid (0.67 ml, 17.75 mmol), followed by slow addition of drops of diisopropyl azodicarboxylate (3.5 g, 17.75 mmol). Subsequently, stirring was conducted at 0~5° C. for 30 min and then at 20~25° C. for 16 hrs. When the reaction was completed, the reaction mixture was concentrated in a vacuum to obtain (2S,4S)-t-butyl 4-(formyloxy)-2-((1R,2R)-1-methoxy-2-methyl-3-oxo-3-((R)-2-oxo-4-phenyloxazolidin-3-yl)propyl)pyrrolidine-1-carboxylate.

The residue was cooled to 0~5° C., and slowly added with drops of hydrogen peroxide (11.1 ml, 115.5 mmol) and then with 1 M lithium hydroxide (2.42 g, 57.8 mmol). This reaction solution was stirred at 0~5° C. for 4 hrs, after which tetrahydrofuran was removed by vacuum concentration. The residue was extracted with 100 mL of dichloromethane and 100 mL of water. The aqueous layer was isolated, adjusted with 1 N HCl to a pH of 2, and extracted twice with 100 mL of ethylacetate. The organic layers thus obtained were pooled, dried over magnesium sulfate, and concentrated in a vacuum to afford the title compound. 3.18 g (91%).

$^1$H NMR (400 MHz, CDCl$_3$): δ 1.34 (d, 3H, J=7.2 Hz), 1.47 (m, 9H), 1.97~2.00 (m, 1H), 2.19~2.23 (m, 1H), 2.54~2.57 (m, 1H), 3.40~3.59 (m, 2H), 3.49 (s, 3H), 3.87~3.99 (m, 1H), 4.08~4.15 (m, 1H), 4.24~4.28 (m, 1H)

LC-MS m/z: 302.1[M−H]

Preparation Example 4-5

(2R,3R)-3-((2S,4S)-4-azido-1-(t-butoxycarbonyl)pyrrolidin-2-yl)-3-methoxy-2-methylpropanoic acid (VIII-5)

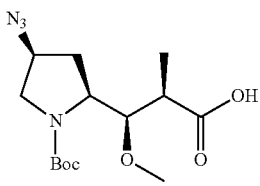 [SMILES: CO[C@H]([C@@H](C)C(=O)O)[C@@H]1C[C@H](N=[N+]=[N-])CN1C(=O)OC(C)(C)C]

With the exception that diphenyl phosphoryl azide was used instead of diisopropyl azodicarboxylate, the same procedure as in Preparation Example 4-4 was repeated to afford the title compound. 4.94 g (90%).

[α]$_D$25=−13.6° (c=1, MeOH)

$^1$H NMR (400 MHz, CDCl$_3$): δ 1.28 (d, 3H, J=6.8 Hz), 1.47 (s, 9H), 2.05 (m, 1H), 2.23~2.30 (m, 1H), 2.46~2.48 (m, 1H), 3.05 (m, 1H), 3.48 (s, 3H), 3.88~3.04 (m, 3H)

Preparation Example 4-6

(2R,3R)-3-((S)-3-(t-butoxycarbonyl)thiazolidin-4-yl)-3-methoxy-2-methylpropanoic acid (VIII-6)

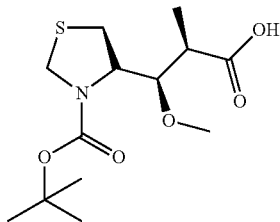

With the exception that (R)-t-butyl-4-((1R,2R)-1-methoxy-2-methyl-3-oxo-3-((R)-2-oxo-4-phenyloxazolidin-3-yl)propyl)thiazolidine-3-carboxylate was used instead of the compound (VII-1) obtained in Preparation Example 3-1, the same procedure as in Preparation Example 4-1 was repeated to afford the title compound. 0.89 g (100%).

$^1$H NMR (400 MHz, CDCl$_3$): δ 1.17~1.25 (d, 3H), 1.47 (s, 9H), 2.65~3.12 (m, 4H), 3.42 (S, 3H), 3.77~4.18 (m, 2H), 4.16~4.21 (m, 2H)

Preparation Example 5

Preparation of Compound of Chemical Formula IX

Preparation Example 5-1

2-(2,6-difluorophenyl)ethanamine (IX-1)

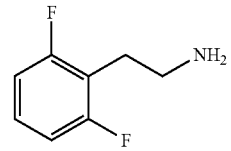 [SMILES: NCCc1c(F)cccc1F]

2-(2,6-Difluorophenyl)acetonitrile (2.34 g, 15.28 mmol) was added to potassium boron hydride (3.29 g, 61.12 mmol) and Raney nickel (0.897 g, 15.28 mmol) in 50 mL of absolute ethanol while stirring. Then, vigorously stirring was continued at room temperature for 5 hrs.

After completion of the reaction, the reaction mixture was filtered through celite, and concentrated in a vacuum. The residue was extracted with ether and water, and washed with brine. The organic layer was dried over anhydrous magnesium sulfate to afford the title compound as a dark yellow oil.

$^1$H NMR (400 MHz, CDCl$_3$): δ 2.88 (m, 2H), 2.98 (m, 2H), 5.11 (br, 1H), 7.32 (m, 2H), 7.59 (m, 1H)

Preparation Example 5-2

2-(3-fluorophenyl)Ethanamine (IX-2)

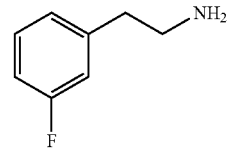

With the exception that 2-(3-fluorophenyl)acetonitrile was used instead of 2-(2,6-difluorophenyl)acetonitrile, the same procedure as in Preparation Example 5-1 was repeated to afford the title compound.

$^1$H NMR (400 MHz, CDCl$_3$): δ 2.88 (m, 2H), 2.98 (m, 2H), 5.11 (br, 1H), 6.83 (m, 1H), 7.06 (m, 2H), 7.38 (m, 1H)

Preparation Example 5-3

2-(2,4-dichloro-5-fluorophenyl)ethanamine (IX-3)

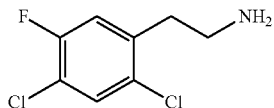 [SMILES: NCCc1cc(F)c(Cl)cc1Cl]

With the exception that 2-(2,4-dichloro-5-fluorophenyl)acetonitrile was used instead of 2-(2,6-difluorophenyl)acetonitrile, the same procedure as in Preparation Example 5-1 was repeated to afford the title compound.

$^1$H NMR (400 MHz, CDCl$_3$): δ 2.83 (m, 2H), 2.98 (m, 2H), 5.11 (br, 1H), 6.71 (m, 1H), 7.62 (m, 1H)

Preparation Example 5-4

2-amino-1-(2-fluoro-4-methoxyphenyl)ethanone (IX-4)

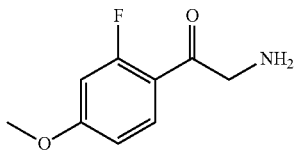

To a solution of 2-azido-1-(2-fluoro-4-methoxyphenyl)ethanone (4.80 g, 25.36 mmol) in 100 mL of tetrahydrofuran were added triphenylphosphine (6.65 g, 25.36 mmol) and p-toluenesulfonic acid (14.5 g, 76.11 mmol), followed by stirring at room temperature for 16 hrs.

The precipitate that was formed as the reaction terminated was filtered, washed with cold tetrahydrofuran, and dried at 35° C. to afford the title compound as a white solid. 5.12 g (61%).

$^1$H NMR (400 MHz, DMSO-d$_6$): δ 3.83 (s, 3H), 4.33 (s, 2H), 6.92 (m, 1H), 7.06 (m, 1H), 7.88 (m, 1H), 7.91 (m, 2H), 8.17 (br, 1H)

Preparation Example 5-5

(R)-t-butyl[1-(4-methoxyphenyl)-1-oxopropan-2-yl]carbamate (IX-5)

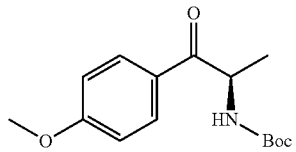 [SMILES: COc1ccc(C(=O)[C@@H](C)NC(=O)OC(C)(C)C)cc1]

A solution of (R)-t-butyl(1-(methoxy(methyl)amino)-1-oxopropan-2-yl)carbamate (5.0 g, 21.5 mmol) in 50 mL of tetrahydrofuran was cooled to −20° C. 4-Methoxyphenylmagnesium bromide was prepared by stirring magnesium (2.1 g, 86.1 mmol), 4-methoxybromobenzene (16.1 g, 86.1 mmol), and a catalytically effective amount of iodide in 100 mL of tetrahydrofuran, and dropwise added to the solution. A reaction was conducted at 20~25° C. for 16 hrs while stirring.

When the reaction was completed, the addition of 100 mL of 1 N HCl gave two separated layers. The aqueous layer was extracted three times with 100 mL of ethylacetate. The organic layers were pooled, dried over anhydrous magnesium sulfate, and concentrated in a vacuum. The residue was isolated and purified by column chromatography to afford the title compound. 6.2 g (66.2%).

$^1$H NMR (400 MHz, CDCl$_3$): δ 1.40 (d, 3H), 1.46 (s, 9H), 3.88 (s, 3H), 5.24 (m, 1H), 5.62 (br, 1H), 6.96 (d, 2H), 7.96 (d, 2H)

Preparation Example 5-6

(R)-t-butyl[1-(2-methoxyphenyl)-1-oxopropan-2-yl]carbamate (IX-6)

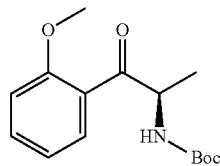 [SMILES: COc1ccccc1C(=O)[C@@H](C)NC(=O)OC(C)(C)C]

With the exception that 2-methoxybromobenzene was used instead of 4-methoxybromobenzene, the same procedure as in Preparation Example 5-5 was repeated to afford the title compound. 2.31 g (75.9%).

$^1$H NMR (400 MHz, CDCl$_3$): δ 1.32 (d, 3H), 1.45 (s, 9H), 3.92 (s, 3H), 5.32 (m, 1H), 5.59 (br, 1H), 7.0 (m, 2H), 7.49 (m, 1H), 7.76 (m, 1H)

Preparation Example 5-7

(S)-t-butyl(1-(3,5-difluorophenyl)-1-oxopropan-2-yl)carbamate (IX-7)

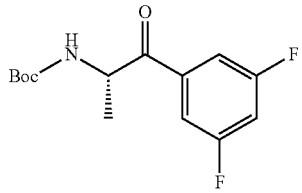 [SMILES: C[C@H](NC(=O)OC(C)(C)C)C(=O)c1cc(F)cc(F)c1]

With the exception that (S)-t-butyl(1-(methoxy(methyl)amino)-1-oxopropan-2-yl)carbamate and 1-bromo-3,5-difluorobenzene were used instead of (R)-t-butyl(1-(methoxy(methyl)amino)-1-oxopropan-2-yl)carbamate and 4-methoxybromobenzene, respectively, the same procedure as in Preparation Example 5-5 was repeated to afford the title compound. 1.3 g (46%).

$^1$H NMR (400 MHz, CDCl$_3$): δ 1.40 (d, J=7.2 Hz, 3H), 1.46 (s, 9H), 5.15~5.19 (m, 1H), 5.41~5.43 (m, 1H), 7.03~7.08 (m, 1H), 7.48~7.50 (m, 2H)

Preparation Example 5-8

(R)-t-butyl(1-(2,6-difluorophenyl)-1-oxopropan-2-yl)carbamate (IX-8)

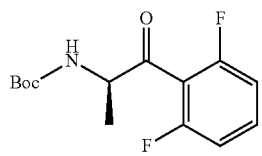 [SMILES: C[C@@H](NC(=O)OC(C)(C)C)C(=O)c1c(F)cccc1F]

With the exception that 1-bromo-2,6-difluorobenzene was used instead of 4-methoxybromobenzene, the same procedure as in Preparation Example 5-5 was repeated to afford the title compound 0.16 g (10%).

$^1$H NMR (400 MHz, CDCl$_3$): δ 1.39 (d, J=7.2 Hz, 3H), 1.41 (s, 9H), 4.87~5.19 (m, 1H), 5.30~5.31 (m, 1H), 6.94~7.0 (m, 2H), 7.39~7.46 (m, 1H)

Preparation Example 5-9

(S)-t-butyl(1-(2,6-difluorophenyl)-1-oxopropan-2-yl) carbamate (IX-9)

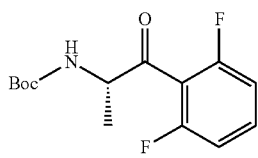 [SMILES: C[C@H](NC(=O)OC(C)(C)C)C(=O)c1c(F)cccc1F]

With the exception that (S)-t-butyl(1-(methoxy(methyl) amino)-1-oxopropan-2-yl)carbamate and 1-bromo-2,6-difluorobenzene were used instead of (R)-t-butyl(1-(methoxy (methyl)amino)-1-oxopropan-2-yl)carbamate and 4-methoxybromobenzene, respectively, the same procedure as in Preparation Example 5-5 was repeated to afford the title compound. 0.26 g (17%).

$^1$H NMR (400 MHz, CDCl$_3$): δ 1.39 (d, J=7.2 Hz, 3H), 1.41 (s, 9H), 4.83~4.87 (m, 1H), 5.30~5.31 (m, 1H), 6.94~6.99 (m, 2H), 7.39~7.46 (m, 1H)

Preparation Example 5-10

(R)-t-butyl[1-(3-methoxyphenyl)-1-oxopropan-2-yl] carbamate (IX-10)

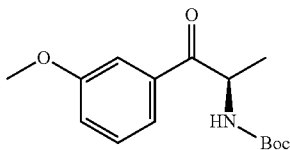 [SMILES: COc1cccc(C(=O)[C@@H](C)NC(=O)OC(C)(C)C)c1]

With the exception that 3-methoxybromobenzene was used instead of 4-methoxybromobenzene, the same procedure as in Preparation Example 5-5 was repeated to afford the title compound. 2.56 g (71%).

$^1$H NMR (400 MHz, CDCl$_3$): δ 1.32 (d, 3H), 1.45 (s, 9H), 3.94 (s, 3H), 5.32 (m, 1H), 5.61 (br, 1H), 7.12 (m, 3H), 7.62 (m, 1H)

Preparation Example 5-11

(R)-t-butyl[1-(hydroxyimino)-1-(3-methoxyphenyl) propan-2-yl]carbamate (IX-11)

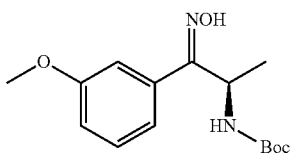

The compound (IX-10) (0.3 g, 1.1 mmol) obtained in Preparation Example 5-10, hydroxylamine hydrochloride (0.18 g, 2.7 mmol), and sodium acetate (0.2 g, 2.7 mmol) were dissolved in 15 mL of a mixture of ethanol and water (5/1), and heated for 3 hrs under reflux.

After completion of the reaction, the reaction mixture was cooled to 20~25° C., neutralized with 1.3 mL of a saturated sodium carbonate solution, and concentrated by vacuum distillation. The concentrate was dissolved in 15 mL of water and 20 mL of ethylacetate. The aqueous layer was extracted three times with 20 mL of ethylacetate. The organic layers thus obtained were pooled, dried over anhydrous magnesium sulfate, and concentrated in a vacuum. The concentrate was purified by column chromatography to afford the title compound as a mixture of E and Z-isomers (1:2). 0.27 g (85.2%).

$^1$H NMR (400 MHz, CDCl$_3$): δ 1.39 (s, 9H), 1.43 (m, 3H), 3.78 (s, 3H), 4.69 (m, 1H), 5.26 (br, 1H), 7.33~6.89 (m, 4H) (E-isomer)

$^1$H NMR (400 MHz, CDCl$_3$): δ 1.39 (s, 9H), 1.43 (m, 3H), 3.78 (s, 3H), 5.05 (m, 1H), 5.82 (br, 1H), 7.33~6.89 (m, 4H) (Z-isomer)

Preparation Example 5-12 t-butyl((2R)-1-amino-1-phenylpropan-2-yl)-carbamate (IX-12)

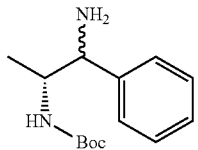 [SMILES: C[C@@H](NC(=O)OC(C)(C)C)C(N)c1ccccc1]

In a reaction vessel that was vacuumed and then purged with argon, (R)-t-butyl[1-phenyl-1-oxopropan-2-yl]carbamate (0.75 g (3.0 mmol)) and ammonium chloride (0.24 g (4.5 mmol)) were placed. Then, dry tetrahydrofuran (15 mL) and triethylamine (0.63 mL (4.5 mmol)) was added to the reaction vessel, followed by titanium tetraisopropoxide (1.32 mL (4.5 mmol)). At room temperature, the reaction mixture was stirred for 8~10 hrs. After addition of ammonium borane, the reaction mixture was again stirred for 8~10 hrs.

Extraction with 1 M ammonia water (15 mL) and ether (15 mL) was performed, after which the organic layer was washed with 9 mL of 1 M HCl. The aqueous layer was adjusted to a pH of 7~8 with 1 M sodium hydroxide, and extracted with 15 mL of ether. The organic layer thus obtained was washed with brine, dried over anhydrous sodium sulfate, and concentrated in a vacuum to afford the title compound. 0.096 g (17%).

$^1$H NMR (400 MHz, CDCl$_3$): δ 0.95 (d, 1H), 1.02 (d, 3H), 1.20 (d, 1H), 1.46 (s, 9H), 7.26~7.34 (m, 5H)

Preparation Example 5-13 benzyl t-butyl((2R)-1-phenylpropan-1,2-diyl)dicarbamate (IX-13)

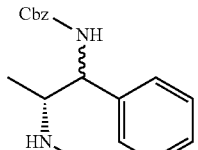

To the compound (IX-12) (0.37 g (1.47 mmol)) obtained in Preparation Example 5-12, 5 mL of dichloromethane and 0.45 mL (3.23 mmol) of triethylamine was added, followed by slow addition of benzylchloroformate at 0° C. After stirring at room temperature at 12~18 hrs, extraction was performed with water and ethylacetate. The organic layer was dried over anhydrous sodium sulfate and concentrated in a vacuum to afford the title compound. 0.37 g (49%).

¹H NMR (400 MHz, CDCl₃): δ 1.09 (d, 3H), 1.42 (s, 9H), 3.93~4.42 (m, 2H), 4.70~4.75 (m, 1H) 4.97~5.17 (m, 2H), 6.02~6.33 (d, 1H), 6.92~7.34 (m, 5H)

Preparation Example 5-14 t-butyl((2S)-1-amino-1-phenylpropan-2-yl)carbamate (IX-14)

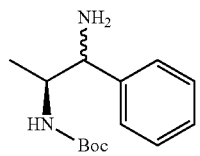 [SMILES: C[C@H](NC(=O)OC(C)(C)C)C(N)c1ccccc1]

With the exception that (S)-t-butyl[1-phenyl-1-oxopropan-2-yl]carbamate was used instead of (R)-t-butyl[1-phenyl-1-oxopropan-2-yl]carbamate, the same procedure as in Preparation Example 5-12 was repeated to afford the title compound. 0.5 g (67%).

¹H NMR (400 MHz, CDCl₃): δ 0.95 (d, 1H), 1.01 (d, 3H), 1.20 (d, 1H), 1.45 (s, 9H), 7.24~7.34 (m, 5H)

Preparation Example 5-15 benzyl t-butyl((2S)-1-phenylpropan-1,2-diyl)dicarbamate (IX-15)

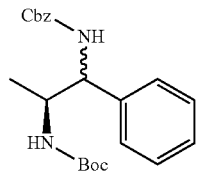

With the exception that the compound (IX-12) obtained in Preparation Example 5-14 was used instead of the compound (IX-14) obtained in Preparation Example 5-12, the same procedure as in Preparation Example 5-13 was repeated to afford the title compound. 0.22 g (28%).

¹H NMR (400 MHz, CDCl₃): δ 0.98 (d, 3H), 1.40 (s, 9H), 3.93~4.41 (m, 1H), 4.68~4.73 (m, 1H), 4.97~5.18 (m, 2H), 6.03~6.33 (d, 1H), 7.21~7.52 (m, 5H)

Preparation Example 6

Preparation of Compound of Chemical Formula X

Preparation Example 6-1

(2R,4R)-t-butyl 2-((1R,2R)-3-((2,6-difluorophenethyl)amino)-1-methoxy-2-methyl-3-oxopropyl)-4-methoxypyrrolidine-1-carboxylate (X-1)

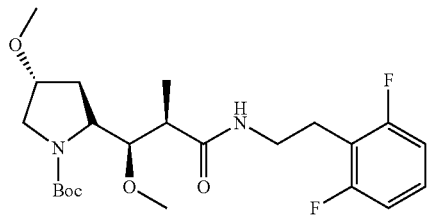

To a solution of the compound (VIII-2) (1.00 g, 3.48 mmol) obtained in Preparation Example 4-2 in 10 mL of dimethylformamide was dropwise added the compound (IX-1) (0.66 g, 4.18 mmol) of Preparation Example 5-1 at 0° C. Then, diisopropylethylamine (1.73 mL, 10.44 mmol) and benzotriazol-1-yl-oxy-tris(dimethylamino)phosphonium hexafluorophosphate (1.54 g, 3.48 mmol) were added before stirring at 20~25° C. for 16 hrs.

When the reaction was completed, the reaction solvent was removed by vacuum concentration, and the residue was dissolved in ethylacetate, extracted twice with water, and washed with brine. The organic layer was dried over anhydrous magnesium sulfate, and concentrated in a vacuum, followed by purification through column chromatography (ethylacetate:hexane=1:3→ethylacetate:hexane=1:1) to afford the title compound as a white oil. 1.31 g (85%).

¹H NMR (400 MHz, CDCl₃): δ 1.22 (d, 3H), 1.46 (s, 9H), 1.65~1.86 (m, 4H), 2.33~3.37 (m, 1H), 2.82 (t, 2H), 3.22~3.24 (m, 1H), 3.29 (s, 3H), 3.4 (s, 3H), 3.48~3.55 (m, 2H), 3.75~3.83 (m, 2H), 5.77~6.51 (m, 1H), 6.65~6.74 (m, 3H)

Preparation Example 6-2

(2R,4R)-t-butyl 2-((1R,2R)-3-((2,4-dichloro-5-fluorophenethyl)amino)-1-methoxy-2-methyl-3-oxopropyl)-4-methoxypyrrolidine-1-carboxylate (X-2)

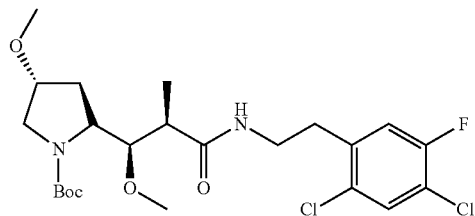

With the exception that the compound (IX-1) obtained in Preparation Example 5-1 was used instead of the compound (IX-3) obtained in Preparation Example 5-3, the same procedure as in Preparation Example 6-1 was repeated to afford the title compound. 0.65 g (78%).

¹H NMR (400 MHz, CDCl₃): δ 1.25 (d, 3H), 1.49 (s, 9H), 1.67~1.88 (m, 4H), 2.33~3.35 (m, 1H), 2.94 (t, 2H), 3.23 (m, 1H), 3.24 (s, 3H), 3.41 (s, 3H), 3.46~3.52 (m, 2H), 3.77~3.82 (m, 2H), 5.79~6.58 (m, 1H), 7.10 (m, 1H), 7.40 (m, 1H)

Preparation Example 6-3

(2R,4R)-t-butyl 2-((1R,2R)-3-((3-fluorophenethyl)amino)-1-methoxy-2-methyl-3-oxopropyl)-4-methoxypyrrolidine-1-carboxylate (X-3)

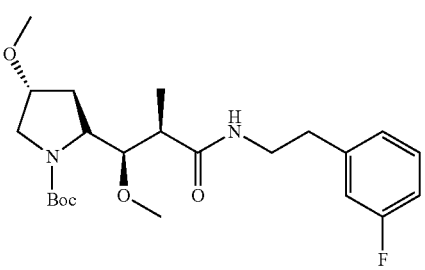

With the exception that the compound (IX-2) obtained in Preparation Example 5-2 was used instead of the compound (IX-1) obtained in Preparation Example 5-1, the same procedure as in Preparation Example 6-1 was repeated to afford the title compound. 0.65 g (95%).

$^1$H NMR (400 MHz, CDCl$_3$): δ 1.24 (m, 3H), 1.48 (s, 9H), 1.68 (m, 3H), 1.85 (m, 2H), 2.34 (m, 1H), 2.83 (t, 2H), 3.20~3.41 (m, 1H), 3.29 (s, 3H), 3.43 (s, 3H), 3.51~3.56 (m, 2H), 3.66~3.83 (m, 2H), 5.71~6.38 (m, 1H), 6.92 (d, 1H), 6.99 (d, 1H), 7.24 (m, 2H)

Preparation Example 6-4

(2R,4R)-t-butyl 2-((1R,2R)-3-((4-fluorophenethyl)amino)-1-methoxy-2-methyl-3-oxopropyl)-4-methoxypyrrolidine-1-carboxylate(X-4)

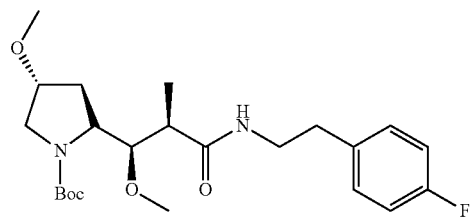

With the exception that 2-(4-fluorophenyl)ethanamine was used instead of the compound (IX-1) obtained in Preparation Example 5-1, the same procedure as in Preparation Example 6-1 was repeated to afford the title compound. 0.66 g (93%).

$^1$H NMR (400 MHz, CDCl$_3$): δ 1.24 (m, 3H), 1.49 (s, 9H), 1.65 (m, 3H), 1.76 (m, 2H), 2.32 (m, 1H), 2.80 (t, 2H), 3.22 (m, 1H), 3.23 (s, 3H), 3.27 (s, 3H), 3.43 (s, 3H), 3.48~3.55 (m, 2H), 3.72~3.82 (m, 2H), 5.68~6.32 (m, 1H), 6.97 (s, 2H), 7.16 (d, 2H)

Preparation Example 6-5

(2R,4R)-t-butyl 4-((t-butyldimethylsilyl)oxy)-2-((1R,2R)-1-methoxy-2-methyl-3-oxo-3-(phenethylamino)propyl)pyrrolidine-1-carboxylate(X-5)

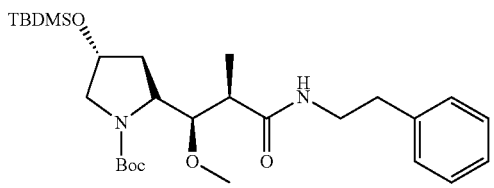

With the exception that the compound (VIII-3) obtained in Preparation Example 4-3 and 2-phenetamine were used instead of the compound (VIII-2) obtained in Preparation Example 4-2 and the compound (IX-1) obtained in Preparation Example 5-1, respectively, the same procedure as in Preparation Example 6-1 was repeated to afford the title compound. 0.71 g (95%).

$^1$H NMR (400 MHz, CDCl$_3$) δ 0.04 (s, 6H), 0.85 (s, 9H), 1.09 (m, 3H), 1.46 (s, 9H), 1.70~2.82 (m, 3H), 3.26~3.33 (m, 2H), 3.37 (s, 3H), 3.74 (m, 2H), 3.86~4.3 (m, 4H), 5.70~6.25 (m, 2H), 7.21~7.30 (m, 5H)

Preparation Example 6-6

(R)-t-butyl 2-((1R,2R)-1-methoxy-2-methyl-3-oxo-3-(phenethylamino)propyl)-4-oxopyrrolidine-1-carboxylate(X-6)

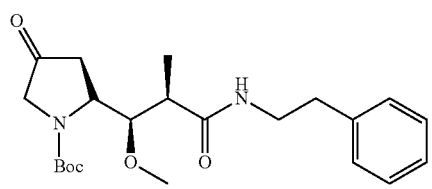

With the exception that (2R,3R)-3-((R)-1-(t-butoxycarbonyl)-4-oxopyrrolidin-2-yl)-3-methoxy-2-methylpropionic acid and 2-phenetamine were used instead of the compounds (VIII-2 and IX-1) obtained in Preparation Examples 4-2 and 5-1, respectively, the same procedure as in Preparation Example 6-1 was repeated to afford the title compound. 0.33 g (85%).

$^1$H NMR (400 MHz, CDCl$_3$): δ 1.08~1.17 (m, 3H), 1.20~1.27 (m, 2H), 1.57 (s, 9H), 1.73 (m, 1H), 1.99~2.06 (m, 1H), 2.39~2.56 (m, 2H), 2.79~2.88 (m, 2H), 3.34 (s, 3H), 3.47~3.67 (m, 2H), 3.72~3.97 (m, 3H), 4.31~4.41 (m, 1H), 5.67~5.81 (m, 2H), 7.06~7.43 (m, 5H)

Preparation Example 6-7

(2R,4R)-t-butyl 2-((1R,2R)-3-((2-(2-fluoro-4-methoxyphenyl)-2-oxoethyl)amino)-1-methoxy-2-methyl-3-oxopropyl)-4-methoxypyrrolidine-1-carboxylate (X-7)

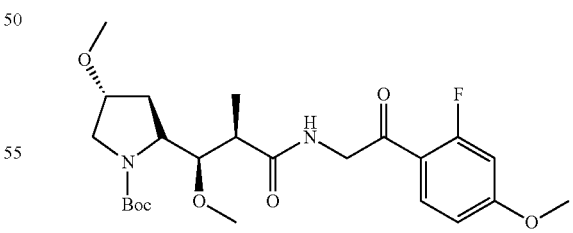

With the exception that the compound (IX-4) obtained in Preparation Example 5-4 was used instead of the compound (IX-1) obtained in Preparation Example 5-1, the same procedure as in Preparation Example 6-1 was repeated to afford the title compound. 0.87 g (93%).

$^1$H NMR (400 MHz, CDCl$_3$): δ 1.24 (m, 3H), 1.46 (s. 9H), 1.67~1.92 (m, 4H), 2.41~2.45 (m. 1H), 3.19~3.21 (m, 1H), 3.28 (s, 3H), 3.42 (s, 3H), 3.78 (m, 1H), 3.85 (s, 3H), 3.92 (m, 1H), 4.60 (s, 2H), 6.77 (m, 2H), 7.95 (m, 1H)

Preparation Example 6-8

(2S,4R)-t-butyl 4-methoxy-2-((1R,2R)-1-methoxy-2-methyl-3-oxo-3-((2-oxo-2-phenylethyl)amino)propyl)pyrrolidine-1-carboxylate(X-8)

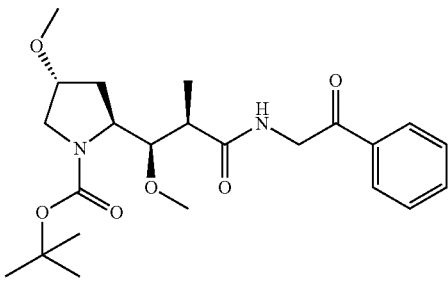 [SMILES: CO[C@@H]1C[C@@H]([C@H](OC)[C@@H](C)C(=O)NCC(=O)c2ccccc2)N(C(=O)OC(C)(C)C)C1]

With the exception that 2-amino-1-phenylethanone was used instead of the compound (IX-1) obtained in Preparation Example 5-1, the same procedure as in Preparation Example 6-1 was repeated to afford the title compound. 1.7 g (93%).

$^1$H NMR (400 MHz, CDCl$_3$): δ 1.27 (d, 3H), 1.49 (s, 9H), 1.68~1.73 (m, 1H), 1.82~1.95 (m, 3H), 2.5 (m, 1H), 3.21~3.27 (m, 1H), 3.29 (s, 3H), 3.38~3.65 (m, 1H), 3.48 (s, 3H), 3.82~3.99 (m, 2H), 4.7 (S, 2H), 7.5 (m, 2H), 7.61 (m, 1H), 7.97 (d, 1H)

Preparation Example 6-9

(2S,4R)-t-butyl 4-methoxy-2-((1R,2R)-1-methoxy-2-methyl-3-oxo-3-((2-oxo-2-(p-tolyl)ethyl)amino)propyl)pyrrolidine-1-carboxylate(X-9)

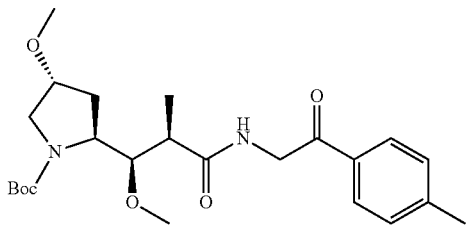 [SMILES: CO[C@@H]1C[C@@H]([C@H](OC)[C@@H](C)C(=O)NCC(=O)c2ccc(C)cc2)N(C(=O)OC(C)(C)C)C1]

With the exception that 2-amino-1-(p-tolyl)ethanone was used instead of the compound (IX-1) obtained in Preparation Example 5-1, the same procedure as in Preparation Example 6-1 was repeated to afford the title compound. 0.33 g (81%).

$^1$H NMR (400 MHz, CDCl$_3$): δ 1.25 (m, 3H), 1.47 (s. 9H), 1.71~1.95 (m, 4H), 2.43 (s. 3H), 2.47~2.55 (m. 1H), 3.21~3.27 (m, 1H), 3.39~3.42 (m, 1H), 3.48 (s, 3H), 3.81 (m, 1H), 3.92~3.96 (m, 1H), 4.73 (s, 2H), 7.30 (d, J=8.0 Hz, 2H), 7.88 (d, J=8.0 Hz, 2H)

Preparation Example 6-10

(2S,4R)-t-butyl 2-((1R,2R)-3-((2-(4-fluorophenyl)-2-oxoethyl)amino)-1-methoxy-2-methyl-3-oxopropyl)-4-methoxypyrrolidine-1-carboxylate(X-10)

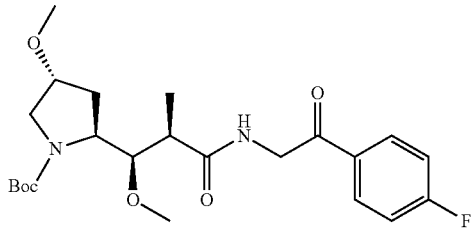 [SMILES: CO[C@@H]1C[C@@H]([C@H](OC)[C@@H](C)C(=O)NCC(=O)c2ccc(F)cc2)N(C(=O)OC(C)(C)C)C1]

With the exception that 2-amino-1-(4-fluorophenyl)ethanone was used instead of the compound (IX-1) obtained in Preparation Example 5-1, the same procedure as in Preparation Example 6-1 was repeated to afford the title compound. 0.56 g (81%).

$^1$H NMR (400 MHz, CDCl$_3$): δ 1.26~1.33 (m, 3H), 1.49 (s, 9H), 1.69~1.95 (m, 4H), 2.48~2.56 (m, 1H), 3.21~3.27 (m, 1H), 3.29 (s, 3H), 3.43~3.47 (m, 1H), 3.48 (s, 3H), 3.80~3.82 (m, 1H), 3.92~3.98 (m, 1H), 4.73 (s, 2H), 7.61 (m, 2H), 8.01~8.02 (m, 2H)

Preparation Example 6-11

(2R,4S)-t-butyl 4-methoxy-2-((1R,2R)-1-methoxy-2-methyl-3-oxo-3-(phenethylamino)propyl)pyrrolidine-1-carboxylate(X-11)

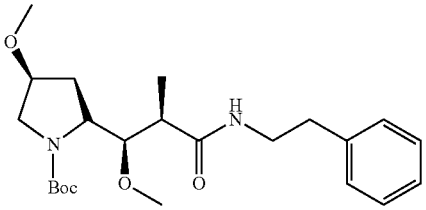

With the exception that (2R,3R)-3-((2R,4S)-1-(t-butoxycarbonyl)-4-methoxypyrrolidin-2-yl)-3-methoxy-2-methylpropionic acid and 2-phenetamine were used instead of the compound (VIII-2 and IX-1) obtained in Preparation Example 4-2, and 5-1, respectively, the same procedure as in Preparation Example 6-1 was repeated to afford the title compound. 0.26 g (61%).

$^1$H NMR (400 MHz, CDCl$_3$): δ 1.18 (d, 3H), 1.47 (s, 9H), 1.94~2.01 (m, 4H), 2.26~2.38 (m, 1H), 2.83 (t, 2H), 2.98 (m, 1H), 3.32 (s, 3H), 3.39 (s, 3H), 3.48~3.52 (m, 2H), 3.73~3.79 (m, 2H), 5.67~6.07 (m, 1H), 6.99~7.32 (m, 4H)

Preparation Example 6-12

(2S,4R)-t-butyl 2-((1R,2R)-3-((2-hydroxy-2-phenylethyl)amino)-1-methoxy-2-methyl-3-oxopropyl)-4-methoxypyrrolidine-1-carboxylate(X-12)

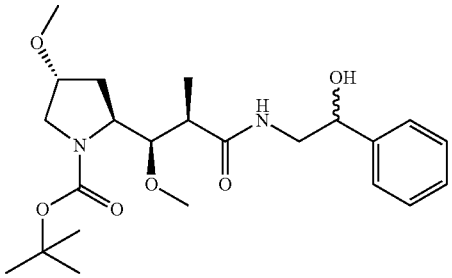 [SMILES: CO[C@@H]1C[C@@H]([C@H](OC)[C@@H](C)C(=O)NCC(O)c2ccccc2)N(C(=O)OC(C)(C)C)C1]

With the exception that 2-amino-1-phenylethanol was used instead of the compound (IX-1) obtained in Preparation Example 5-1, the same procedure as in Preparation Example 6-1 was repeated to afford the title compound. 0.43 g (100%).

¹H NMR (400 MHz, CDCl₃): δ 1.23~1.31 (m, 3H), 1.49 (s, 9H), 1.73~1.99 (m, 4H), 2.34~2.41 (m, 1H), 3.06~3.43 (m, 3H), 3.29 (s, 3H), 3.45 (s, 3H), 3.52~4.84 (m, 4H), 4.33~4.99 (m, 2H), 7.28~7.45 (m, 5H)

Preparation Example 6-13

(2S,4R)-t-butyl 2-(6R,9R,10R)-6,9-dimethyl-3,8-dioxo-1,5-diphenyl-2,11-dioxa-4,7-diazadodecan-10-yl)-4-methoxypyrrolidine-1-carboxylate(X-13)

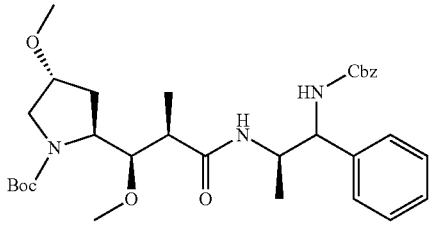 [SMILES: CO[C@@H]1C[C@@H]([C@H](OC)[C@@H](C)C(=O)N[C@H](C)C(NC(=O)OCc2ccccc2)c2ccccc2)N(C(=O)OC(C)(C)C)C1]

With the exception that the compound (IX-13) obtained in Preparation Example 5-13 was used instead of the compound (IX-1) obtained in Preparation Example 5-1, the same procedure as in Preparation Example 6-1 was repeated to afford the title compound. 68 mg (39%).

¹H NMR (400 MHz, CDCl₃): δ 0.98~1.28 (m, 7H), 1.43 (s, 9H), 1.71~2.29 (m, 4H), 3.21~3.30 (m, 2H), 3.27 (s, 3H), 3.38 (s, 3H), 3.72~3.75 (m, 2H), 4.33~4.69 (m, 1H), 5.0 (s, 2H), 5.82~6.13 (m, 1H), 6.46~7.0 (m, 1H), 7.21~7.40 (m, 10H)

Preparation Example 6-14

(2S,4R)-t-butyl 2-(6S,9R,10R)-6,9-dimethyl-3,8-dioxo-1,5-diphenyl-2,11-dioxa-4,7-diazadodecan-10-yl)-4-methoxypyrrolidine-1-carboxylate(X-14)

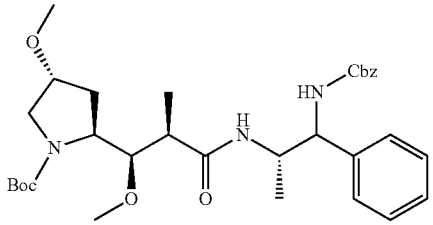 [SMILES: CO[C@@H]1C[C@@H]([C@H](OC)[C@@H](C)C(=O)N[C@@H](C)C(NC(=O)OCc2ccccc2)c2ccccc2)N(C(=O)OC(C)(C)C)C1]

With the exception that the compound (IX-15) obtained in Preparation Example 5-15 was used instead of the compound (IX-1) obtained in Preparation Example 5-1, the same procedure as in Preparation Example 6-1 was repeated to afford the title compound. 0.13 g (73%).

¹H NMR (400 MHz, CDCl₃): δ 0.98~1.26 (m, 7H), 1.40 (s, 9H), 1.71~2.29 (m, 4H), 3.20~3.26 (m, 2H), 3.29 (s, 3H), 3.37 (s, 3H), 3.46~3.72 (m, 2H), 4.28~4.43 (m, 1H), 5.0 (s, 2H), 5.82~6.13 (m, 1H), 6.46~7.0 (m, 1H), 7.21~7.40 (m, 10H)

Preparation Example 6-15

(2S,4R)-t-butyl 4-methoxy-2-((1R,2R)-1-methoxy-2-methyl-3-oxo-3-((2-(pyridin-2-yl)ethyl)amino)propyl)pyrrolidine-1-carboxylate(X-15)

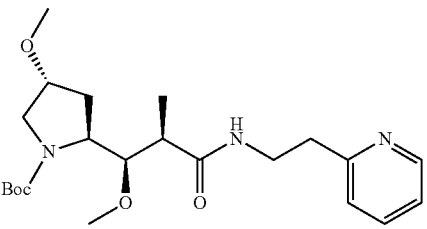 [SMILES: CO[C@@H]1C[C@@H]([C@H](OC)[C@@H](C)C(=O)NCCc2ccccn2)N(C(=O)OC(C)(C)C)C1]

With the exception that 2-(pyridin-2-yl)ethylamine was used instead of the compound (IX-1) obtained in Preparation Example 5-1, the same procedure as in Preparation Example 6-1 was repeated to afford the title compound. 0.5 g (64%).

¹H NMR (400 MHz, CDCl₃): δ 1.20 (s, 3H), 1.47 (d, J=6.8 Hz, 9H), 1.71 (m, 2H), 1.72 (m, 2H), 1.99 (s, 1.H), 2.31 (m, 1H), 3.00 (t, 2H), 3.21 (t, 1H), 3.27 (s, 3H), 3.39 (s, 3H), 3.53~3.84 (m, 4H), 7.16 (t, 2H), 7.61 (t, 1H), 8.52 (m, 1H)

Preparation Example 6-16

(2S,4R)-t-butyl 4-methoxy-2-((1R,2R)-1-methoxy-2-methyl-3-oxo-3-((2-(thiophen-2-yl)ethyl)amino)propyl)pyrrolidine-1-carboxylate(X-16)

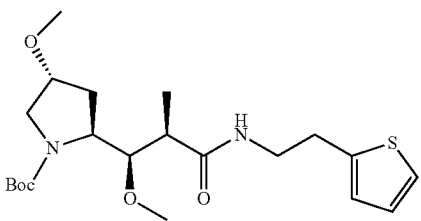 [SMILES: CO[C@@H]1C[C@@H]([C@H](OC)[C@@H](C)C(=O)NCCc2cccs2)N(C(=O)OC(C)(C)C)C1]

With the exception that 2-(thiophen-2-yl)ethylamine was used instead of the compound (IX-1) obtained in Preparation Example 5-1, the same procedure as in Preparation Example 6-1 was repeated to afford the title compound. 0.8 g (99%).

¹H NMR (400 MHz, CDCl₃): δ 1.21 (m, 3H), 1.48 (d, J=12.8 Hz, 9H), 1.74 (m, 2H), 1.88 (m, 2H), 2.28~2.38 (m, 1H), 3.05 (t, J=6.4 Hz, 2H), 3.21 (m, 1H), 3.25 (s, 3H), 3.39 (s, 3H), 3.53~3.57 (m, 2H), 3.74~3.86 (m, 2H), 6.85 (s, 1H), 6.94 (t, J=3.6 Hz, 1H), 7.15 (s, 1H)

Preparation Example 6-17

(2S,4R)-t-butyl 2-((1R,2R)-3-(((S)-1-(3,5-difluorophenyl)-1-oxopropan-2-yl)amino)-1-methoxy-2-methyl-3-oxopropyl)-4-methoxypyrrolidine-1-carboxylate(X-17)

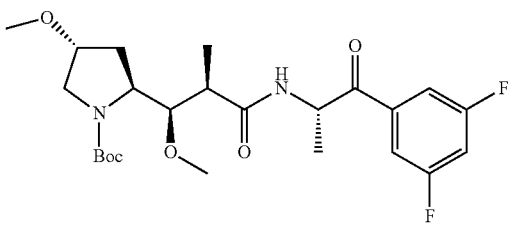 [SMILES: CO[C@@H]1C[C@@H]([C@H](OC)[C@@H](C)C(=O)N[C@@H](C)C(=O)c2cc(F)cc(F)c2)N(C(=O)OC(C)(C)C)C1]

To a solution of the compound (IX-7) (0.36 g, 1.26 mmol) obtained in Preparation Example 5-7 in 5 mL of dichloromethane was dropwise added 4 mL of trifluoroacetic acid while stirring at 20~25° C. for 3 hrs. After completion of the reaction, the reaction solvent was removed by vacuum concentration. Toluene was added twice in an amount of 5 mL to completely remove the trifluoroacetic acid before a reaction was continued.

The reaction concentrate (TFA salt) and the compound (VIII-2) (0.40 g, 1.26 mmol) obtained in Preparation Example 4-2 were dissolved in 5 mL of dimethylformamide. Diethyl cyanophosphonate (DEPC) (0.19 mL, 1.32 mmol) and triethylamine (0.89 mL, 6.30 mmol) were added at 0° C. to the solution that was then stirred at 20~25° C. for 16 hrs. When the reaction was completed, the reaction solvent was removed by vacuum concentration. The residue was dissolved in ethylacetate, and extracted with 1 M potassium hydrogen sulfite, water, a saturated sodium hydrogen carbonate solution, and brine, and the organic layer thus obtained was dried over anhydrous sodium sulfate, and concentrated in a vacuum. The concentrate was purified by column chromatography (ethylacetate:hexane=2:1→ethylacetate) to afford the title compound. 0.53 g (94%).

$^1$H NMR (400 MHz, CDCl$_3$): δ 1.19 (m, 3H), 1.38 (s, 9H), 1.52 (m, 3H), 1.85~1.91 (m, 5H), 2.92~2.94 (m. 2H), 3.30 (s, 6H), 3.61~3.67 (m, 4H), 5.27 (m, 1H), 6.86 (m, 1H), 7.32 (m, 2H), 8.03 (br, 1H)

Preparation Example 6-18

(2S,4R)-t-butyl 4-methoxy-2-((1R,2R)-1-methoxy-3-(((R)-1-(2-methoxyphenyl)-1-oxopropan-2-yl)amino)-2-methyl-3-oxopropyl)pyrrolidine-1-carboxylate(X-18)

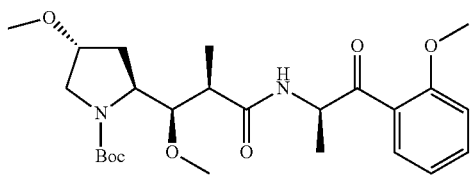

With the exception that compound (IX-6) obtained in Preparation Example 5-6 was used instead of the compound (IX-7) obtained in Preparation Example 5-7, the same procedure as in Preparation Example 6-17 was repeated to afford the title compound. 0.21 g (75%).

$^1$H NMR (400 MHz, CDCl$_3$): δ 1.26 (m, 3H), 1.34 (m, 3H), 1.49 (s, 9H), 1.71~2.45 (m, 4H), 3.25 (s. 3H), 3.33 (m, 1H), 3.47 (s, 3H), 3.71~3.89 (m, 2H), 3.94 (s, 3H), 4.05 (m, 1H), 5.55 (m, 1H), 6.82 (d, 1H), 7.03 (m, 2H), 7.52 (m, 1H), 7.76 (d, 1H)

Preparation Example 6-19

(2S,4R)-t-butyl 4-methoxy-2-((1R,2R)-1-methoxy-3-(((R)-1-(3-methoxyphenyl)-1-oxopropan-2-yl)amino)-2-methyl-3-oxopropyl)pyrrolidine-1-carboxylate(X-19)

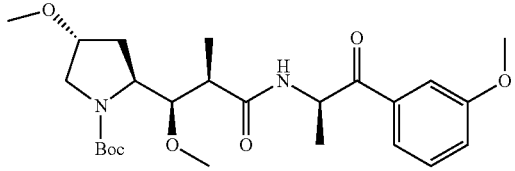

With the exception that (R)-t-butyl (1-(3-methoxyphenyl)-1-oxopropan-2-yl)carbamate was used instead of the compound (IX-7) obtained in Preparation Example 5-7, the same procedure as in Preparation Example 6-17 was repeated to afford the title compound. 0.18 g (64%).

$^1$H NMR (400 MHz, CDCl$_3$): δ 1.26 (m, 3H), 1.34 (m, 3H), 1.49 (s, 9H), 1.71~2.45 (m, 4H), 3.22 (s. 3H), 3.33 (m, 1H), 3.47 (s, 3H), 3.71-3.80 (m, 2H), 3.83 (s, 3H), 4.05 (m, 1H), 5.55 (m, 1H), 6.77 (d, 1H), 7.16 (m, 1H) 7.40 (m, 1H), 7.49 (m, 1H), 7.58 (d, 1H)

Preparation Example 6-20

(2S,4R)-t-butyl 4-methoxy-2-((1R,2R)-1-methoxy-3-(((R)-1-(4-methoxyphenyl)-1-oxopropan-2-yl)amino)-2-methyl-3-oxopropyl)pyrrolidine-1-carboxylate(X-20)

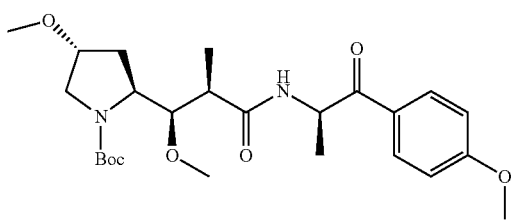

With the exception that the compound (IX-5) obtained in Preparation Example 5-5 was used instead of the compound (IX-7) obtained in Preparation Example 5-7, the same procedure as in Preparation Example 6-17 was repeated to afford the title compound. 0.23 g (82%).

$^1$H NMR (400 MHz, CDCl$_3$): δ 1.26 (m, 3H), 1.34 (m, 3H), 1.49 (s, 9H), 1.71~2.45 (m, 4H), 3.21 (s. 3H), 3.33 (m, 1H), 3.46 (s, 3H), 3.71~3.80 (m, 2H), 3.86 (s, 3H), 4.05 (m, 1H), 5.35 (m, 1H), 6.79 (d, 1H), 6.98 (m, 2H), 7.98 (m, 2H)

Preparation Example 6-21

(2S,4R)-t-butyl 2-((1R,2R)-3-(((R)-1-(2,6-difluorophenyl)-1-oxopropan-2-yl)amino)-1-methoxy-2-methyl-3-oxopropyl)-4-methoxypyrrolidine-1-carboxylate(X-21)

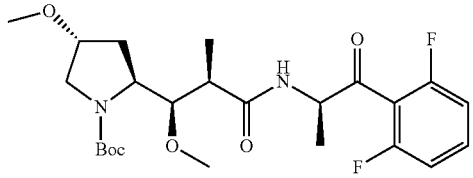 [SMILES: CO[C@@H]1C[C@@H]([C@H](OC)[C@@H](C)C(=O)N[C@H](C)C(=O)c2c(F)cccc2F)N(C(=O)OC(C)(C)C)C1]

With the exception that the compound (IX-8) obtained in Preparation Example 5-8 was used instead of the compound (IX-7) obtained in Preparation Example 5-7, the same procedure as in Preparation Example 6-17 was repeated to afford the title compound. 0.13 g (46%).

$^1$H NMR (400 MHz, CDCl$_3$): δ 1.26 (m, 3H), 1.34 (m, 3H), 1.49 (s, 9H), 1.71~2.45 (m, 4H), 3.21 (s. 3H), 3.33 (m, 1H), 3.46 (s, 3H), 3.71~3.80 (m, 2H), 4.05 (m, 1H), 5.35 (m, 1H), 6.79 (d, 1H), 7.09 (m, 2H), 7.46 (m, 1H)

Preparation Example 6-22

(2S,4R)-t-butyl 2-((1R,2R)-3-(((S)-1-(2,6-difluorophenyl)-1-oxopropan-2-yl)amino)-1-methoxy-2-methyl-3-oxopropyl)-4-methoxypyrrolidine-1-carboxylate(X-22)

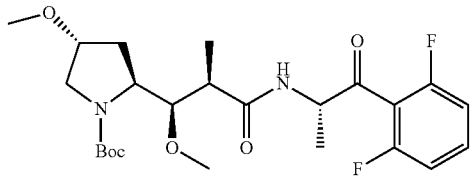 [SMILES: CO[C@@H]1C[C@@H]([C@H](OC)[C@@H](C)C(=O)N[C@@H](C)C(=O)c2c(F)cccc2F)N(C(=O)OC(C)(C)C)C1]

With the exception that the compound (IX-9) obtained in Preparation Example 5-0 was used instead of the compound (IX-7) obtained in Preparation Example 5-7, the same procedure as in Preparation Example 6-17 was repeated to afford the title compound. 0.13 g (46%).

$^1$H NMR (400 MHz, CDCl$_3$): δ 1.26 (m, 3H), 1.34 (m, 3H), 1.49 (s, 9H), 1.71~2.45 (m, 4H), 3.21 (s. 3H), 3.33 (m, 1H), 3.46 (s, 3H), 3.71~3.80 (m, 2H), 4.05 (m, 1H), 5.35 (m, 1H), 6.79 (d, 1H), 7.09 (m, 2H), 7.46 (m, 1H)

Preparation Example 6-23

(2S,4R)-t-butyl 2-((1R,2R)-3-(((R,E)-1-(hydroxyimino)-1-(3-methoxyphenyl)propan-2-yl)amino)-1-methoxy-2-methyl-3-oxopropyl)-4-methoxypyrrolidine-1-carboxylate(X-23)

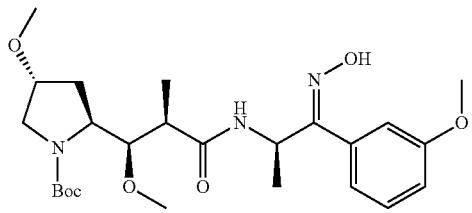 [SMILES: COc1cccc(/C(=N\O)[C@@H](C)NC(=O)[C@H](C)[C@@H](OC)[C@@H]2C[C@@H](OC)CN2C(=O)OC(C)(C)C)c1]

With the exception that the compound (IX-11) obtained in Preparation Example 5-11 was used instead of the compound (IX-7) obtained in Preparation Example 5-7, the same procedure as in Preparation Example 6-17 was repeated to afford the title compound. 0.23 g (52%).

$^1$H NMR (400 MHz, CDCl$_3$): δ 1.28 (m, 6H), 1.45 (m, 9H), 1.75 (m, 1H), 1.95 (m, 1H), 2.50 (m, 1H), 3.25 (m, 1H), 3.30 (s, 3H), 3.45 (s, 3H), 3.77 (s, 3H), 3.80-3.98 (m, 2H), 5.05 (m, 1H), 5.83 (m, 1H), 6.90 (m, 2H), 7.15 (m, 1H), 7.30 (m. 1H)

Preparation Example 6-24

(S)-t-butyl 4-((1R,2R)-3-((2,6-difluorophenethyl)amino)-1-methoxy-2-methyl-3-oxopropyl)thiazolidine-3-carboxylate (X-24)

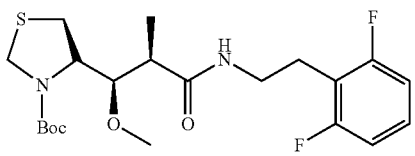

With the exception that the compound (VIII-4) obtained in Preparation Example 4-4 was used instead of the compound (VIII-2) obtained in Preparation Example 4-2, the same procedure as in Preparation Example 6-1 was repeated to afford the title compound. 0.32 g (64%).

$^1$H NMR (400 MHz, CDCl$_3$): δ 1.17~1.25 (d, 3H), 1.47 (s, 9H), 2.65~3.12 (m, 8H), 3.42 (S, 3H), 3.77~4.18 (m, 2H), 4.16~4.21 (m, 2H), 5.11 (br, 1H), 7.32 (m, 2H), 7.59 (m, 1H)

Preparation Example 6-25

(2S,4S)-t-butyl 2-((1R,2R)-3-((2,6-difluorophenethyl)amino)-1-methoxy-2-methyl-3-oxopropyl)-4-hydroxypyrrolidine-1-carboxylate(X-25)

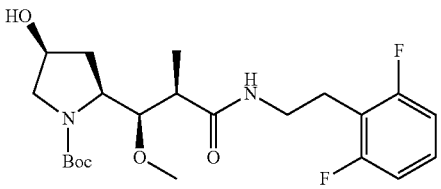 [SMILES: CO[C@H]([C@@H](C)C(=O)NCCc1c(F)cccc1F)[C@@H]1C[C@H](O)CN1C(=O)OC(C)(C)C]

With the exception that the compound (VIII-4) obtained in Preparation Example 4-4 was used instead of the compound (VIII-2) obtained in Preparation Example 4-2, the same procedure as in Preparation Example 6-1 was repeated to afford the title compound. 3.5 g (75%).

$^1$H NMR (400 MHz, CDCl$_3$): δ 1.26 (m, 3H), 1.48 (d, 9H), 1.62~1.66 (m, 2H), 1.81~1.89 (m, 1H), 2.07~2.14 (m, 1H), 2.22~2.36 (m, 1H), 2.87~2.92 (m, 2H), 3.36~3.41 (m, 2H), 3.52 (s, 6H), 3.81~3.91 (m, 1H), 3.98~4.00 (m, 1H), 4.11~4.13 (m, 1H), 4.62~4.64 (d, 1H), 5.59 (brs, 1H), 6.03 (brs, 1H), 6.87 (m, 2H), 7.18~7.19 (m, 1H)

Preparation Example 6-26

(2S,4S)-t-butyl 2-((1R,2R)-3-(((S)-1-(4-fluorophenyl)-1-oxopropan-2-yl)amino)-1-methoxy-2-methyl-3-oxopropyl)-4-hydroxypyrrolidine-1-carboxylate (X-26)

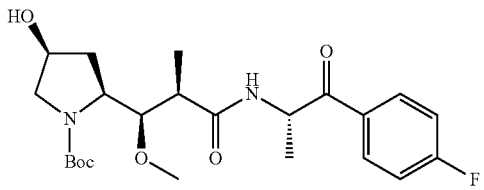 [SMILES: CO[C@H]([C@@H](C)C(=O)N[C@@H](C)C(=O)c1ccc(F)cc1)[C@@H]1C[C@H](O)CN1C(=O)OC(C)(C)C]

With the exception that the compounds (VIII-4) obtained in Preparation Example 4-4 and (S)-t-butyl (1-(4-fluorophenyl)-1-oxopropan-2-yl)carbamate were used instead of the compounds (VIII-2 and IX-7) obtained in Preparation Examples 4-2 and 5-7, respectively, the same procedure as in Preparation Example 6-17 was repeated to afford the title compound. 0.25 g (81%).

LC-MS m/z: [M+]$^+$

Preparation Example 6-27

(2S,4S)-t-butyl 4-azido-2-((1R,2R)-3-((2,6-difluorophenethyl)amino)-1-methoxy-2-methyl-3-oxopropyl)pyrrolidine-1-carboxylate(X-27)

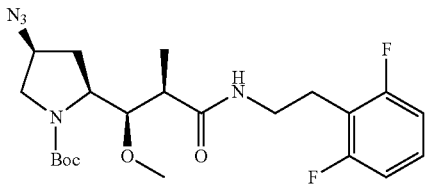 [SMILES: CO[C@H]([C@@H](C)C(=O)NCCc1c(F)cccc1F)[C@@H]1C[C@H](N=[N+]=[N-])CN1C(=O)OC(C)(C)C]

With the exception that the compound (VIII-5) obtained in Preparation Example 4-5 was used instead of the compound (VIII-2) obtained in Preparation Example 4-2, the same procedure as in Preparation Example 6-1 was repeated to afford the title compound. 5.9 g (94%).

$[\alpha]_D 25=-17.35°$ (c=1, MeOH)

$^1$H NMR (400 MHz, CDCl$_3$): δ 1.18 (d, 3H), 1.47 (s, 9H), 1.97~2.00 (m, 1H), 2.05~2.39 (m, 2H), 2.90~2.93 (t, 2H), 2.95~2.99 (m, 1H), 3.43 (s, 3H), 3.48~3.53 (m, 2H), 3.75~4.06 (m, 4H), 5.73 (brs, 1H), 6.08 (brs, 1H), 6.87 (t, 2H, J=7.6 Hz, 15.2 Hz), 7.15~7.21 (m, 1H)

Preparation Example 6-28

(2S,4S)-t-butyl 4-(benzyl(methyl)amino)-2-((1R,2R)-3-((2,6-difluorophenethyl)amino)-1-methoxy-2-methyl-3-oxopropyl)pyrrolidine-1-carboxylate(X-28)

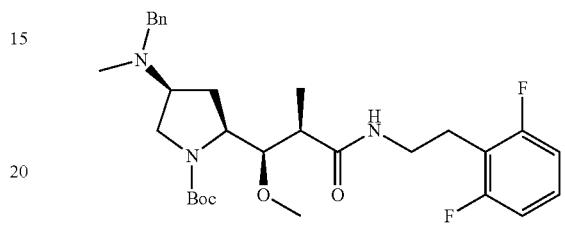

A solution of the compound (X-27) (5.37 g, 11.5 mmol) obtained in Preparation Example 6-27 in 100 mL of methanol was stirred for 16 hrs in the presence of 10% palladium carbon (0.5 g) in a hydrogen atmosphere. After completion of the reaction, the reaction mixture was filtered through celite, and the filtrate was washed several times with methanol. Removal of the solvent in a vacuum left (2S,4S)-t-butyl 4-amino-2-((1R,2R)-3-((2,6-difluorophenethyl)amino)-1-methoxy-2-methyl-3-oxopropyl)pyrrolidine-1-carboxylate 4.96 g (98%).

$[\alpha]_D 25=-39.65°$ (c=1, MeOH)

$^1$H NMR (400 MHz, CDCl$_3$): δ 1.17 (m, 3H), 1.47 (m, 9H), 1.88 (m, 2H), 2.94~2.00 (m, 1H), 2.10 (s, 3H), 2.23~2.45 (m, 1H), 2.76~2.78 (m, 1H), 2.89~2.92 (m, 2H), 2.98~3.03 (m, 1H), 3.44~3.55 (m, 1H), 3.47 (s, 3H), 3.78~4.05 (m, 3H), 5.80 (brs, 1H), 6.28 (brs, 1H), 6.84 (t, 2H, J=7.6 Hz, 15.2 Hz), 7.12~7.33 (m, 7H)

The residue was dissolved in 100 mL of methanol in an argon atmosphere. This solution was added with benzaldehyde (1.07 ml, 10.6 mmol) and stirred at 20~25° C. for 1 hr. Sodium cyanoborohydride (0.67 g, 10.6 mmol) was added to the solution that was then stirred for 16 hrs. Again, the resulting solution was mixed with paraformaldehyde (0.91 g, 10.1 mmol) while stirring for 2 hrs, and then with sodium cyanoborohydride (0.67 g, 10.6 mmol) while stirring for 4 hrs. When the reaction was completed, methanol was removed by vacuum concentration, and the residue was dissolved in 100 mL of ethylacetate, and washed with a saturated sodium hydrogen carbonate solution. The aqueous layer thus formed was extracted twice with ethylacetate. The organic layers were pooled, dried over anhydrous sodium sulfate, and concentrated in a vacuum to dryness. The residue was purified by column chromatography to afford the title compound. 2.74 g (50%).

LC-MS m/z: 545.7[M+H]$^+$ $^1$H NMR (400 MHz, CDCl$_3$): δ 1.19 (m, 3H), 1.51 (m, 9H), 1.88 (m, 2H), 2.94~2.00 (m, 1H), 2.21 (s, 3H), 2.27~2.41 (m, 1H), 2.76~2.78 (m, 1H), 2.89~2.92 (m, 2H), 2.98~3.03 (m, 1H), 3.44~3.55 (m, 1H), 3.47 (s, 3H), 3.78~4.05 (m, 3H), 5.8 (brs, 1H), 6.28 (brs, 1H), 7.12~7.19 (m, 1H), 7.22~7.25 (m, 1H)

EXAMPLES

Preparation of Compound of Chemical Formula I

Example 1

(S)—N-((3R,4S,5S)-1-((2R,4R)-2-((1R,2R)-3-((2,6-difluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-1)

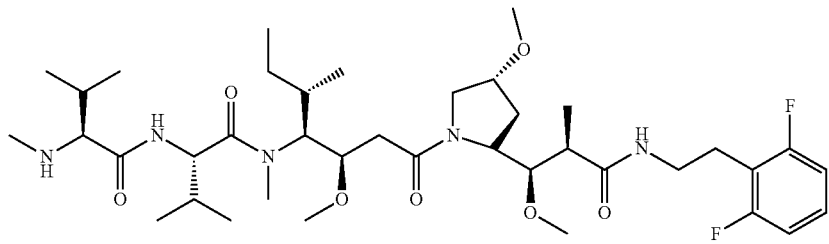

To a solution of the compound (X-1) (0.87 g, 2.04 mmol) obtained in Preparation Example 6-1 in 3 mL of dichloromethane was dropwise added 2 mL of trifluoroacetic acid, followed by stirring at 20~25° C. for 3 hrs. After completion of the reaction, the reaction solvent was removed by vacuum concentration. Toluene was added twice in an amount of 5 mL to completely remove the trifluoroacetic acid before a reaction was continued.

The reaction concentrate (TFA salt) and (5S,8S,11S,12R)-11-((S)-sec-butyl)-5,8-diisopropyl-12-methoxy-4,10-dimethyl-3,6,9-trioxo-1-phenyl-2-oxa-4,7,10-triazatetradecan-14-oic acid (compound II-1) (1.00 g, 2.04 mmol) were dissolved in 5 mL of dimethylformamide. Diethyl cyanophosphonate (DEPC) (0.34 mL, 2.05 mmol) and triethylamine (1.44 mL, 10.22 mmol) were added at 0° C. to the solution that was then stirred at room temperature for 16 hrs. When the reaction was completed, the reaction solvent was removed by vacuum concentration. The residue was dissolved in 20 mL of ethylacetate, and extracted with 1 M potassium hydrogen sulfite, water, a saturated sodium hydrogen carbonate solution, and brine, and the organic layer thus obtained was dried over anhydrous sodium sulfate, and concentrated in a vacuum. The concentrate was purified by column chromatography (ethylacetate:hexane=2:1→ethylacetate) to afford a compound in which the N-terminal amino group of compound (I-1) was protected, as a pale yellow oil. 1.29 g (74%).

$^1$H NMR (400 MHz, CDCl$_3$): δ 0.75~0.98 (m, 19H), 1.06 (m, 1H), 1.18~1.27 (m, 4H), 1.38 (m, 1H) 1.91~2.04 (m, 4H), 2.21~2.52 (m, 4H), 2.87~2.91 (m, 5H), 2.99 (m, 2H), 3.1 (s, 1H), 3.31 (s, 6H), 3.37 (s, 3H), 3.43~3.51 (m, 3H), 3.82 (dd, 1H), 4.09~4.15 (m, 2H), 4.68 (m, 1H), 5.12~5.23 (m, 2H), 6.52 (m, 1H), 6.82~6.87 (m, 2H), 7.13~7.17 (m, 1H), 7.30~7.34 (m, 5H)

The compound (1.29 g, 1.47 mmol) in which the N-terminal amino group of compound (I-1) was protected was dissolved in 9 mL of t-butylalcohol and 1 mL of water and reacted in the presence of 10% palladium carbon (0.1 g) in a hydrogen atmosphere for 3 hrs while stirring. After completion of the reaction, the reaction mixture was filtered through celite, and washed several times with methanol. Removal of the solvent in a vacuum left the title compound as a pale yellowish solid. 1.06 g (100%).

$^1$H NMR (400 MHz, CDCl$_3$): δ 0.78~0.98 (m, 20H), 1.06 (m, 1H), 1.16~1.27 (m, 4H), 1.38 (m, 1H) 1.65~1.76 (m, 7H), 1.89~2.02 (m, 5H), 2.31~2.38 (m, 5H), 2.71~2.75 (m, 1H), 2.88~2.89 (m, 2H) 3.00 (s, 2H), 3.10 (d, 1H), 3.29 (s, 6H), 3.35 (s, 3H), 3.41~3.48 (m, 3H), 3.79~3.82 (dd, 1H), 4.08~4.15 (m, 2H), 4.72~4.86 (m, 2H), 6.56 (m, 1H), 6.79~6.85 (m, 2H), 7.10~7.15 (m, 1H), 7.16~7.22 (m, 1H), 7.55 (d, 1H)

Example 2

(S)—N-((3R,4S,5S)-1-((2R,4R)-2-((1R,2R)-3-(3-fluorophenethyl)amino)-1-methoxy-2-methyl-3-oxo-propyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide
(I-2)

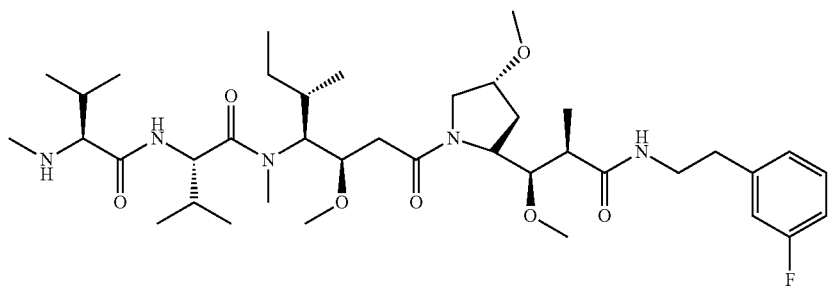

With the exception that the compound (X-3) obtained in Preparation Example 6-3 was used instead of the compound (X-1) obtained in Preparation Example 6-1, the same procedure as in Example 6-1 was repeated to afford a compound in which the N-terminal amino group of compound (I-2) was protected. 0.58 g (84%).

$^1$H NMR (400 MHz, CDCl$_3$): δ 0.78~0.99 (m, 19H), 1.06 (m, 1H), 1.19~1.25 (m, 4H), 1.34 (m, 1H) 1.67~1.74 (m, 4H), 2.16~2.38 (m, 4H), 2.83~2.91 (m, 5H), 3.00~3.12 (m, 2H) 3.10 (s, 1H), 3.29 (s, 3H), 3.31 (s, 3H), 3.38 (s, 3H), 3.44~3.51 (m, 3H), 3.82 (dd, 1H), 4.09~4.15 (m, 2H), 4.78 (m, 1H), 5.19~5.22 (m, 2H), 6.52 (m, 1H), 6.89~6.98 (m, 3H), 7.23 (m, 1H), 7.31~7.34 (m, 5H)

The title compound was prepared in the same manner as in Example 1, with the exception of using the compound in which the N-terminal amino group of compound (I-2) was protected. 0.48 g (100%).

$^1$H NMR (400 MHz, CDCl$_3$): δ 0.81~0.98 (m, 20H), 1.06 (m, 1H), 1.19~1.25 (m, 4H), 1.38 (m, 1H) 1.65~1.79 (m, 7H), 1.90~2.06 (m, 5H), 2.31~2.41 (m, 5H), 2.71~2.75 (m, 1H), 2.88~2.89 (m, 2H) 3.03 (s, 2H), 3.10 (d, 1H), 3.31 (s, 6H), 3.37 (s, 3H), 3.4~3.56 (m, 3H), 3.82~3.85 (dd, 1H), 4.02~4.13 (m, 2H), 4.75~4.79 (m, 2H), 6.64 (m, 1H), 6.93~7.02 (m, 2H), 7.12~7.18 (m, 2H)

Example 3

(S)—N-((3R,4S,5S)-1-((2R,4R)-2-((1R,2R)-3-((4-fluorophenethyl)amino)-1-methoxy-2-methyl-3-oxo-propyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide
(I-3)

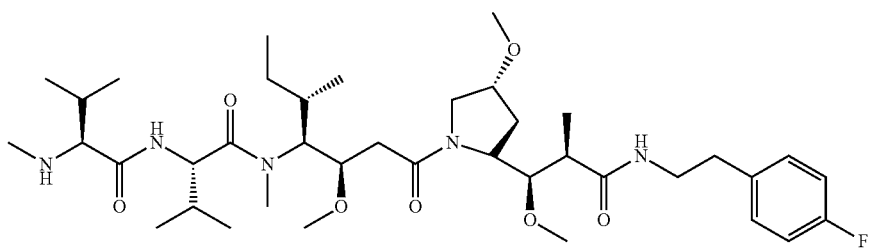

With the exception that the compound (X-4) obtained in Preparation Example 6-4 was used instead of the compound (X-1) obtained in Preparation Example 6-1, the same procedure as in Example 1 was repeated to afford a compound in which the N-terminal amino group of compound (I-3) was protected. 1.57 g (92%).

$^1$H NMR (400 MHz, CDCl$_3$): δ 0.78~0.99 (m, 19H), 1.06 (m, 1H), 1.19~1.27 (m, 4H), 1.38 (m, 1H) 1.91~2.04 (m, 4H), 2.17~2.38 (m, 4H), 2.77~2.91 (m, 5H), 3.00~3.12 (m, 2H) 3.10 (s, 1H), 3.29 (s, 3H), 3.31 (s, 3H), 3.38 (s, 3H), 3.44~3.51 (m, 3H), 3.82 (dd, 1H), 4.09~4.15 (m, 2H), 4.68 (m, 1H), 5.12~5.22 (m, 2H), 6.52 (m, 1H), 6.93~6.98 (m, 3H), 7.14~7.18 (m, 3H), 7.31~7.34 (m, 6H)

The title compound was prepared in the same manner as in Example 1, with the exception of using the compound in which the N-terminal amino group of compound (I-3) was protected. 0.60 g (100%).

$^1$H NMR (400 MHz, CDCl$_3$): δ 0.81~0.98 (m, 20H), 1.06 (m, 1H), 1.19~1.25 (m, 4H), 1.38 (m, 1H) 1.65~1.79 (m, 7H), 1.90~2.06 (m, 5H), 2.31~2.41 (m, 5H), 2.71~2.75 (m, 1H), 2.88~2.89 (m, 2H) 3.03 (s, 2H), 3.10 (d, 1H), 3.31 (s, 6H), 3.37 (s, 3H), 3.41~3.56 (m, 3H), 3.82~3.85 (dd, 1H), 4.02~4.13 (m, 2H), 4.75~4.79 (m, 2H), 6.64 (m, 1H), 6.86~7.00 (m, 3H), 7.57~7.60 (m, 1H)

Example 4

(S)—N-((3R,4S,5S)-1-((2R,4R)-2-((1R,2R)-3-(2,4-dichloro-5-fluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido) butanamide (I-4)

With the exception that the compound (X-2) obtained in Preparation Example 6-2 was used instead of the compound (X-1) obtained in Preparation Example 6-1, the same procedure as in Example 1 was repeated to afford a compound in which the N-terminal amino group of compound (I-4) was protected. 0.94 g (75%).

1H NMR (400 MHz, CDCl3): δ 0.68~0.97 (m, 19H), 1.07 (m, 1H), 1.18~1.25 (m, 4H), 1.34 (m, 1H) 1.70~1.78 (m, 4H), 1.91~2.04 (m, 3H), 2.21~2.42 (m, 3H), 2.87~2.91 (m, 5H), 3.27 (s, 3H), 3.31 (s, 3H), 3.38 (s, 3H), 3.44~3.51 (m, 3H), 3.82 (dd, 1H), 4.09~4.15 (m, 2H), 4.66~4.70 (m, 1H), 5.09~5.22 (m, 2H), 6.52 (m, 1H), 6.87 (m, 1H), 7.09~7.11 (m, 1H), 7.30~7.34 (m, 5H), 7.40~7.44 (m, 1H)

The title compound was prepared in the same manner as in Example 1, with the exception of using the compound in which the N-terminal amino group of compound (I-4) was protected. 0.70 g (92%).

$^1$H NMR (400 MHz, CDCl$_3$): δ 0.71~0.99 (m, 19H), 1.05 (m, 1H), 1.18~1.25 (m, 4H), 1.34 (m, 1H) 1.70~1.78 (m, 4H), 1.21~2.04 (m, 3H), 2.21~2.42 (m, 3H), 2.87~2.91 (m, 5H), 3.31 (s, 6H), 3.38 (s, 3H), 3.44~3.51 (m, 3H), 3.82 (dd, 1H), 4.09~4.15 (m, 2H), 4.68~4.72 (m, 1H), 5.09~5.22 (m, 2H), 6.52 (m, 1H), 6.90 (m, 1H), 7.09~7.11 (m, 1H), 7.30~7.34 (m, 5H), 7.40~7.44 (m, 1H)

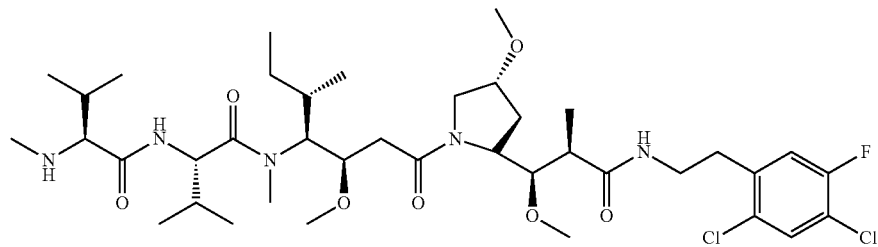

Example 5

(2S)—N-((3R,4S)-3-methoxy-1-((2R,4R)-4-methoxy-2-((1R,2R)-1-methoxy-3-((2-(4-methoxyphenyl)-2-oxoethyl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-5)

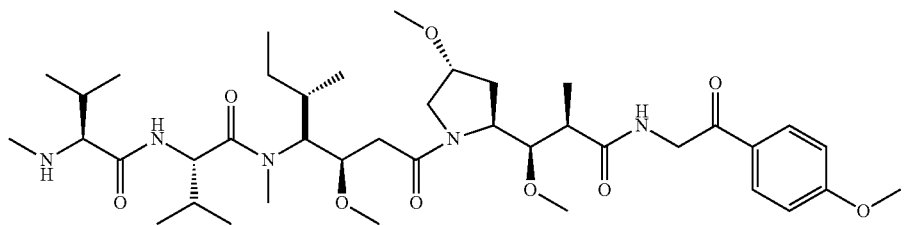

With the exception that (2S,4R)-t-butyl 4-methoxy-2-((1R,2R)-1-methoxy-3-((2-(4-methoxyphenyl)-2-oxoethyl)amino)-2-methyl-3-oxopropyl)pyrrolidine-1-carboxylate was used instead of the compound (X-1) obtained in Preparation Example 6-1, the same procedure as in Example 1 was repeated to afford a compound in which the N-terminal amino group of compound (I-5) was protected. 0.35 g (78%).

$^1$H NMR (400 MHz, CDCl$_3$): δ 0.71~0.88 (m, 12H), 0.95~1.07 (m, 1H), 0.96 (d, J=6.8 Hz, 3H), 1.26~1.33 (m, 1H), 1.32 (d, J=6.8 Hz, 3H), 1.62 (s, 3H), 1.67~1.86 (m, 2H), 2.00~2.08 (m, 3H), 2.24~2.32 (m, 2H), 2.41~2.47 (m, 2H), 2.59 (t, J=7.2 Hz, 1H), 2.87~2.99 (m, 4H), 3.08 (br, 1H), 3.24 (s, 3H), 3.28~3.55 (m, 2H), 3.33 (s, 1H), 3.46 (s, 3H), 3.89 (s, 3H), 3.99~4.11 (m, 2H), 4.13~4.15 (m, 2H), 4.24 (m, 1H), 4.67~4.71 (m, 4H), 5.09~5.23 (m, 3H), 6.49 (d, J=9.2 Hz, 2H), 6.96 (d, J=8.8 Hz, 2H), 7.09 (br, 1H), 7.21~7.34 (m, 5H), 7.95 (d, J=8.8 Hz, 2H)

The title compound was prepared in the same manner as in Example 1, with the exception of using the compound in which the N-terminal amino group of compound (I-5) was protected. 0.26 g (90%).

MALDI-TOF MS m/z: 731.8 [M+H]$^+$ $^1$H NMR (400 MHz, CDCl$_3$): δ 0.79~0.84 (m, 3H), 0.90~1.03 (m, 12H), 1.25~1.33 (m, 3H), 1.68~1.89 (m, 6H), 2.02~2.05 (m, 3H), 2.33 (s, 3H), 2.38~2.61 (m, 2H), 2.74 (d, J=5.2 Hz, 1H), 3.02~3.03 (m, 3H), 3.29 (s, 3H), 3.32~3.34 (m, 3H), 3.40~3.46 (m, 6H), 3.78 (s, 3H), 3.89 (s, 2H), 3.99~4.16 (m, 3H), 4.25 (br, 1H), 4.70~4.78 (m, 4H), 6.70 (m, 1H), 6.96 (d, J=8.8 Hz, 2H), 7.10 (br, 1H), 7.60 (m, 2H), 7.95 (d, J=8.8 Hz, 2H)

Example 6

(2 S)—N-((3R,4S)-3-methoxy-1-((2R,4R)-4-methoxy-2-((1R,2R)-1-methoxy-2-methyl-3-oxo-3-(((R)-1-oxo-1-phenylpropan-2-yl)amino)propyl)pyrrolidin-1-yl)-5-methyl-1-oxoheptan-4-yl)-N,3-dimethyl-2-((S)-3-methyl-2-(methylamino)butaneamido)butanamide (I-6)

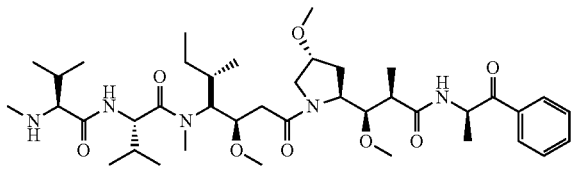 [SMILES: CC[C@H](C)[C@@H]([C@@H](CC(=O)N1C[C@H](OC)C[C@H]1[C@H](OC)[C@@H](C)C(=O)N[C@H](C)C(=O)c1ccccc1)OC)N(C)C(=O)[C@@H](NC(=O)[C@@H](NC)C(C)C)C(C)C]

With the exception that (2S,4R)-t-butyl 4-methoxy-2-((1R,2R)-1-methoxy-2-methyl-3-oxo-3-(((R)-1-oxo-1-phenylpropan-2-yl)amino)propyl)pyrrolidine-1-carboxylate was used instead of the compound (X-1) obtained in Preparation Example 6-1, the same procedure as in Example 1 was repeated to afford a compound in which the N-terminal amino group of compound (I-6) was protected. 0.27 g (88%).

ES-MS m/z: 850 [M+H]$^+$ $^1$H NMR (400 MHz, CDCl$_3$): δ 0.77~0.90 (m, 12H), 0.96 (d, J=7.2 Hz, 3H), 1.29 (d, J=7.2 Hz, 3H), 1.42 (d, J=7.2 Hz, 3H), 1.73~1.81 (m, 5H), 1.97~2.00 (m, 3H), 2.20~2.33 (m, 3H), 2.42~2.53 (m, 2H), 2.90 (s, 3H), 2.99 (s, 6H), 3.28 (s, 1H), 3.33 (s, 1H), 3.37~3.50 (m, 2H), 3.43 (s, 3H), 3.97 (dd, J=2.8, 7.2 Hz, 1H), 4.12~4.15 (m, 3H), 4.61~4.70 (m, 2H), 5.09~5.21 (m, 3H), 5.56 (t, J=7.2 Hz, 1H), 6.51 (br, J=8.8 Hz, 1H), 7.08 (br, J=7.2 Hz, 1H), 7.29~7.35 (m, 5H), 7.49 (t, J=7.2 Hz, 2H), 7.60 (t, J=7.2 Hz, 1H), 7.99 (d, J=7.2 Hz, 2H)

The title compound was prepared in the same manner as in Example 1, with the exception of using the compound in which the N-terminal amino group of compound (I-6) was protected. 0.22 g (98%).

MALDI-TOF MS m/z: 715.7 [M+H]+, 738.1 [M+Na]+

$^1$H NMR (400 MHz, CDCl$_3$): δ 0.81~1.04 (m, 9H), 0.94 (d, J=6.8 Hz, 3H), 0.99 (d, J=6.8 Hz, 3H), 1.18 (d, J=7.2 Hz, 3H), 1.20 (d, J=7.2 Hz, 3H), 1.34~1.42 (m, 1H), 1.68~1.86 (m, 5H), 1.91~2.09 (m, 5H), 2.31~2.49 (m, 4H), 2.33 (s, 3H), 2.74 (m, 1H), 3.04 (s, 3H), 3.31 (s, 6H), 3.36 (s, 3H), 3.41 (s, 1H), 3.43~3.53 (m, 1H), 3.73~3.93 (m, 2H), 4.08~4.19 (m, 2H), 4.65 (d, J=6.0 Hz, 1H), 4.73~4.86 (m, 2H), 6.92 (br, J=7.6 Hz, 1H), 7.21~7.40 (m, 5H), 7.59~7.62 (m, 1H)

Example 7

(2 S)—N-((3R,4S)-3-methoxy-1-((2S,4R)-4-methoxy-2-((1R,2R)-1-methoxy-2-methyl-3-oxo-3-(((S)-1-oxo-1-phenylpropan-2-yl)amino)propyl)pyrrolidin-1-yl)-5-methyl-1-oxoheptan-4-yl)-N,3-dimethyl-2-((S)-3-methyl-2-(methylamino)butaneamido) butanamide (I-7)

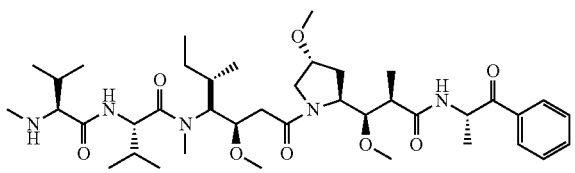 [SMILES: CC[C@H](C)[C@@H]([C@@H](CC(=O)N1C[C@H](OC)C[C@H]1[C@H](OC)[C@@H](C)C(=O)N[C@@H](C)C(=O)c1ccccc1)OC)N(C)C(=O)[C@@H](NC(=O)[C@@H](NC)C(C)C)C(C)C]

With the exception that (2S,4R)-t-butyl 4-methoxy-2-((1R,2R)-1-methoxy-2-methyl-3-oxo-3-(((S)-1-oxo-1-phenylpropan-2-yl)amino)propyl)pyrrolidine-1-carboxylate was used instead of the compound (X-1) obtained in Preparation Example 6-1, the same procedure as in Example 1 was repeated to afford a compound in which the N-terminal amino group of compound (I-7) was protected. 0.31 g (90%).

ES-MS m/z: 850 [M+H]+

$^1$H NMR (400 MHz, CDCl$_3$): δ 0.78~0.91 (m, 12H), 0.97 (d, J=6.8 Hz, 3H), 1.29 (d, J=6.8 Hz, 3H), 1.43 (d, J=7.2 Hz, 3H), 1.73~1.82 (m, 5H), 1.97~2.06 (m, 3H), 2.23~2.43 (m, 4H), 2.49 (t, J=7.2 Hz, 1H), 2.90 (s, 3H), 2.99 (s, 6H), 3.14 (s, 1H), 3.23~3.53 (m, 2H), 3.34 (s, 3H), 3.43 (s, 3H), 4.00 (dd, J=2.4, 7.2 Hz, 1H), 4.13~4.16 (m, 2H), 4.27~4.29 (m, 1H), 4.67~4.81 (m, 2H), 5.10~5.23 (m, 3H), 5.52 (t, J=7.2 Hz, 1H), 6.51 (br, J=8.8 Hz, 1H), 7.27~7.35 (m, 5H), 7.48 (t, J=7.2 Hz, 2H), 7.51~7.61 (m, 1H), 7.59 (t, J=7.2 Hz, 1H), 7.98 (d, J=7.2 Hz, 2H)

The title compound was prepared in the same manner as in Example 1, with the exception of using the compound in which the N-terminal amino group of compound (I-7) was protected. 0.24 g (93%).

MALDI-TOF MS m/z: 716.0 [M+H]+, 738.0 [M+Na]+

$^1$H NMR (400 MHz, CDCl$_3$): δ 0.82~1.01 (m, 12H), 1.14 (d, J=6.8 Hz, 3H), 1.26 (d, J=6.8 Hz, 3H), 1.30 (d, J=7.2 Hz, 3H), 1.98~2.12 (m, 3H), 2.33 (s, 3H), 2.34 (s, 3H), 2.36~2.50 (m, 2H), 2.73~2.76 (m, 2H), 3.01~3.04 (m, 3H), 3.32~3.54 (m, 2H), 3.30 (s, 6H), 3.39 (s, 3H), 3.45 (s, 3H), 3.81~3.85 (m, 2H), 4.07~4.08 (m, 2H), 4.32~4.48 (m, 2H), 4.58~4.60 (m, 1H), 4.73~4.79 (m, 2H), 6.35 (br, J=8.8 Hz, 1H), 6.64 (br, J=8.0 Hz, 1H), 7.21~7.44 (m, 6H), 7.56~7.60 (m, 1H)

Example 8

(S)-2-((S)-2-(dimethylamino)-3-methylbutaneamido)-N-((3R,4S,5S)-1-((2R,4R)-4-hydroxy-2-((1R,2R)-1-methoxy-2-methyl-3-oxo-3-(phenethylamino) propyl)pyrrolidin-1-yl)-3-methoxy-5-methyl-1-oxoheptan-4-yl)-N,3-dimethylbutanamide (I-8)

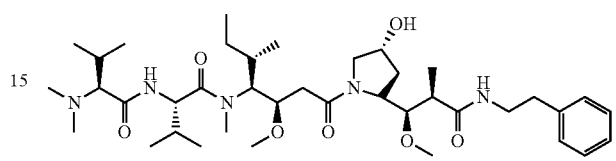

With the exception that the compound (X-5) obtained in Preparation Example 6-5 and (3R,4S,5S)-4-((S)-2-((S)-2-(dimethylamino)-3-methylbutaneamido)-N,3-dimethylbutaneamido)-3-methoxy-5-methylheptanic acid (compound II-2) were used instead of the compound (X-1) obtained in Preparation Example 6-1 and the compound (II-1), respectively, the same procedure as in Example 1 was repeated to afford a compound in which the hydroxy group of compound (I-8) was protected. 0.36 g (68%).

MALDI-TOF MS m/z: 832.9 [M+H]+

$^1$H NMR (400 MHz, CDCl$_3$): δ 0.04 (s, 6H), 0.92~1.05 (m, 20H), 1.09 (m, 3H), 1.46 (m, 4H), 1.62 (s, 2H), 1.97~2.17 (m, 3H), 2.44~2.46 (m, 3H), 2.71~2.80 (m, 3H), 2.81~2.89 (m, 1H), 2.91~2.94 (m, 2H), 2.71~2.80 (m, 3H) 3.04 (s, 3H), 3.05 (s, 3H), 3.26~3.33 (m, 2H), 3.37 (s, 3H), 3.74 (m, 2H), 3.86~4.30 (m, 4H), 5.70~6.25 (m, 2H), 7.21~7.30 (m, 5H)

The compound (0.07 g, 0.08 mmol) in which the hydroxy of the compound (I-8) was protected was dissolved in 6 mL of tetrahydrofuran, and reacted with 1.0 M tetrabutylammonium fluoride (0.3 mL, 0.25 mmol) for 5 hrs while stirring. The reaction was terminated with a saturated ammonium chloride solution, and the reaction mixture was extracted with 30 mL of ethylacetate and 20 mL of water, followed by vacuum concentration. The residue was purified by column chromatography (dichloromethane:methanol=9:1) to afford the title compound. 54 mg (90%).

$^1$H NMR (400 MHz, CDCl$_3$): δ 0.91~1.05 (m, 20H), 1.09 (m, 3H), 1.46 (m, 4H), 1.62 (s, 2H), 1.97~2.17 (m, 3H), 2.44~2.46 (m, 3H), 2.71~2.80 (m, 3H), 2.81~2.89 (m, 1H), 2.91~2.94 (m, 2H), 2.71~2.80 (m, 3H) 3.04 (s, 3H), 3.05 (s, 3H), 3.26~3.33 (m, 2H), 3.37 (s, 3H), 3.74 (m, 2H), 3.86~4.3 (m, 4H), 5.70~6.25 (m, 2H), 7.21~7.30 (m, 5H)

Example 9

(S)-2-((S)-2-(dimethylamino)-3-methylbutaneamido)-N-((3R,4S,5S)-3-methoxy-1-((R)-2-((1R,2R)-1-methoxy-2-methyl-3-oxo-3-(phenethylamino)propyl)-4-oxopyrrolidin-1-yl)-5-methyl-1-oxoheptan-4-yl)-N,3-dimethylbutanamide (I-9)

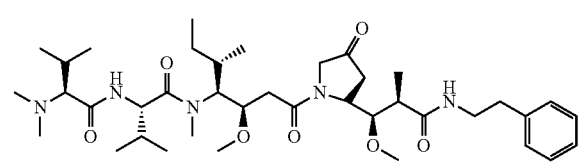

With the exception that the compound (X-6) obtained in Preparation Example 6-6 and compound (II-2) were used instead of the compound (X-1) obtained in Preparation Example 6-1 and the compound (II-1), respectively, the same procedure as in Example 1 was repeated to afford the title compound. 0.25 g (72%).

¹H NMR (400 MHz, CDCl₃): δ 0.80~0.88 (m, 3H), 0.92~1.05 (m, 15H), 1.09~1.25 (m, 4H), 1.60 (m, 3H), 1.99~2.17 (m, 4H), 2.24~2.37 (m, 6H), 2.43~2.50 (m, 5H), 2.81~2.84 (m, 2H), 3.04 (s, 3H), 3.28 (s, 3H), 3.38 (s, 3H), 3.53 (m, 3H), 3.73~4.3 (m, 4H), 4.71~4.79 (m, 2H), 5.70 (m, 1H), 7.18~7.36 (m, 5H)

Example 10

(S)-2-((S)-2-(dimethylamino)-3-methylbutaneamido)-N-((3R,4S,5S)-3-methoxy-1-((2R,4S)-4-methoxy-2-((1R,2R)-1-methoxy-2-methyl-3-oxo-3-(phenethylamino)propyl)pyrrolidin-1-yl)-5-methyl-1-oxoheptan-4-yl)-N,3-dimethylbutanamide (I-10)

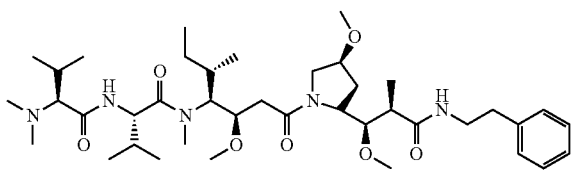

With the exception that the compound (X-11) obtained in Preparation Example 6-11 and compound (II-2) were used instead of the compound (X-1) obtained in Preparation Example 6-1 and the compound (II-2), respectively, the same procedure as in Example 1 was repeated to afford the title compound. 0.80 g (73%).

¹H NMR (400 MHz, CDCl₃): δ 0.80~0.83 (m, 3H), 0.92~1.02 (m, 16H), 1.18~1.22 (m, 4H), 1.83 (m, 3H), 2.07~2.17 (m, 4H), 2.24~2.37 (m, 6H), 2.43~2.50 (m, 4H), 2.81~2.88 (m, 2H), 3.02 (s, 3H), 3.27 (s, 3H), 3.38 (s, 3H), 3.49~3.53 (m, 3H), 3.87~4.22 (m, 4H), 4.76~4.79 (m, 1H), 6.40 (m, 1H), 7.18~7.38 (m, 5H)

Example 11

(S)—N-((3R,4S,5 S)-1-((2R,4R)-2-((1R,2R)-3-(((R)-1-(4-fluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-11)

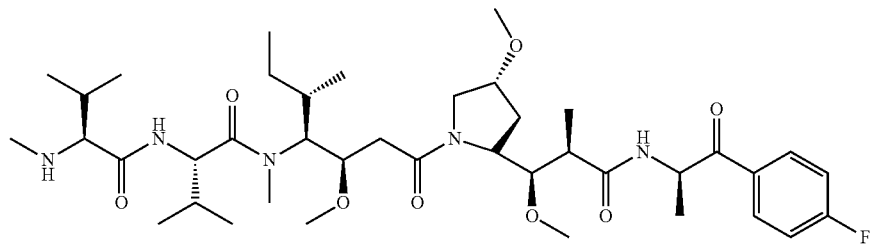

With the exception that (2R,4R)-t-butyl 2-((1R,2R)-3-(((R)-1-(4-fluorophenyl)-1-oxopropan-2-yl)amino)-1-methoxy-2-methyl-3-oxopropyl)-4-methoxypyrrolidine-1-carboxylate was used instead of the compound (X-1) obtained in Preparation Example 6-1, the same procedure as in Example 1 was repeated to afford a compound in which the N-terminal amino group of compound (I-11) was protected. 0.55 g (68%).

$^{1}$H NMR (400 MHz, CDCl$_3$): δ 0.71~1.03 (m, 20H), 1.22 (d, 3H), 1.33~1.37 (m, 4H), 1.40~1.44 (m, 3H), 1.60~1.81 (m, 4H), 1.98 (m, 2H), 2.26 (m, 2H), 2.90 (s, 3H), 3.21 (s, 3H), 3.32 (s, 3H), 3.43 (s, 3H), 4.06~4.15 (m, 2H), 4.22~4.27 (m, 2H), 4.64~4.69 (m, 2H), 5.09~5.13 (m, 2H), 5.23~5.30 (m, 2H), 5.50 (m, 1H), 7.18 (t, 2H), 7.34 (m, 5H), 8.01~8.05 (m, 2H)

The title compound was prepared in the same manner as in Example 1, with the exception of using the compound in which the N-terminal amino group of compound (I-11) was protected. 0.44 g (100%).

$^{1}$H NMR (400 MHz, CDCl$_3$): δ 0.71~1.03 (m, 20H), 1.22 (d, 3H), 1.33~1.37 (m, 4H), 1.40~1.44 (m, 3H), 1.60~1.81 (m, 4H), 1.98 (m, 2H), 2.26 (m, 2H), 2.90 (s, 3H), 3.21 (s, 3H), 3.32 (s, 3H), 3.43 (s, 3H), 4.06~4.15 (m, 2H), 4.22~4.27 (m, 2H), 4.64~4.69 (m, 2H), 5.09~5.13 (m, 2H), 5.23~5.30 (m, 2H), 5.50 (m, 1H), 7.18 (t, 2H), 8.01~8.05 (m, 2H)

Example 12

(S)—N-((3R,4S,5S)-1-((2R,4R)-2-((1R,2R)-3-(((S)-1-(4-fluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-12)

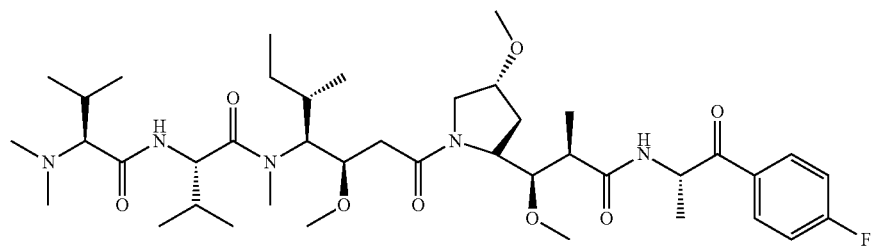

With the exception that (2R,4R)-t-butyl 2-((1R,2R)-3-(((S)-1-(4-fluorophenyl)-1-oxopropan-2-yl)amino)-1-methoxy-2-methyl-3-oxopropyl)-4-methoxypyrrolidine-1-carboxylate was used instead of the compound (X-1) obtained in Preparation Example 6-1, the same procedure as in Example 1 was repeated to afford a compound in which the N-terminal amino group of compound (I-12) was protected. 0.54 g (67%).

$^{1}$H NMR (400 MHz, CDCl$_3$): δ 0.71~1.03 (m, 20H), 1.22 (d, 3H), 1.33~1.37 (m, 4H), 1.40~1.44 (m, 3H), 1.60~1.81 (m, 4H), 1.98 (m, 2H), 2.26 (m, 2H), 2.90 (s, 3H), 3.21 (s, 3H), 3.32 (s, 3H), 3.43 (s, 3H), 4.06~4.15 (m, 2H), 4.22~4.27 (m, 2H), 4.64~4.69 (m, 2H), 5.09~5.13 (m, 2H), 5.23~5.30 (m, 2H), 5.50 (m, 1H), 7.18 (t, 2H), 7.34 (m, 5H), 8.01~8.05 (m, 2H)

The title compound was prepared in the same manner as in Example 1, with the exception of using the compound in which the N-terminal amino group of compound (I-12) was protected. 0.45 g (100%).

$^{1}$H NMR (400 MHz, CDCl$_3$): δ 0.71~1.03 (m, 20H), 1.22 (d, 3H), 1.33~1.37 (m, 4H), 1.40~1.44 (m, 3H), 1.60~1.81 (m, 4H), 1.98 (m, 2H), 2.26 (m, 2H), 2.90 (s, 3H), 3.21 (s, 3H), 3.32 (s, 3H), 3.43 (s, 3H), 4.06~4.15 (m, 2H), 4.22~4.27 (m, 2H), 4.64~4.69 (m, 2H), 5.09~5.13 (m, 2H), 5.23~5.30 (m, 2H), 5.50 (m, 1H), 7.18 (t, 2H), 8.01~8.05 (m, 2H)

Example 13

(S)—N-((3R,4S,5S)-3-methoxy-1-((2R,4R)-4-methoxy-2-((1R,2R)-1-methoxy-3-(((R)-1-(2-methoxyphenyl)-1-oxopropan-2-yl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-13)

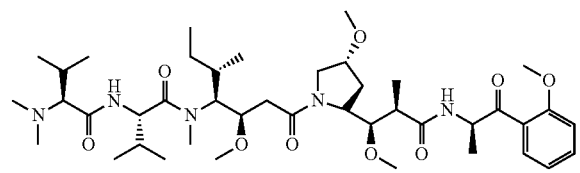

With the exception that the compound (X-18) obtained in Preparation Example 6-18 was used instead of the compound (X-1) obtained in Preparation Example 6-1, the same procedure as in Example 1 was repeated to afford a compound in which the N-terminal amino group of compound (I-13) was protected. 0.23 g (69%).

$^{1}$H NMR (400 MHz, CDCl$_3$): δ 0.78~0.99 (m, 19H), 1.29~1.42 (m, 6H), 1.69 (m, 6H), 1.95~2.04 (m, 2H), 2.21~2.43 (m, 3H), 2.55 (m, 1H), 2.90~3.00 (m, 6H), 3.21~3.42 (m, 7H), 3.55 (m, 1H), 3.86 (m, 2H), 4.01~4.26 (m, 3H), 4.66~4.69 (m, 2H), 5.12~5.22 (m, 2H), 5.52 (m, 1H), 6.54 (d, 1H), 7.02 (m, 2H), 7.34 (m, 5H), 7.52 (m, 1H), 7.75 (m, 1H)

The title compound was prepared in the same manner as in Example 1, with the exception of using the compound in which the N-terminal amino group of compound (I-13) was protected. 0.16 g (100%).

$^{1}$H NMR (400 MHz, CDCl$_3$): δ 0.78~0.99 (m, 19H), 1.29~1.42 (m, 6H), 1.69 (m, 6H), 1.95~2.04 (m, 2H), 2.21~2.43 (m, 3H), 2.55 (m, 1H), 2.90~3.00 (m, 6H), 3.21~3.42 (m, 7H), 3.55 (m, 1H), 3.86 (m, 2H), 4.01~4.26 (m, 3H), 4.66~4.69 (m, 2H), 5.12~5.22 (m, 2H), 5.52 (m, 1H), 6.54 (d, 1H), 7.52 (m, 2H), 7.75 (m, 1H)

Example 14

(S)—N-((3R,4S,5S)-3-methoxy-1-((2R,4R)-4-methoxy-2-((1R,2R)-1-methoxy-3-(((R)-1-(3-methoxyphenyl)-1-oxopropan-2-yl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-14)

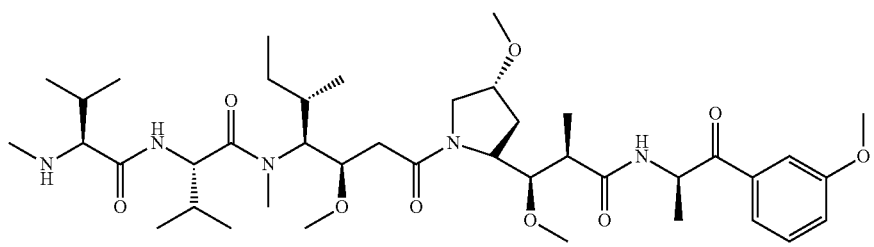

With the exception that the compound (X-19) obtained in Preparation Example 6-19 was used instead of the compound (X-1) obtained in Preparation Example 6-1, the same procedure as in Example 1 was repeated to afford a compound in which the N-terminal amino group of compound (I-14) was protected. 0.18 g (60%).

$^1$H NMR (400 MHz, CDCl$_3$): δ 0.78~0.99 (m, 19H), 1.29~1.42 (m, 6H), 1.69 (m, 6H), 1.95~2.04 (m, 2H), 2.21~2.43 (m, 3H), 2.55 (m, 1H), 2.90~3.00 (m, 6H), 3.21~3.42 (m, 7H), 3.55 (m, 1H), 3.86 (m, 2H), 4.01~4.26 (m, 3H), 4.66~4.69 (m, 2H), 5.12~5.22 (m, 2H), 5.52 (m, 1H), 6.54 (d, 1H), 7.16 (m, 1H), 7.34 (m, 5H)

The title compound was prepared in the same manner as in Example 1, with the exception of using the compound in which the N-terminal amino group of compound (I-14) was protected. 0.12 g (94%).

$^1$H NMR (400 MHz, CDCl$_3$): δ 0.78~0.99 (m, 19H), 1.29~1.42 (m, 6H), 1.69 (m, 6H), 1.95~2.04 (m, 2H), 2.21~2.43 (m, 3H), 2.55 (m, 1H), 2.90~3.00 (m, 6H), 3.21~3.42 (m, 7H), 3.55 (m, 1H), 3.86 (m, 2H), 4.01~4.26 (m, 3H), 4.66~4.69 (m, 2H), 5.12~5.22 (m, 2H), 5.52 (m, 1H), 6.54 (d, 2H), 7.16 (m, 2H)

Example 15

(S)—N-((3R,4S,5S)-3-methoxy-1-((2R,4R)-4-methoxy-2-((1R,2R)-1-methoxy-3-(((R)-1-(4-methoxyphenyl)-1-oxopropan-2-yl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-15)

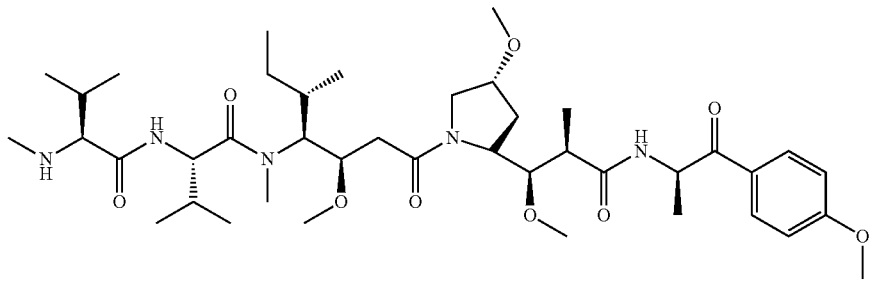

With the exception that the compound (X-20) obtained in Preparation Example 6-20 was used instead of the compound (X-1) obtained in Preparation Example 6-1, the same procedure as in Example 1 was repeated to afford a compound in which the N-terminal amino group of compound (I-15) was protected. 0.26 g (62%)

$^1$H NMR (400 MHz, CDCl$_3$): δ 0.73~0.81 (m, 19H), 0.90~0.96 (m, 6H), 1.25~1.30 (m, 3H), 1.34~1.42 (m, 7H), 1.95~2.04 (m, 2H), 2.21~2.43 (m, 3H), 2.55 (m, 1H), 2.90~3.00 (m, 6H), 3.21~3.42 (m, 7H), 3.55 (m, 1H), 3.86 (m, 2H), 4.01~4.26 (m, 3H), 4.66~4.69 (m, 2H), 5.12~5.22 (m, 2H), 5.52 (m, 1H), 6.54 (d, 1H), 6.95~7.05 (m, 3H), 7.30~7.34 (m, 5H), 7.95~7.98 (m, 2H)

The title compound was prepared in the same manner as in Example 1, with the exception of using the compound in which the N-terminal amino group of compound (I-15) was protected. 0.21 g (95%).

$^1$H NMR (400 MHz, CDCl$_3$): δ 0.73~0.81 (m, 19H), 0.90~0.96 (m, 6H), 1.25~1.30 (m, 3H), 1.34~1.42 (m, 7H), 1.95~2.04 (m, 2H), 2.21~2.43 (m, 3H), 2.55 (m, 1H), 2.90~3.00 (m, 6H), 3.21~3.42 (m, 7H), 3.55 (m, 1H), 3.86 (m, 2H), 4.01~4.26 (m, 3H), 4.66~4.69 (m, 2H), 5.12~5.22 (m, 2H), 5.52 (m, 1H), 6.54 (d, 2H), 7.95~7.98 (d, 2H)

Example 16

(S)—N-((3R,4S,5S)-1-((2R,4R)-2-((1R,2R)-3-(((S)-1-(3,5-difluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-16)

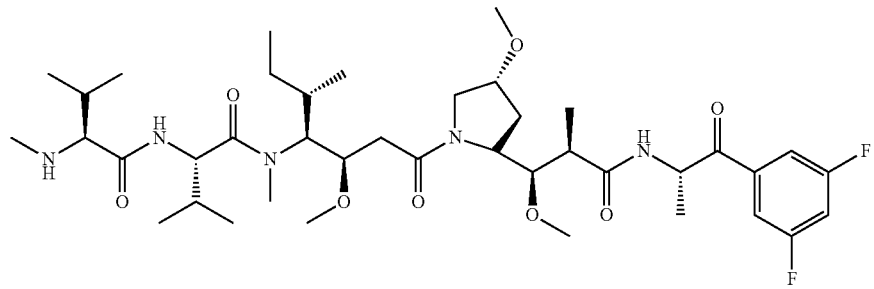

With the exception that the compound (X-17) obtained in Preparation Example 6-1 was used instead of the compound (X-1) obtained in Preparation Example 6-1, the same procedure as in Example 1 was repeated to afford a compound in which the N-terminal amino group of compound (I-16) was protected. 0.43 g (61%).

$^1$H NMR (400 MHz, CDCl$_3$): δ 0.79~1.02 (m, 20H), 1.29 (m, 3H), 1.34~1.44 (m, 4H), 2.21~2.43 (m, 4H), 2.77 (m, 2H), 3.00 (m, 2H), 3.29 (s, 3H), 3.34 (s, 3H), 3.42 (s, 3H), 3.61 (m, 1H), 3.99~4.14 (m, 3H), 4.15~4.37 (m, 3H), 4.70 (m, 1H), 5.21~5.23 (m, 2H), 5.36 (m, 1H), 7.03 (m, 1H), 7.18 (m, 1H), 7.34 (m, 5H), 7.49 (m, 1H)

The title compound was prepared in the same manner as in Example 1, with the exception of using the compound in which the N-terminal amino group of compound (I-16) was protected. 0.35 g (100%).

$^1$H NMR (400 MHz, CDCl$_3$): δ 0.79~1.02 (m, 20H), 1.29 (m, 3H), 1.34~1.44 (m, 4H), 2.21~2.43 (m, 4H), 2.77 (m, 2H), 3.00 (m, 2H), 3.29 (s, 3H), 3.34 (s, 3H), 3.42 (s, 3H), 3.61 (m, 1H), 3.99~4.14 (m, 3H), 4.15~4.37 (m, 3H), 4.70 (m, 1H), 5.21~5.23 (m, 2H), 5.36 (m, 1H), 7.03 (m, 1H), 7.49 (m, 2H)

Example 17

(S)—N-((3R,4S,5S)-1-((2R,4R)-2-((1R,2R)-3-(((S)-1-(2,6-difluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-17)

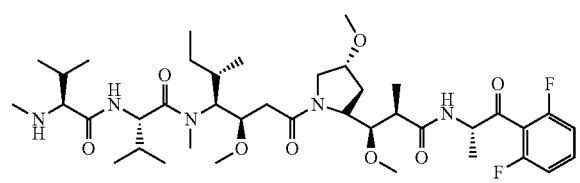

With the exception that the compound (X-22) obtained in Preparation Example 6-22 was used instead of the compound (X-1) obtained in Preparation Example 6-1, the same procedure as in Example 1 was repeated to afford a compound in which the N-terminal amino group of compound (I-17) was protected. 0.16 g (67%).

$^1$H NMR (400 MHz, CDCl$_3$): δ 0.81-0.98 (m, 20H), 1.29 (m, 3H), 1.34-1.44 (m, 4H), 2.21~2.43 (m, 4H), 2.77 (m, 2H), 3.00 (m, 2H), 3.29 (s, 3H), 3.34 (s, 3H), 3.42 (s, 3H), 3.61 (m, 1H), 3.99~4.14 (m, 3H), 4.15~4.37 (m, 3H), 4.70 (m, 1H), 5.21-5.23 (m, 2H), 5.36 (m, 1H), 7.03 (m, 1H), 7.18 (m, 1H), 7.35 (m, 5H), 7.49 (m, 1H)

The title compound was prepared in the same manner as in Example 1, with the exception of using the compound in which the N-terminal amino group of compound (I-17) was protected. 0.11 g (92%).

$^1$H NMR (400 MHz, CDCl$_3$): δ 0.81~0.98 (m, 20H), 1.29 (m, 3H), 1.34~1.44 (m, 4H), 2.21~2.43 (m, 4H), 2.77 (m, 2H), 3.00 (m, 2H), 3.29 (s, 3H), 3.34 (s, 3H), 3.42 (s, 3H), 3.61 (m, 1H), 3.99~4.14 (m, 3H), 4.15~4.37 (m, 3H), 4.70 (m, 1H), 5.21~5.23 (m, 2H), 5.36 (m, 1H), 7.03 (m, 1H), 7.18 (m, 1H), 7.49 (m, 1H)

Example 18

(S)—N-((3R,4S,5S)-1-((2R,4R)-2-((1R,2R)-3-(((R)-1-(2,6-difluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-18)

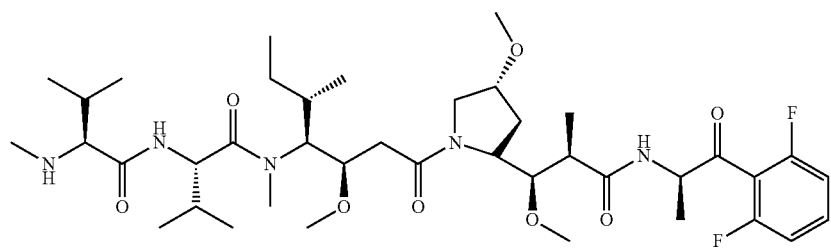

With the exception that the compound (X-21) obtained in Preparation Example 6-21 was used instead of the compound (X-1) obtained in Preparation Example 6-1, the same procedure as in Example 1 was repeated to afford a compound in which the N-terminal amino group of compound (I-18) was protected. 0.16 g (67%).

$^1$H NMR (400 MHz, CDCl$_3$): δ 0.81~0.98 (m, 20H), 1.29 (m, 3H), 1.34~1.44 (m, 4H), 2.21~2.43 (m, 4H), 2.77 (m, 2H), 3.00 (m, 2H), 3.29 (s, 3H), 3.34 (s, 3H), 3.42 (s, 3H), 3.61 (m, 1H), 3.99~4.14 (m, 3H), 4.15~4.37 (m, 3H), 4.70 (m, 1H), 5.21~5.23 (m, 2H), 5.36 (m, 1H), 7.03 (m, 1H), 7.18 (m, 1H), 7.35 (m, 5H), 7.49 (m, 1H)

The title compound was prepared in the same manner as in Example 1, with the exception of using the compound in which the N-terminal amino group of compound (I-18) was protected. 0.07 g (92%).

$^1$H NMR (400 MHz, CDCl$_3$): δ 0.81~0.98 (m, 20H), 1.29 (m, 3H), 1.34~1.44 (m, 4H), 2.21~2.43 (m, 4H), 2.77 (m, 2H), 3.00 (m, 2H), 3.29 (s, 3H), 3.34 (s, 3H), 3.42 (s, 3H), 3.61 (m, 1H), 3.99~4.14 (m, 3H), 4.15~4.37 (m, 3H), 4.70 (m, 1H), 5.21~5.23 (m, 2H), 5.36 (m, 1H), 7.03 (m, 1H), 7.18 (m, 1H), 7.49 (m, 1H)

Example 19

(S)—N-((3R,4S,5 S)-1-((2R,4R)-2-((1R,2R)-3-(((R,Z)-1-(hydroxyimino)-1-(3-methoxyphenyl)propan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-19)

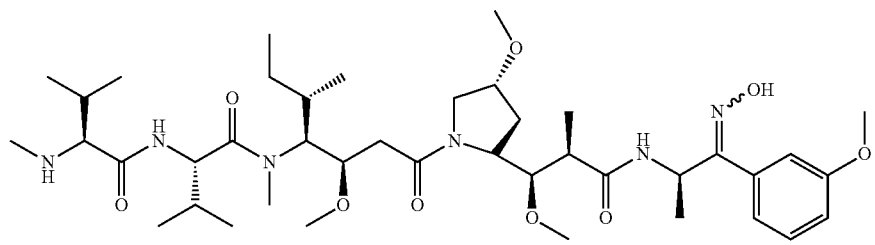

With the exception that the compound (X-23) obtained in Preparation Example 6-23 was used instead of the compound (X-1) obtained in Preparation Example 6-1, the same procedure as in Example 1 was repeated to afford a compound in which the N-terminal amino group of compound (I-19) was protected. 0.28 g (62%).

$^1$H NMR (400 MHz, CDCl$_3$): δ 0.79-0.98 (m, 20H), 1.01 (m, 4H), 1.19~1.27 (m, 4H), 2.21~2.43 (m, 4H), 2.77 (m, 2H), 3.00 (m, 2H), 3.29 (s, 6H), 3.34 (s, 3H), 3.42 (s, 3H), 3.61 (m, 1H), 3.99~4.14 (m, 3H), 4.15~4.37 (m, 3H), 4.70 (m, 1H), 5.21~5.23 (m, 2H), 5.36 (m, 1H), 7.03 (m, 1H), 7.15 (m, 2H), 7.30 (m. 1H), 7.35 (m, 5H), 7.49 (m, 1H)

The title compound was prepared in the same manner as in Example 1, with the exception of using the compound in which the N-terminal amino group of compound (I-19) was protected. 0.17 g (94%).

$^1$H NMR (400 MHz, CDCl$_3$): δ 0.79~0.98 (m, 20H), 1.01 (m, 4H), 1.19~1.27 (m, 4H), 2.21~2.43 (m, 4H), 2.77 (m, 2H), 3.00 (m, 2H), 3.29 (s, 6H), 3.34 (s, 3H), 3.42 (s, 3H), 3.61 (m, 1H), 3.99~4.14 (m, 3H), 4.15~4.37 (m, 3H), 4.70 (m, 1H), 5.21~5.23 (m, 2H), 5.36 (m, 1H), 7.03 (m, 1H), 7.15 (m, 2H), 7.49 (m, 1H)

Example 20

(S)-2-((S)-2-(dimethylamino)-3-methylbutaneamido)-N-((3R,4S,5S)-1-((2R,4R)-2-((1R,2R)-3-(((R)-1-(hydroxyimino)-1-(3-methoxyphenyl)propan-2-yl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-20)

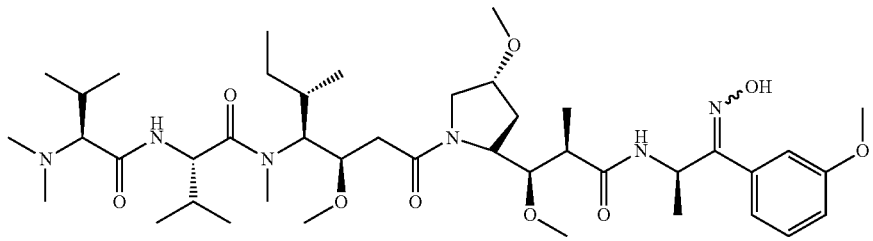

With the exception that the compound (X-23) obtained in Preparation Example 6-23 and the compound (II-2) were used instead of the compound (X-1) obtained in Preparation Example 6-1 and the compound (II-1), respectively, the same procedure as in Example 1 was repeated to afford the title compound. 0.23 g (58%).

$^1$H NMR (400 MHz, CDCl$_3$): δ 0.76~0.98 (m, 20H), 1.01~1.12 (m, 4H), 1.19~1.27 (m, 4H), 2.21~2.43 (m, 4H), 2.77 (m, 2H), 3.00 (m, 2H), 3.29 (s, 6H), 3.34 (s, 3H), 3.42 (s, 6H), 3.61 (m, 1H), 3.99~4.14 (m, 3H), 4.15~4.37 (m, 3H), 4.70 (m, 1H), 5.21~5.23 (m, 2H), 5.36 (m, 1H), 7.03 (m, 1H), 7.15 (m, 2H), 7.49 (m, 1H)

Example 21

(S)-2-((S)-2-(dimethylamino)-3-methylbutaneamido)-N-((3R,4S,5S)-1-((2R,4R)-2-((1R,2R)-3-(((R)-1-(4-fluorophenyl)-1-(hydroxyimino)propan-2-yl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-21)

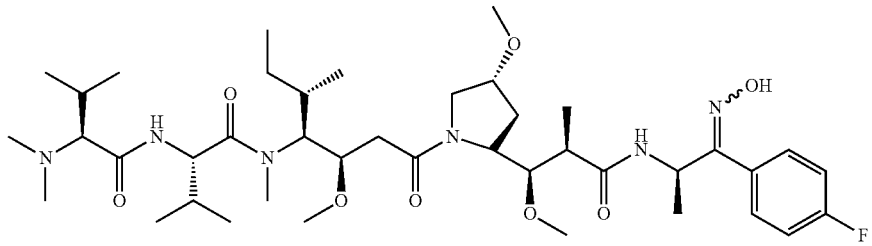

With the exception that (2R,4R)-t-butyl 2-((1R,2R)-3-(((R)-1-(4-fluorophenyl)-1-(hydroxyimino)propan-2-yl)amino)-1-methoxy-2-methyl-3-oxopropyl)-4-methoxypyrrolidine-1-carboxylate and the compound (II-2) were used instead of the compound (X-1) obtained in Preparation Example 6-1 and the compound (II-1), respectively, the same procedure as in Example 1 was repeated to afford the title compound. 0.17 g (63%).

$^1$H NMR (400 MHz, CDCl$_3$): δ 0.76~0.98 (m, 20H), 1.01~1.12 (m, 4H), 1.17~1.27 (m, 4H), 2.25~2.43 (m, 4H), 2.77 (m, 2H), 3.00 (m, 2H), 3.29 (s, 6H), 3.34 (s, 3H), 3.42 (s, 6H), 3.61 (m, 1H), 3.99~4.14 (m, 3H), 4.15~4.37 (m, 3H), 4.70 (m, 1H), 5.19~5.23 (m, 2H), 5.36 (m, 1H), 7.20 (t, 2H), 8.01~8.05 (m, 2H)

Example 22

(S)—N-((3R,4S,5S)-1-((2R,4R)-2-((1R,2R)-3-((2-(5-bromo-2-methylphenyl)-2-(hydroxyimino)ethyl)amino)-1-methoxy-2-methyl-3-oxopropyl)-4-methoxypyrrolidin-1-yl)-3-methoxy-5-methyl-1-oxoheptan-4-yl)-2-((S)-2-(dimethylamino)-3-methylbutaneamido)-N,3-dimethylbutanamide (I-22)

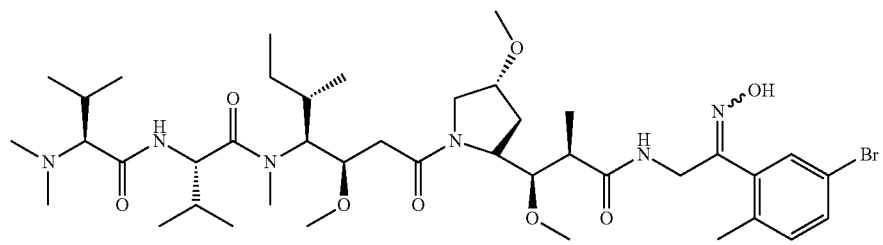

With the exception that (2R,4R)-t-butyl 2-((1R,2R)-3-((2-(5-bromo-2-methylphenyl)-2-(hydroxyimino)ethyl)amino)-1-methoxy-2-methyl-3-oxopropyl)-4-methoxypyrrolidine-1-carboxylate and the compound (II-2) were used instead of the compound (X-1) obtained in Preparation Example 6-1 and the compound (II-1), respectively, the same procedure as in Example 1 was repeated to afford the title compound. 35 mg (36%).

$^1$H NMR (400 MHz, CDCl$_3$): δ 0.73~0.97 (m, 20H), 1.01~1.12 (m, 4H), 1.19~1.23 (m, 4H), 2.28~2.42 (m, 4H), 2.52 (s, 3H), 2.77 (m, 2H), 3.03 (m, 2H), 3.30 (s, 6H), 3.34 (s, 3H), 3.42 (s, 6H), 3.59 (m, 1H), 3.01~4.14 (m, 3H), 4.17~4.37 (m, 3H), 4.70 (m, 1H), 5.19~5.23 (m, 2H), 5.36 (m, 1H), 7.15 (m, 1H), 7.65 (m, 2H)

Example 23

(S)-2-((S)-2-(dimethylamino)-3-methylbutaneamido)-N-((3R,4S,5S)-1-((2R,4R)-2-((1R,2R)-3-((2-(4-fluoro-2-methylphenyl)-2-(hydroxyimino)ethyl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-23)

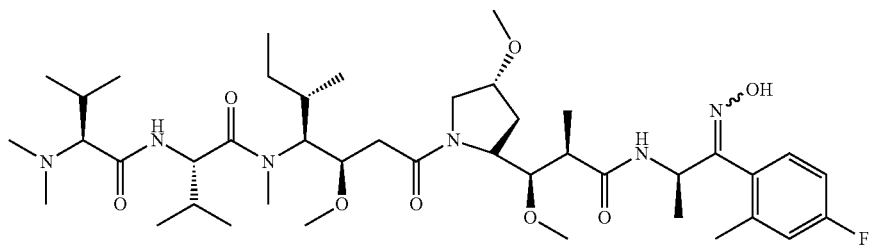

With the exception that (2R,4R)-t-butyl 2-((1R,2R)-3-((2-(4-fluoro-2-methylphenyl)-2-(hydroxyimino)ethyl)amino)-1-methoxy-2-methyl-3-oxopropyl)-4-methoxypyrrolidine-1-carboxylate and the compound (II-2) were used instead of the compound (X-1) obtained in Preparation Example 6-1 and the compound (II-1), respectively, the same procedure as in Example 1 was repeated to afford the title compound. 0.14 g (74%).

$^1$H NMR (400 MHz, CDCl$_3$): δ 0.76~0.95 (m, 20H), 1.01~1.12 (m, 4H), 1.17~1.23 (m, 4H), 2.25~2.42 (m, 4H), 2.48 (s, 3H), 2.77 (m, 2H), 3.00 (m, 2H), 3.29 (s, 6H), 3.34 (s, 3H), 3.42 (s, 6H), 3.59 (m, 1H), 3.01~4.14 (m, 3H), 4.17~4.37 (m, 3H), 4.70 (m, 1H), 5.19~5.23 (m, 2H), 5.36 (m, 1H), 7.20 (m, 1H), 7.71 (m, 2H)

Example 24

(S)—N-((3R,4S,5S)-1-((2R,4R)-2-((1R,2R)-3-((2-(4-fluoro-2-methylphenyl)-2-(hydroxyimino)ethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-24)

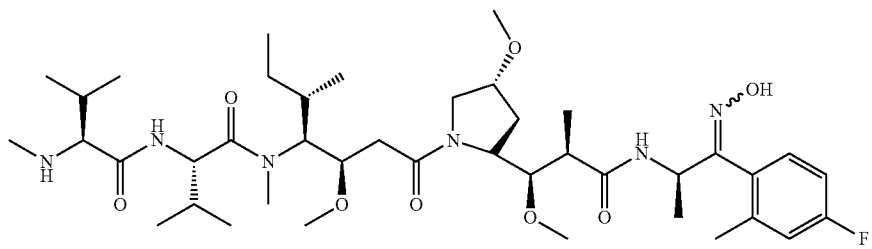

With the exception that (2R,4R)-t-butyl 2-((1R,2R)-3-((2-(4-fluoro-2-methylphenyl)-2-(hydroxyimino)ethyl)amino)-1-methoxy-2-methyl-3-oxopropyl)-4-methoxypyrrolidine-1-carboxylate was used instead of the compound (X-1) obtained in Preparation Example 6-1, the same procedure as in Example 1 was repeated to afford a compound in which the N-terminal amino group of compound (I-24) was protected. 0.23 g (77%).

$^1$H NMR (400 MHz, CDCl$_3$): δ 0.70~0.91 (m, 14H), 0.96~1.12 (m, 3H), 1.32 (d, J=6.8 Hz, 2H), 1.74~2.08 (m, 4H), 2.19~2.60 (m, 3H), 2.68 (s, 3H), 2.89~2.92 (m, 3H), 2.93~3.01 (m, 3H), 3.23 (s, 3H), 3.36 (s, 3H), 3.38~3.46 (m, 1H), 3.49 (s, 3H), 3.87 (s, 3H), 4.01 (dd, J=7.6 Hz, 2.4 Hz, 1H), 4.03~4.06 (m, 1H), 4.11~4.18 (m, 2H), 4.23-4.28 (m, 2H), 4.60~4.64 (m, 2H), 4.64~4.72 (m, 1H), 5.04~5.25 (m, 2H), 6.64 (dd, J=13.2 Hz, 2.0 Hz, 2H), 6.78 (dd, J=8.8 Hz, 2.4 Hz, 2H), 7.34 (m, 5H), 7.87~7.98 (m, 2H)

The title compound was prepared in the same manner as in Example 1, with the exception of using the compound in which the N-terminal amino group of compound (I-24) was protected. 0.18 g (91%).

MALDI-TOF MS m/z: 803 [M+23]$^+$ $^1$H NMR (400 MHz, CDCl$_3$): δ 0.73~0.92 (m, 20H), 1.01~1.12 (m, 4H), 1.17~1.23 (m, 4H), 2.25~2.42 (m, 4H), 2.48 (s, 3H), 2.77 (m, 2H), 3.00 (m, 2H), 3.29 (s, 6H), 3.34 (s, 3H), 3.42 (s, 3H), 3.59 (m, 1H), 3.01~4.14 (m, 3H), 4.17~4.37 (m, 3H), 4.70 (m, 1H), 5.19~5.23 (m, 2H), 5.36 (m, 1H), 7.20 (m, 1H), 7.71 (m, 2H)

Example 25

(S)—N-((3R,4S,5S)-1-((2S,4R)-2-((1R,2R)-3-(((E)-2-(2-fluoro-4-methoxyphenyl)-2-hydroxyimino)ethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-25)

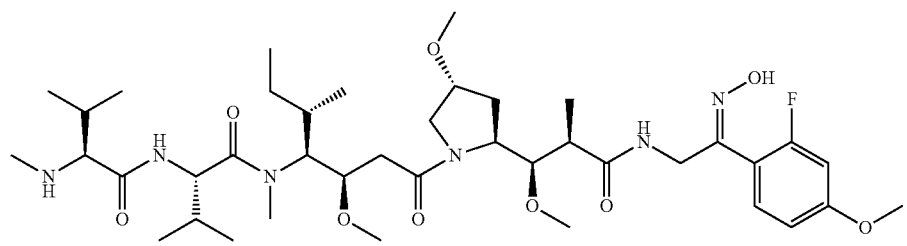

With the exception that (2S,4R)-t-butyl 2-((1R,2R)-3-(((E)-2-(2-fluoro-4-methoxyphenyl)-2-(hydroxyimino)ethyl)amino)-1-methoxy-2-methyl-3-oxopropyl)-4-methoxypyrrolidine-1-carboxylate was used instead of the compound (X-1) obtained in Preparation Example 6-1, the same procedure as in Example 1 was repeated to afford a compound in which the N-terminal amino group of compound (I-25) was protected. 0.35 g (65%).

$^1$H NMR (400 MHz, CDCl$_3$): δ 0.72~0.92 (m, 14H), 0.96 (d, J=6.4 Hz, 2H), 1.02 (d, J=6.8 Hz, 2H), 1.32 (d, J=6.8 Hz, 2H), 1.76~2.10 (m, 4H), 2.19~2.60 (m, 3H), 2.89~2.92 (m, 3H), 2.95~3.01 (m, 3H), 3.24 (s, 3H), 3.34 (s, 3H), 3.35~3.44 (m, 1H), 3.46 (s, 3H), 3.87 (s, 3H), 3.98 (dd, J=7.6 Hz, 2.4 Hz, 1H), 4.00~4.06 (m, 1H), 4.11~4.15 (m, 2H), 4.24~4.28 (m, 2H), 4.62~4.64 (m, 2H), 4.68~4.70 (m, 1H), 5.09~5.23 (m, 2H), 6.64 (dd, J=13.2 Hz, 2.0 Hz, 2H), 6.78 (dd, J=8.8 Hz, 2.4 Hz, 2H), 7.34 (m, 5H), 7.95 (t, J=8.4 Hz, 2H)

The title compound was prepared in the same manner as in Example 1, with the exception of using the compound in which the N-terminal amino group of compound (I-25) was protected. 0.15 g (96%).

$^1$H NMR (400 MHz, CDCl$_3$): δ 0.80~0.84 (m, 3H), 0.88~1.03 (m, 17H), 1.32 (d, J=7.2 Hz, 3H), 1.35~1.39 (m, 2H), 1.98~2.10 (m, 4H), 2.35 (s, 3H), 2.36~2.51 (m, 3H), 2.74 (m, 1H), 3.02 (m, 3H), 3.29 (s, 3H), 3.34 (s, 3H), 3.45 (s, 3H), 3.46~3.56 (m, 1H), 3.87 (s, 3H), 3.99 (dd, J=7.6 Hz, 2.8 Hz, 1H), 4.10~4.15 (m, 1H), 4.25~4.28 (m, 1H), 4.58~4.64 (m, 2H), 4.73~4.78 (m, 1H), 6.67 (m, 1H), 6.78 (qd, J=10.4 Hz, 2.8 Hz, 1H), 7.95 (m, 1H)

Example 26

(S)-2-((S)-2-(dimethylamino)-3-methylbutaneamido)-N-((3R,4S,5 S)-1-((2R,4R)-2-((1R,2R)-3-((2-(4-fluoro-2-methylphenyl)-2-(oxoethyl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-26)

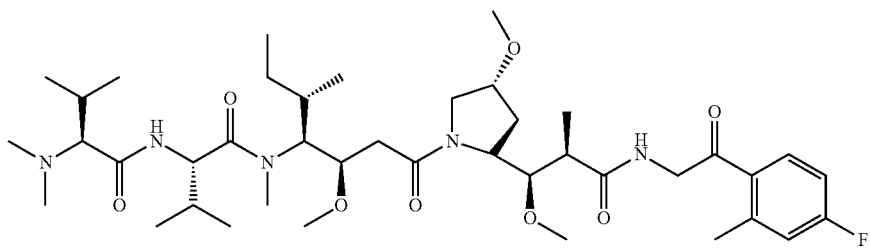

With the exception that (2R,4R)-t-butyl 2-((1R,2R)-3-((2-(4-fluoro-2-methylphenyl)-2-(oxoethyl)amino)-1-methoxy-2-methyl-3-oxopropyl)-4-methoxypyrrolidine-1-carboxylate and the compound (II-2) were used instead of the compound (X-1) obtained in Preparation Example 6-1 and the compound (II-1), respectively, the same procedure as in Example 1 was repeated to afford the title compound. 0.19 g (60%).

¹H NMR (400 MHz, CDCl₃): δ 0.76~0.95 (m, 20H), 1.01~1.12 (m, 4H), 1.17~1.23 (m, 4H), 2.25~2.42 (m, 4H), 2.44 (s, 3H), 2.73 (m, 2H), 3.00 (m, 2H), 3.29 (s, 6H), 3.34 (s, 3H), 3.42 (s, 6H), 3.59 (m, 1H), 3.01~4.14 (m, 3H), 4.17~4.37 (m, 3H), 4.70 (m, 1H), 5.17~5.21 (m, 2H), 5.36 (m, 1H), 7.21 (m, 1H), 7.75~7.81 (m, 2H)

Example 27

(S)—N-((3R,4S,5S)-1-((2R,4R)-2-((1R,2R)-3-((2-(4-fluoro-2-methylphenyl)-2-(oxoethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-27)

1 was repeated to afford a compound in which the N-terminal amino group of compound (I-27) was protected. 0.51 g (68%).

¹H NMR (400 MHz, CDCl₃): δ 0.70~0.91 (m, 14H), 0.96~1.12 (m, 3H), 1.32 (d, J=6.8 Hz, 2H), 1.74~2.08 (m, 4H), 2.19~2.60 (m, 3H), 2.68 (s, 3H), 2.89~2.92 (m, 3H), 2.93~3.01 (m, 3H), 3.23 (s, 3H), 3.36 (s, 3H), 3.38~3.46 (m, 1H), 3.49 (s, 3H), 3.87 (s, 3H), 4.01 (dd, J=7.6 Hz, 2.4 Hz, 1H), 4.03~4.06 (m, 1H), 4.11~4.18 (m, 2H), 4.23~4.28 (m, 2H), 4.60~4.64 (m, 2H), 4.64~4.72 (m, 1H), 5.04~5.25 (m, 2H), 6.64 (dd, J=13.2 Hz, 2.0 Hz, 2H), 6.78 (dd, J=8.8 Hz, 2.4 Hz, 2H), 7.34 (m, 5H), 7.87~7.98 (m, 2H)

The title compound was prepared in the same manner as in Example 1, with the exception of using the compound in which the N-terminal amino group of compound (I-27) was protected. 0.39 g (93%).

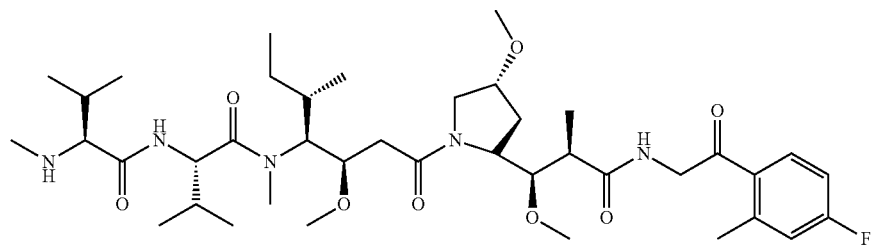

With the exception that (2R,4R)-t-butyl 2-((1R,2R)-3-((2-(4-fluoro-2-methylphenyl)-2-(oxoethyl)amino)-1-methoxy-2-methyl-3-oxopropyl)-4-methoxypyrrolidine-1-carboxylate was used instead of the compound (X-1) obtained in Preparation Example 6-1, the same procedure as in Example MALDI-TOF MS m/z: 765 [M+1]⁺

¹H NMR (400 MHz, CDCl₃): δ 0.73~0.92 (m, 20H), 1.01~1.12 (m, 4H), 1.17~1.21 (m, 4H), 2.23~2.41 (m, 4H), 2.45 (s, 3H), 2.77 (m, 2H), 3.02 (m, 2H), 3.29 (s, 6H), 3.34 (s, 3H), 3.41 (s, 3H), 3.59 (m, 1H), 3.01~4.14 (m, 3H), 4.17~4.37 (m, 3H), 4.70 (m, 1H), 5.19~5.23 (m, 2H), 5.36 (m, 1H), 7.25 (m, 1H), 7.73~7.89 (m, 2H)

Example 28

(S)—N-((3R,4S,5S)-3-methoxy-1-((2S,4R)-4-methoxy-2-((1R,2R)-1-methoxy-2-methyl-3-oxo-3-((2-oxo-2-(o-tolyl)ethyl)amino)propyl)pyrrolidin-1-yl)-5-methyl-1-oxoheptan-4-yl)-N,3-dimethyl-2-((S)-3-methyl-2-(methylamino)butaneamido)butanamide (I-28)

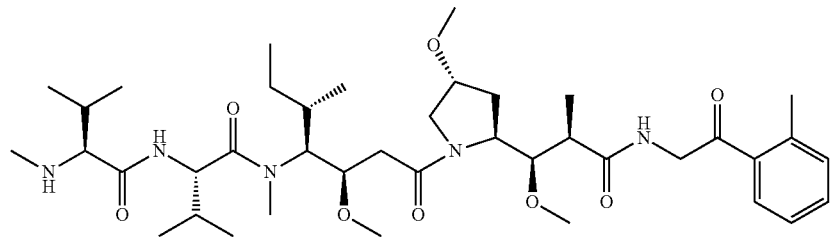 [SMILES: CC[C@H](C)[C@@H]([C@@H](CC(=O)N1C[C@H](OC)C[C@H]1[C@H](OC)[C@@H](C)C(=O)NCC(=O)c1ccccc1C)OC)N(C)C(=O)[C@@H](NC(=O)[C@@H](NC)C(C)C)C(C)C]

With the exception that (2S,4R)-t-butyl 4-methoxy-2-((1R,2R)-1-methoxy-2-methyl-3-oxo-3-((2-oxo-2-(o-tolyl)ethyl)amino)propyl)pyrrolidine-1-carboxylate was used instead of the compound (X-1) obtained in Preparation Example 6-1, the same procedure as in Example 1 was repeated to afford a compound in which the N-terminal amino group of compound (I-28) was protected. 0.15 g (24%).

$^1$H NMR (400 MHz, CDCl$_3$): δ 0.76~0.86 (m, 11H), 0.87 (d, J=6.8 Hz, 6H), 0.96 (d, J=6.8 Hz, 3H), 1.33 (d, J=4.8 Hz, 2H), 1.72~2.01 (m, 4H), 2.22~2.60 (m, 3H), 2.43 (s, 3H), 2.89~2.93 (m, 3H), 2.95~3.01 (m, 3H), 3.27 (s, 3H), 3.33 (s, 3H), 3.35~3.41 (m, 1H), 3.46 (s, 3H), 4.01~4.17 (m, 3H), 4.23~4.25 (m, 2H), 4.67~4.69 (m, 2H), 4.72~4.74 (m, 2H), 5.12~5.22 (m, 2H), 7.27 (d, J=8.4 Hz, 2H), 7.29~7.34 (m, 5H), 7.85~7.94 (m, 2H)

The title compound was prepared in the same manner as in Example 1, with the exception of using the compound in which the N-terminal amino group of compound (I-28) was protected. 60 mg (46%).

MALDI-TOF MS m/z: 747 [M+1]$^+$ $^1$H NMR (400 MHz, CDCl$_3$): δ 0.81~0.85 (m, 3H), 0.92~1.03 (m, 17H), 1.26~1.29 (m, 3H), 1.31~1.44 (m, 2H), 1.96~2.08 (m, 4H), 2.35 (s, 6H), 2.38~2.53 (m, 3H), 2.77 (d, J=4.8 Hz, 1H), 3.03 (m, 3H), 3.29 (s, 3H), 3.33 (s, 3H), 3.34~3.40 (m, 1H), 3.44 (d, J=8.4 Hz, 3H), 3.45~3.55 (m, 1H), 3.80~3.84 (m, 1H), 3.89~3.98 (m, 1H), 4.07 (m, 2H), 4.75~4.79 (m, 2H), 4.85~4.91 (m, 1H), 7.09~7.16 (m, 2H), 7.31~7.38 (m, 2H)

Example 29

(S)—N-((3R,4S,5S)-3-methoxy-1-((2S,4R)-4-methoxy-2-((1R,2R)-1-methoxy-2-methyl-3-oxo-3-((2-oxo-2-(p-tolyl)ethyl)amino)propyl)pyrrolidin-1-yl)-5-methyl-1-oxoheptan-4-yl)-N,3-dimethyl-2-((S)-3-methyl-2-(methylamino)butaneamido)butanamide (I-29)

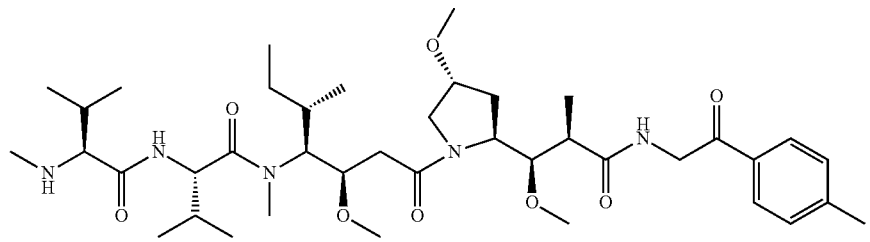

With the exception that the compound (X-9) obtained in Preparation Example 6-9 was used instead of the compound (X-1) obtained in Preparation Example 6-1, the same procedure as in Example 1 was repeated to afford a compound in which the N-terminal amino group of compound (I-29) was protected. 0.24 g (95%).

$^1$H NMR (400 MHz, CDCl$_3$): δ 0.76-0.86 (m, 11H), 0.87 (d, J=6.8 Hz, 6H), 0.96 (d, J=6.8 Hz, 3H), 1.33 (d, J=4.8 Hz, 2H), 1.74~2.03 (m, 4H), 2.20~2.61 (m, 3H), 2.43 (s, 3H), 2.89~2.93 (m, 3H), 2.95~3.01 (m, 3H), 3.27 (s, 3H), 3.33 (s, 3H), 3.35~3.44 (m, 1H), 3.46 (s, 3H), 4.00 (dd, J=7.5 Hz, 2.8 Hz, 1H), 4.12~4.15 (m, 2H), 4.23~4.25 (m, 2H), 4.67~4.69 (m, 2H), 4.72~4.74 (m, 2H), 5.12~5.22 (m, 2H), 7.27 (d, J=8.4 Hz, 2H), 7.29~7.34 (m, 5H), 7.87 (d, J=8.4 Hz, 2H)

The title compound was prepared in the same manner as in Example 1, with the exception of using the compound in which the N-terminal amino group of compound (I-29) was protected. 0.19 g (95%).

$^1$H NMR (400 MHz, CDCl$_3$): δ 0.81~0.85 (m, 3H), 0.92~1.03 (m, 17H), 1.26~1.29 (m, 3H), 1.31~1.44 (m, 2H), 1.96~2.10 (m, 4H), 2.33 (s, 6H), 2.37~2.51 (m, 3H), 2.74 (d, J=4.8 Hz, 1H), 3.03 (m, 3H), 3.29 (s, 3H), 3.33 (s, 3H), 3.34~3.40 (m, 1H), 3.42 (d, J=8.4 Hz, 3H), 3.47~3.56 (m, 1H), 3.80~3.84 (m, 1H), 3.91~3.98 (m, 1H), 4.07 (m, 2H), 4.75~4.79 (m, 2H), 4.85~4.91 (m, 1H), 7.15 (m, 2H), 7.30 (m, 2H)

Example 30

(S)—N-((3R,4S,5S)-1-((2S,4R)-2-((1R,2R)-3-(2-(4-fluorophenyl)-2-oxoethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-30)

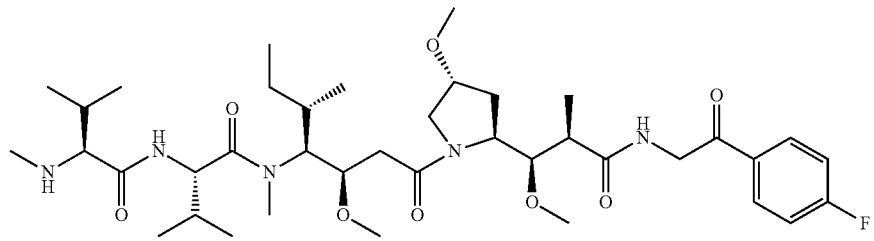 [SMILES: CC[C@H](C)[C@@H]([C@@H](CC(=O)N1C[C@H](OC)C[C@H]1[C@H](OC)[C@@H](C)C(=O)NCC(=O)c1ccc(F)cc1)OC)N(C)C(=O)[C@@H](NC(=O)[C@@H](NC)C(C)C)C(C)C]

With the exception that the compound (X-10) obtained in Preparation Example 6-10 was used instead of the compound (X-1) obtained in Preparation Example 6-1, the same procedure as in Example 1 was repeated to afford a compound in which the N-terminal amino group of compound (I-30) was protected. 0.25 g (97%).

$^1$H NMR (400 MHz, CDCl$_3$): δ 0.75~0.86 (m, 11H), 0.88 (d, J=6.4 Hz, 6H), 0.96 (d, J=6.8 Hz, 3H), 1.32 (d, J=7.2 Hz, 2H), 1.76~2.03 (m, 4H), 2.20~2.61 (m, 3H), 2.89~2.93 (m, 3H), 2.95~3.01 (m, 3H), 3.23 (s, 3H), 3.34 (s, 3H), 3.35~3.44 (m, 1H), 3.46 (s, 3H), 4.00 (dd, J=7.5 Hz, 2.8 Hz, 1H), 4.00~4.06 (m, 1H), 4.12~4.15 (m, 2H), 4.24~4.26 (m, 2H), 4.67~4.69 (m, 2H), 4.72 (d, J=4.8 Hz, 2H), 5.09~5.23 (m, 2H), 7.17 (t, J=8.8 Hz, 2H), 7.34 (m, 5H), 8.00 (dd, J=8.8 Hz, 5.2 Hz, 2H)

The title compound was prepared in the same manner as in Example 1, with the exception of using the compound in which the N-terminal amino group of compound (I-30) was protected. 0.2 g (95%).

$^1$H NMR (400 MHz, CDCl$_3$): δ 0.74~0.83 (m, 4H), 0.86~1.03 (m, 16H), 1.25~1.29 (m, 2H), 1.33 (d, J=6.8, 3H), 1.98~2.10 (m, 4H), 2.33 (s, 3H), 2.37~2.51 (m, 3H), 2.74 (d, J=4.8 Hz, 1H), 3.02 (m, 3H), 3.29 (s, 3H), 3.34 (d, J=6.4 Hz, 3H), 3.35~3.40 (m, 1H), 3.46 (s, 3H), 3.91~4.05 (m, 2H), 4.10~4.17 (m, 1H), 4.18~4.26 (m, 1H), 4.72 (d, J=4.8 Hz, 2H), 4.75~4.82 (m, 2H), 7.10 (t, J=8.8 Hz, 1H), 7.17 (t, J=8.8 Hz, 1H), 7.38 (m, 1H), 8.02 (m, 1H)

Example 31

(S)—N-((3R,4S,5 S)-1-((2S,4R)-2-((1R,2R)-3-(2-(2-fluoro-4-methoxyphenyl)-2-oxoethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-31)

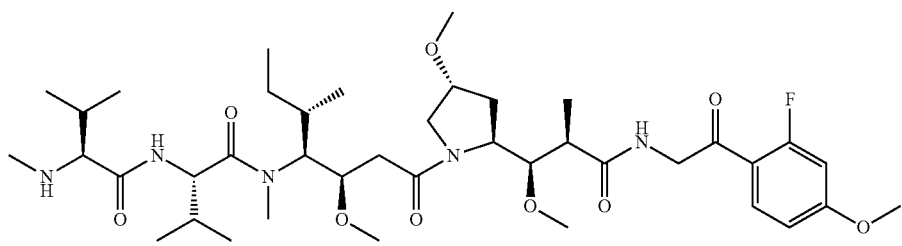

With the exception that the compound (X-7) obtained in Preparation Example 6-7 was used instead of the compound (X-1) obtained in Preparation Example 6-1, the same procedure as in Example 1 was repeated to afford a compound in which the N-terminal amino group of compound (I-31) was protected. 0.24 g (95%).

$^1$H NMR (400 MHz, CDCl$_3$) δ 0.72~0.92 (m, 14H), 0.96 (d, J=6.4 Hz, 2H), 1.02 (d, J=6.8 Hz, 2H), 1.32 (d, J=6.8 Hz, 2H), 1.76~2.10 (m, 4H), 2.19~2.60 (m, 3H), 2.89~2.92 (m, 3H), 2.95~3.01 (m, 3H), 3.24 (s, 3H), 3.34 (s, 3H), 3.35~3.44 (m, 1H), 3.46 (s, 3H), 3.87 (s, 3H), 3.98 (dd, J=7.6 Hz, 2.4 Hz, 1H), 4.00~4.06 (m, 1H), 4.11~4.15 (m, 2H), 4.24~4.28 (m, 2H), 4.62~4.64 (m, 2H), 4.68~4.70 (m, 1H), 5.09~5.23 (m, 2H), 6.64 (dd, J=13.2 Hz, 2.0 Hz, 2H), 6.78 (dd, J=8.8 Hz, 2.4 Hz, 2H), 7.34 (m, 5H), 7.95 (t, J=8.4 Hz, 2H)

The title compound was prepared in the same manner as in Example 1, with the exception of using the compound in which the N-terminal amino group of compound (I-31) was protected. 0.18 g (89%).

$^1$H NMR (400 MHz, CDCl$_3$): δ 0.80~0.84 (m, 3H), 0.88~1.03 (m, 17H), 1.32 (d, J=7.2 Hz, 3H), 1.35~1.39 (m, 2H), 1.98~2.10 (m, 4H), 2.35 (s, 3H), 2.36~2.51 (m, 3H), 2.74 (m, 1H), 3.02 (m, 3H), 3.29 (s, 3H), 3.34 (s, 3H), 3.45 (s, 3H), 3.46~3.56 (m, 1H), 3.87 (s, 3H), 3.99 (dd, J=7.6 Hz, 2.8 Hz, 1H), 4.10~4.15 (m, 1H), 4.25~4.28 (m, 1H), 4.58~4.64 (m, 2H), 4.73~4.78 (m, 1H), 6.67 (m, 1H), 6.78 (qd, J=10.4 Hz, 2.8 Hz, 1H), 7.95 (m, 1H)

Example 32

(S)—N-((3R,4S,5S)-1-((S)-4-((1R,2R)-3-((2,6-difluorophenethyl)amino)-1-methoxy-2-methyl-3-oxopropyl)thiazolidin-3-yl)-3-methoxy-5-methyl-1-oxoheptan-4-yl)-N,3-dimethyl-2-((S)-3-methyl-2-(methylamino)butaneamido)butanamide (I-32)

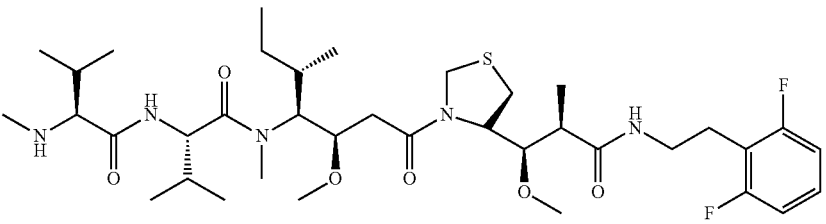

With the exception that the compound (X-24) obtained in Preparation Example 6-24 was used instead of the compound (X-1) obtained in Preparation Example 6-1, the same procedure as in Example 1 was repeated to afford a compound in which the N-terminal amino group of compound (I-32) was protected. 0.23 g (70%).

$^1$H NMR (400 MHz, CDCl$_3$): δ 0.74~1.05 (m, 18H), 1.17~1.25 (d, 3H), 1.47 (s, 9H), 1.61 (s, 2H), 2.21~2.47 (m, 3H), 2.65~3.12 (m, 8H), 2.88 (s, 3H), 2.98 (s, 3H), 3.35 (s, 3H), 3.42 (S, 3H), 3.77~4.18 (m, 3H), 4.16~4.21 (m, 3H), 4.66~4.70 (m, 2H), 5.09~5.23 (m, 3H), 7.32 (m, 7H), 7.59 (m, 1H)

The title compound was prepared in the same manner as in Example 1, with the exception of using the compound in which the N-terminal amino group of compound I-32 was protected. 0.17 g (90%).

MALDI-TOF MS m/z: 742.9 [M+1]$^+$ $^1$H NMR (400 MHz, CDCl$_3$): δ 0.74~1.05 (m, 18H), 1.17~1.25 (d, 3H), 1.47 (s, 9H), 1.61 (s, 2H), 2.21~2.47 (m, 3H), 2.65~3.12 (m, 8H), 2.88 (s, 3H), 2.98 (s, 3H), 3.35 (s,

3H), 3.42 (S, 3H), 3.77~4.18 (m, 3H), 4.16~4.21 (m, 3H), 4.66~4.70 (m, 2H), 5.16 (br, 1H), 7.32~7.37 (m, 2H), 7.59 (m, 1H)

Example 33

(2S)—N-((3R,4S)-3-methoxy-1-((2S,4S)-4-methoxy-2-((1R,2R)-1-methoxy-2-methyl-3-oxo-3-(phenethylamino)propyl)pyrrolidin-1-yl)-5-methyl-1-oxo-heptan-4-yl)-N,3-dimethyl-2-((S)-3-methyl-2-(methylamino)butaneamido)butanamide (I-33)

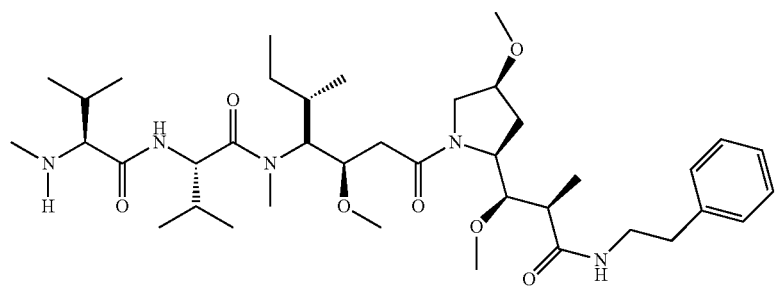 [SMILES: CC[C@H](C)[C@@H]([C@@H](CC(=O)N1C[C@@H](OC)C[C@H]1[C@H](OC)[C@@H](C)C(=O)NCCc1ccccc1)OC)N(C)C(=O)[C@@H](NC(=O)[C@@H](NC)C(C)C)C(C)C]

With the exception that the compound (X-11) obtained in Preparation Example 6-11 was used instead of the compound (X-1) obtained in Preparation Example 6-1, the same procedure as in Example 1 was repeated to afford a compound in which the N-terminal amino group of compound (I-33) was protected. 0.40 g (77%).

$^1$H NMR (400 MHz, CDCl$_3$): δ 0.79~1.06 (m, 15H), 1.73~1.38 (m, 5H), 1.76~2.03 (m, 6H), 2.98~2.37 (m, 4H), 2.77~2.82 (m, 2H), 2.90~3.01 (m, 3H), 3.0 (s, 3H), 3.25~3.28 (m, 1H), 3.3 (s, 3H), 3.33 (s, 3H), 3.36 (s, 3H), 3.38~3.54 (m, 3H), 3.74~3.75 (m, 1H), 3.81~3.96 (m, 1H), 3.93~3.96 (m, 1H), 4.09~4.11 (m, 1H), 4.68~4.69 (m, 1H), 5.09~5.23 (m, 2H), 6.16~6.17 (m, 1H) 6.53~6.54 (m, 1H), 7.17~7.34 (m, 10H)

The title compound was prepared in the same manner as in Example 1, with the exception of using the compound in which the N-terminal amino group of compound (I-33) was protected. 0.31 g (93%).

$^1$H NMR (400 MHz, CDCl$_3$): δ 0.81~0.85 (m, 3H), 0.92~1.16 (m, 15H), 1.16~1.24 (d, 3H), 1.27~1.37 (m, 1H), 1.89~2.12 (m, 5H), 2.33 (s, 3H), 2.36~2.37 (m, 3H), 2.74~2.96 (m, 4H), 3.03 (s, 3H), 3.23~3.28 (m, 1H), 3.31 (s, 3H), 3.36 (s, 3H), 3.4 (s, 3H), 3.51~3.62 (m, 3H), 3.7~3.78 (m, 1H), 3.81~3.96 (m, 1H), 3.91~3.97 (m, 1H), 4.11~4.15 (m, 2H) 4.44~4.88 (m, 2H), 6.2 (m, 1H), 7.17~7.34 (m, 5H), 7.57~7.60 (m, 1H)

Example 34

(2S)—N-((3R,4S)-3-methoxy-1-((2S,4R)-4-methoxy-2-((1R,2R)-1-methoxy-2-methyl-3-oxo-3-(2-oxo-2-phenylethyl)amino)propyl)pyrrolidin-1-yl)-5-methyl-1-oxoheptan-4-yl)-N,3-dimethyl-2-((S)-3-methyl-2-(methylamino)butaneamido)butanamide (I-34)

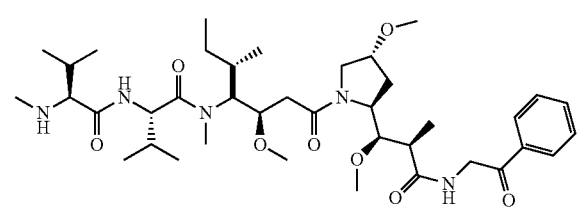 [SMILES: CC[C@H](C)[C@@H]([C@@H](CC(=O)N1C[C@H](OC)C[C@H]1[C@H](OC)[C@@H](C)C(=O)NCC(=O)c1ccccc1)OC)N(C)C(=O)[C@@H](NC(=O)[C@@H](NC)C(C)C)C(C)C]

With the exception that the compound (X-8) obtained in Preparation Example 6-8 was used instead of the compound (X-1) obtained in Preparation Example 6-1, the same procedure as in Example 1 was repeated to afford a compound in which the N-terminal amino group of compound (I-34) was protected. 2.36 g (81%).

¹H NMR (400 MHz, CDCl₃): δ 0.71~1.04 (m, 17H), 1.31~1.32 (m, 4H), 1.77~1.81 (m, 2H) 1.92~2.04 (m, 4H), 2.17~2.61 (m, 4H), 2.89~2.95 (m, 3H), 2.99 (s, 3H), 3.31 (s, 6H), 3.46 (s, 3H), 3.43-3.52 (m, 1H), 3.99~4.01 (m, 1H), 4.09~4.15 (m, 1H), 4.24 (m, 1H), 4.69~4.73 (m, 4H), 4.74~4.76 (d, 2H), 5.09~5.23 (m, 2H), 6.46~6.49 (m, 1H) 7.12 (m, 1H), 7.26~7.34 (m, 5H), 7.48~7.51 (t, 2H), 7.6~7.64 (t, 1H), 7.96~8.04 (d, 2H)

The title compound was prepared in the same manner as in Example 1, with the exception of using the compound in which the N-terminal amino group of compound (I-34) was protected. 1.89 g (96%).

¹H NMR (400 MHz, CDCl₃): δ 0.81~0.85 (m, 3H), 0.92~1.14 (m, 13H), 1.25~1.43 (m, 5H), 1.46~1.89 (m, 6H), 1.92~2.22 (m, 5H), 2.33 (s, 3H), 2.45~2.54 (m, 2H), 2.73~2.74 (d, 1H), 3.02 (s, 3H), 3.32 (s, 6H), 3.41 (d, 3H), 3.52~3.84 (m, 3H), 3.92~4.06 (m, 3H), 4.75~4.8 (m, 2H), 4.94~5.23 (m, 1H), 6.76~6.94 (m, 1H), 7.34~7.43 (m, 4H), 7.60 (m, 1H)

Example 35

(2S)—N-((3R,4S)-1-((2S,4R)-2-((1R,2R)-3-(2-(2-hydroxy-2-phenylethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-35)

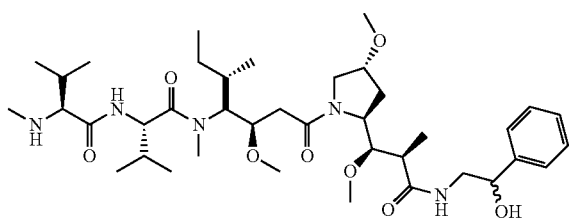 [SMILES: CC[C@H](C)[C@@H]([C@@H](CC(=O)N1C[C@H](OC)C[C@H]1[C@H](OC)[C@@H](C)C(=O)NCC(O)c1ccccc1)OC)N(C)C(=O)[C@@H](NC(=O)[C@@H](NC)C(C)C)C(C)C]

With the exception that the compound (X-12) obtained in Preparation Example 6-12 was used instead of the compound (X-1) obtained in Preparation Example 6-1, the same procedure as in Example 1 was repeated to afford a compound in which the N-terminal amino group of compound (I-35) was protected. 0.24 g (57%).

¹H NMR (400 MHz, CDCl₃): δ 0.71~0.97 (m, 17H), 1.22~1.29 (m, 4H), 1.77~1.81 (m, 2H) 1.92~2.04 (m, 4H), 2.17~2.61 (m, 4H), 2.88~2.95 (m, 3H), 2.99 (s, 3H), 3.32 (s, 6H), 3.46 (s, 3H), 3.43~3.52 (m, 1H), 3.52~4.04 (m, 5H), 4.51~4.96 (m, 5H), 5.09~5.23 (m, 2H), 6.46~6.49 (m, 1H) 7.12 (m, 1H), 7.26~7.43 (m, 10H)

The title compound was prepared in the same manner as in Example 1, with the exception of using the compound in which the N-terminal amino group of compound (I-35) was protected. 0.20 g (99%).

¹H NMR (400 MHz, CDCl₃): δ 0.81~0.86 (m, 3H), 0.93~1.03 (m, 12H), 1.18 (d, 1H), 1.20~1.31 (m, 3H), 1.53~1.79 (m, 6H), 2.01~2.08 (m, 3H), 2.35 (s, 3H), 2.34~2.39 (m, 1H), 2.73~2.74 (d, 1H), 3.03 (d, 1H), 3.06 (s, 2H), 3.32 (s, 6H), 3.38~3.48 (m, 3H), 3.92~4.18 (m, 5H), 4.75~4.95 (m, 2H), 7.23~7.4 (m, 5H)

Example 36

(2S)—N-((3R,4S)-1-((2S)-2-((1R,2R)-3-(((2R)-1-amino-1-phenylpropan-2-yl)amino)-1-methoxy-2-methyl-3-oxopropyl)-4-methoxypyrrolidin-1-yl)-3-methoxy-5-methyl-1-oxoheptan-4-yl)-2-((S)-2-(dimethylamino)-3-methylbutaneamido)-N,3-dimethylbutanamide (I-36)

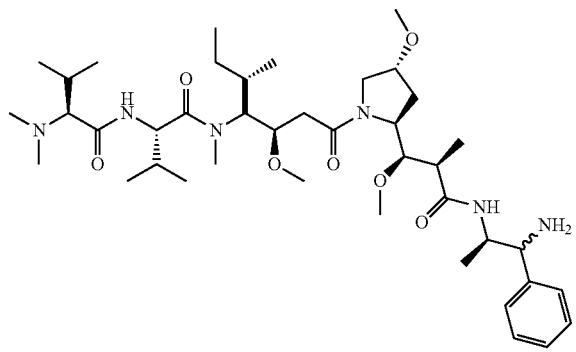 [SMILES: CC[C@H](C)[C@@H]([C@@H](CC(=O)N1C[C@H](OC)C[C@H]1[C@H](OC)[C@@H](C)C(=O)N[C@H](C)C(N)c1ccccc1)OC)N(C)C(=O)[C@@H](NC(=O)[C@H](C(C)C)N(C)C)C(C)C]

With the exception that the compound (X-13) obtained in Preparation Example 6-13 and the compound (II-2) were used instead of the compound (X-1) obtained in Preparation Example 6-1 and the compound (II-1), respectively, the same procedure as in Example 1 was repeated to afford a compound in which the N-terminal amino group of compound (I-36) was protected. 55 mg (52%).

¹H NMR (400 MHz, CDCl₃): δ 0.79~0.81 (m, 3H) 0.92~1.09 (m, 12H), 1.11~1.25 (m, 6H) 1.72~2.24 (m, 9H), 2.24 (s, 3H), 2.45 (m, 2H), 2.98-2.93 (m, 3H), 3.33 (s, 6H), 3.35 (s, 3H), 3.45~3.54 (m, 2H), 3.71 (d, 1H), 4.01-4.15 (m, 2H), 4.23-4.37 (m, 2H), 4.69~4.75 (m, 2H), 5.12-5.22 (m, 2H), 6.74~6.88 (m, 1H), 7.26~7.33 (m, 10H)

The title compound was prepared in the same manner as in Example 1, with the exception of using the compound in which the N-terminal amino group of compound (I-36) was protected. 44 mg (95%).

MALDI-TOF MS m/z: 731.6 [M+1]⁺

Example 37

(2S)—N-((3R,4S)-1-((2S,4R)-2-((1R,2R)-3-(((2S)-1-amino-1-phenylpropan-2-yl)amino)-1-methoxy-2-methyl-3-oxopropyl)-4-methoxypyrrolidin-1-yl)-3-methoxy-5-methyl-1-oxoheptan-4-yl)-2-((S)-2-(dimethylamino)-3-methylbutaneamido)-N,3-dimethylbutanamide (I-37)

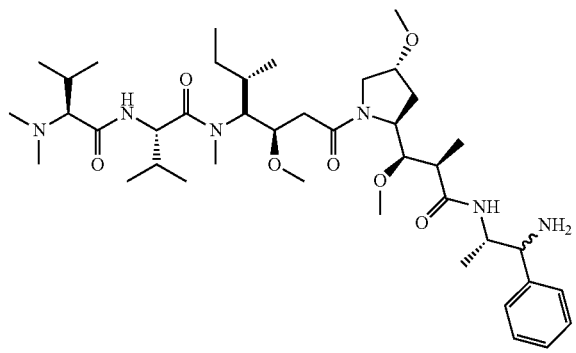 [SMILES: CC[C@H](C)[C@@H]([C@@H](CC(=O)N1C[C@H](OC)C[C@H]1[C@H](OC)[C@@H](C)C(=O)N[C@@H](C)C(N)c1ccccc1)OC)N(C)C(=O)[C@@H](NC(=O)[C@H](C(C)C)N(C)C)C(C)C]

With the exception that the compound (X-14) obtained in Preparation Example 6-14 and the compound (II-2) were used instead of the compound (X-1) obtained in Preparation Example 6-1 and the compound (II-1), respectively, the same procedure as in Example 1 was repeated to afford a compound in which the N-terminal amino group of compound (I-37) was protected. 96 mg (48%).

¹H NMR (400 MHz, CDCl₃): δ 0.79~0.81 (m, 3H), 0.92~1.09 (m, 12H), 1.11~1.25 (m, 6H), 1.72~2.24 (m, 9H), 2.24 (s, 3H), 2.45 (m, 2H), 2.98-2.93 (m, 3H), 3.33 (s, 6H), 3.35 (s, 3H), 3.45~3.54 (m, 2H), 3.71 (d, 1H), 4.01-4.15 (m, 2H), 4.23-4.37 (m, 2H), 4.69~4.75 (m, 2H), 5.12-5.22 (m, 2H), 6.74~6.88 (m, 1H), 7.26~7.33 (m, 10H)

The title compound was prepared in the same manner as in Example 1, with the exception of using the compound in which the N-terminal amino group of compound (I-37) was protected. 75 mg (95%).

MALDI-TOF MS m/z: 730.9 [M+1]⁺

Example 38

(2S)—N-((3R,4S)-3-methoxy-1-((2S,4R)-4-methoxy-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N,3-dimethyl-2-((S)-3-methyl-2-(methylamino)butaneamido)butanamide
(I-38)

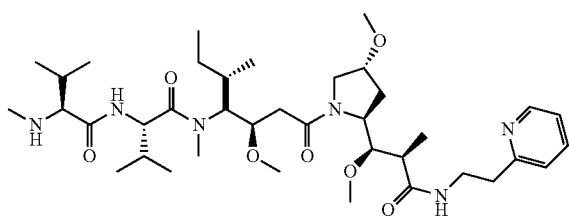 [SMILES: CC[C@H](C)[C@@H]([C@@H](CC(=O)N1C[C@H](OC)C[C@H]1[C@H](OC)[C@@H](C)C(=O)NCCc1ccccn1)OC)N(C)C(=O)[C@@H](NC(=O)[C@@H](NC)C(C)C)C(C)C]

With the exception that the compound (X-15) obtained in Preparation Example 6-15 was used instead of the compound (X-1) obtained in Preparation Example 6-1, the same procedure as in Example 1 was repeated to afford a compound in which the N-terminal amino group of compound (I-38) was protected. 0.35 g (35%).

¹H NMR (400 MHz, CDCl₃): δ 0.75~1.00 (m, 18H), 1.19~1.24 (m, 3H), 1.94~1.97 (m, 4H), 2.04 (s, 1.H), 2.23~2.26 (m, 2H), 2.35~2.49 (m, 2H), 2.87~2.92 (m, 3H), 2.96~3.12 (m, 3H), 3.31 (s, 4H), 3.37 (d, 3H), 3.42~3.49 (m, 3H), 3.61~3.68 (m, 3H), 3.86~3.89 (m, 1H), 4.11~4.19 (m 1H), 4.70 (m, 1H), 5.10~5.23 (m, 2H), 6.92 (m, 1H), 7.12~7.20 (m, 2H), 7.33 (m, 5H), 7.58~7.63 (m, 2H), 8.51~8.21 (m, 1H)

The title compound was prepared in the same manner as in Example 1, with the exception of using the compound in which the N-terminal amino group of compound (I-38) was protected. 0.25 g (86%).

¹H NMR (400 MHz, CDCl₃): δ 0.81~0.84 (m, 3H), 0.92~1.00 (m, 15H), 1.19~1.25 (m, 3H), 1.76~2.03 (m, 4H), 2.34 (m, 3H), 2.37~2.42 (m, 1H), 2.27~2.77 (m, 1H), 2.99~3.03 (m, 3H), 3.15 (s, 1H), 3.32 (s, 6H), 3.38 (d, J=4 Hz, 3H), 3.64 (m, 2H), 3.88 (m, 1H), 4.12 (m, 2H), 4.77 (m, 1H), 6.93 (m, 1H), 7.12~7.19 (m, 2H), 7.58~7.65 (m, 2H), 8.52 (m, 1H)

Example 39

(2S)—N-((3R,4S)-3-methoxy-1-((2S,4R)-4-methoxy-2-((1R,2R)-1-methoxy-2-methyl-3-oxo-3-((2-(thiophen-2-yl)ethyl)amino)propyl)pyrrolidin-1-yl)-5-methyl-1-oxoheptan-4-yl)-N,3-dimethyl-2-((S)-3-methyl-2-(methylamino)butaneamido)butanamide
(I-39)

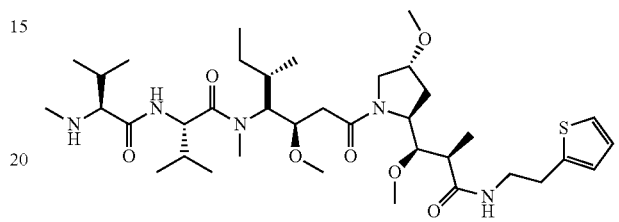

With the exception that the compound (X-16) obtained in Preparation Example 6-16 was used instead of the compound (X-1) obtained in Preparation Example 6-1, the same procedure as in Example 1 was repeated to afford a compound in which the N-terminal amino group of the title compound (I-39) was protected. 0.8 g (99%).

¹H NMR (400 MHz, CDCl₃): δ 0.79~1.00 (m, 18H), 1.01~1.25 (m, 3H), 1.75~1.82 (m, 4H), 2.04 (s, 1.H), 2.24~2.42 (m, 2H), 2.35~2.49 (m, 2H), 2.88~2.92 (m, 3H), 3.00~3.07 (m, 4H), 3.27 (s, 3H), 3.33 (m, 3H), 3.38 (m, 3H), 3.45~3.57 (m, 3H), 3.85~3.87 (m, 1H), 4.08~4.16 (m, 1H), 4.71 (m, 1H), 5.13~5.23 (m, 2H), 6.57 (m, 1H), 6.84 (d, J=2.8 Hz, 1H), 6.91~6.93 (m, 1H), 7.13 (d, J=2.1 Hz, 1H), 7.34 (m, 5H)

The title compound was prepared in the same manner as in Example 1, with the exception of using the compound in which the N-terminal amino group of compound (I-39) was protected. 70 mg (10%).

¹H NMR (400 MHz, CDCl₃): δ 0.81~0.85 (m, 3H), 0.88~1.00 (m, 15H), 1.22~1.26 (m, 3H), 2.03 (m, 3H), 2.34~2.37 (m, 3H), 3.01~3.07 (m, 3H), 3.15 (s, 4H), 3.33 (d, 3H), 3.38 (d, 3H), 3.43~3.58 (m, 2H), 3.85~3.87 (m, 1H), 4.09~4.13 (m, 2H), 4.75~4.79 (m, 1H), 6.62 (m, 1H), 6.90 (m, 1H), 6.91~6.93 (m, 1H), 7.13~7.20 (m, 1H)

Example 40

(2S)—N-((3R,4S)-1-((2S,4S)-2-((1R,2R)-3-(2,6-difluorophenethyl)amino)-1-methoxy-2-methyl-3-oxopropyl)-4-hydroxypyrrolidin-1-yl)-3-methoxy-5-methyl-1-oxoheptan-4-yl)-2-((S)-2-(dimethylamino)-3-methylbutaneamido)-N,3-dimethylbutanamide
(I-40)

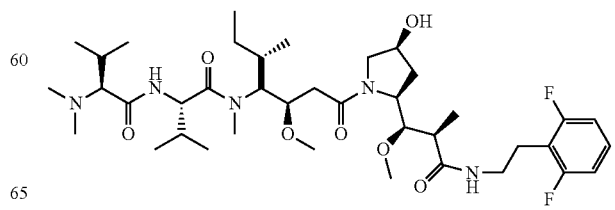

With the exception that the compound (X-25) obtained in Preparation Example 6-25 and (3R,4S,5S)-4-((S)-2-((S)-2-(dimethylamino)-3-methylbutaneamido)-N,3-dimethylbutaneamido)-3-methoxy-5-methylheptanic acid (compound II-2) were used instead of the compound (X-1) obtained in Preparation Example 6-1 and the compound (II-1), respectively, the same procedure as in Example 1 was repeated to afford the title compound. 2.25 g (76%).

[α]$_D$25=−40.5° (c=1, MeOH)

$^1$H NMR (400 MHz, CDCl$_3$): δ 0.79-1.05 (m, 19H), 1.26 (m, 3H), 1.45 (m, 2H), 1.66 (m, 2H), 1.97-2.17 (m, 3H), 2.44-2.46 (m, 3H), 2.71-2.80 (m, 3H), 2.81-2.89 (m, 1H), 2.91-2.94 (m, 2H), 2.71-2.80 (m, 3H), 3.04 (s, 3H), 3.26-3.33 (m, 2H), 3.37 (s, 3H), 3.74 (m, 2H), 4.28-4.31 (m, 2H), 4.75-4.82 (m, 2H), 6.18 (m, 1H), 6.84-6.89 (m, 2H), 7.15-7.19 (m, 1H), 7.58 (d, 1H)

LC-MS m/z: 754[M+]$^+$

Example 41

(2S)-2-((S)-2-(dimethylamino)-3-methylbutaneamido)-N-((3R,4S)-1-((2S,4S)-2-((1R,2R)-3-(((S)-1-(4-fluorophenyl)-1-oxopropan-2-yl)amino)-1-methoxy-2-methyl-3-oxopropyl)-4-hydroxypyrrolidin-1-yl)-3-methoxy-5-methyl-1-oxoheptan-4-yl)-N,3-dimethylbutanamide (I-41)

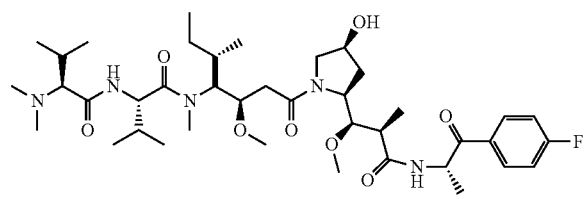 [SMILES: CC[C@H](C)[C@@H]([C@@H](CC(=O)N1C[C@@H](O)C[C@H]1[C@H](OC)[C@@H](C)C(=O)N[C@@H](C)C(=O)c1ccc(F)cc1)OC)N(C)C(=O)[C@@H](NC(=O)[C@H](C(C)C)N(C)C)C(C)C]

With the exception that the compound (X-26) obtained in Preparation Example 6-26 and (3R,4S,5S)-4-((S)-2-((S)-2-(dimethylamino)-3-methylbutaneamido)-N,3-dimethylbutaneamido)-3-methoxy-5-methylheptanic acid (compound II-2) were used instead of the compound (X-1) obtained in Preparation Example 6-1 and the compound (II-1), respectively, the same procedure as in Example 1 was repeated to afford the title compound. 3.4 g (58%).

$^1$H NMR (400 MHz, CDCl$_3$): δ 0.80~0.83 (m, 3H), 0.92~1.04 (m, 9H), 1.22~1.31 (m, 3H), 1.35~1.42 (m, 1H), 1.43~1.45 (m, 3H), 1.97~2.09 (m, 3H), 2.21~2.22 (m, 1H), 2.30~2.38 (m, 6H), 2.20~2.58 (m, 3H), 2.72~2.76 (m, 1H), 3.01 (d, 2H), 3.35 (d, 3H), 3.35~3.62 (m, 1H), 3.55 (d, 3H), 4.08~4.15 (m, 2H), 4.31~4.37 (m, 1H), 4.73~4.79 (m, 1H), 5.43~5.54 (m, 1H), 7.15~7.17 (m, 2H), 7.53~7.61 (m, 1H), 8.02~8.09 (m, 2H)

LC-MS m/z: 764[M+]$^+$

Example 42

(2S)—N-((3R,4S)-1-((2S,4S)-2-((1R,2R)-3-((2,6-difluorophenethyl)amino)-1-methoxy-2-methyl-3-oxopropyl)-4-hydroxypyrrolidin-1-yl)-3-methoxy-5-methyl-1-oxoheptan-4-yl)-N,3-dimethyl-2-((S)-3-methyl-2-(methylamino)butaneamido)butanamide (I-42)

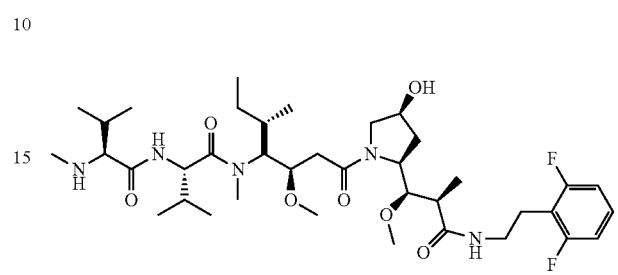

With the exception that the compound (X-25) obtained in Preparation Example 6-25 was used instead of the compound (X-1) obtained in Preparation Example 6-1, the same procedure as in Example 1 was repeated to afford a compound in which the N-terminal amino group of compound I-42 was protected. 4.37 g (63%).

ES-MS m/z: 874 [M+H]$^+$

The title compound was prepared in the same manner as in Example 1, with the exception of using the compound in which the N-terminal amino group of compound (I-42) was protected. 2.98 g (85%).

$^1$H NMR (400 MHz, CDCl$_3$): δ 0.80~0.85 (m, 3H), 0.92~1.00 (m, 15H), 1.01~1.08 (m, 1H), 1.26 (d, 3H, J=7.2 Hz), 1.31~1.38 (m, 1H), 1.81~2.17 (m, 4H), 2.36 (s, 3H), 2.40~2.42 (m, 2H), 2.76~2.78 (m, 1H), 2.90~2.93 (m, 2H), 3.03 (s, 3H), 3.31 (s, 3H), 3.35~3.57 (m, 4H), 3.49 (s, 3H), 4.03~4.10 (m, 2H), 4.28~4.30 (m, 2H), 4.75~4.89 (m, 2H), 6.21 (m, 1H), 6.82~6.91 (m, 2H), 7.13~7.21 (m, 1H), 7.58 (d, 1H, J=9.2 Hz)

LC-MS m/z: 740[M+]$^+$

Example 43

(2S)—N-((3R,4S)-1-((2S,4S)-2-((1R,2R)-3-(((S)-1-(4-fluorophenyl)-1-oxopropan-2-yl)amino)-1-methoxy-2-methyl-3-oxopropyl)-4-hydroxypyrrolidin-1-yl)-3-methoxy-5-methyl-1-oxoheptan-4-yl)-N,3-dimethyl-2-((S)-3-methyl-2-(methylamino)butaneamido)butanamide (I-43)

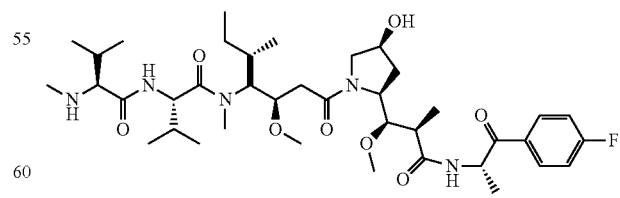

With the exception that the compound (X-26) obtained in Preparation Example 6-26 was used instead of the compound (X-1) obtained in Preparation Example 6-1, the same procedure as in Example 1 was repeated to afford the title compound. 0.12 g (51%).

¹H NMR (400 MHz, CDCl₃): δ 0.77~0.83 (m, 3H), 0.92~1.04 (m, 9H), 1.32~1.35 (m, 3H), 1.34~1.41 (m, 1H), 1.41~1.42 (m, 3H), 1.97~2.09 (m, 3H), 2.21~2.22 (m, 1H), 2.33~2.35 (m, 3H), 2.23~2.56 (m, 3H), 2.72~2.76 (m, 1H), 3.01 (d, 2H), 3.35 (d, 3H), 3.35~3.62 (m, 1H), 3.55 (d, 3H), 4.08~4.15 (m, 2H), 4.31~4.37 (m, 1H), 4.73~4.79 (m, 1H), 5.43~5.54 (m, 1H), 7.15~7.17 (m, 2H), 7.57~7.60 (m, 1H), 8.00~8.07 (m, 2H)

LC-MS m/z: 750[M+]+, 772[M+Na]⁺

Example 44

(2S)—N-((3R,4S)-1-((2S,4S)-4-amino-2-((1R,2R)-3-((2,6-difluorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutaneamido)-N,3-dimethylbutanamide (I-44)

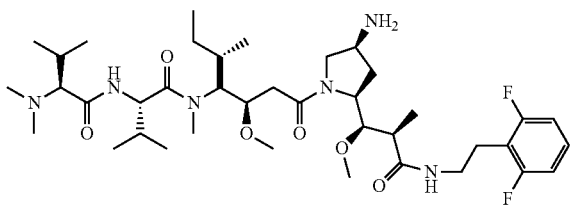 [SMILES: CC[C@H](C)[C@@H]([C@@H](CC(=O)N1C[C@@H](N)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

With the exception that the compound (X-27) obtained in Preparation Example 6-27 and (3R,4S,5S)-4-((S)-2-((S)-2-(dimethylamino)-3-methylbutaneamido)-N,3-dimethylbutaneamido)-3-methoxy-5-methylheptanic acid (compound II-2) was used instead of the compound (X-1) obtained in Preparation Example 6-1 and compound (II-1), respectively, the same procedure as in Example 1 was repeated to give an azide compound of compound (I-44). 0.42 g (76%).

¹H NMR (400 MHz, CDCl₃): δ 0.79-1.07 (m, 15H), 1.20 (d, 2H), 1.99-2.11 (m, 4H), 2.18-2.28 (m, 5H), 2.33-2.45 (m, 4H), 2.90-3.27 (m, 6H), 3.32-3.42 (m, 6H), 3.47-3.54 (m, 2H), 3.75-3.78 (m, 1H), 3.85-3.98 (m, 2H), 4.19-4.21 (m, 1H), 4.39-4.44 (m, 1H), 4.46-4.80 (m, 1H), 4.87-4.90 (m, 1H), 6.17 (m, 1H), 6.84-6.95 (m, 2H), 7.14-7.26 (m, 1H)

The azide compound of compound (I-44) was dissolved in 10 mL of methyl alcohol, and reacted for 14 hrs in the presence of 10% palladium carbon (15 mg) in a hydrogen atmosphere while stirring. After completion of the reaction, the reaction mixture was filtered through celite, and washed several times with methanol. Removal of the solvent in a vacuum left the title compound as a white solid. 0.23 g (99%).

¹H NMR (400 MHz, CDCl₃): δ 0.79-1.03 (m, 14H), 1.21-1.22 (m, 5H), 2.06-2.45 (m, 6H), 2.89-3.02 (m, 4H), 3.30-3.44 (m, 5H), 3.47-3.52 (m, 2H), 3.67-3.69 (m, 1H), 3.71-4.39 (m, 3H), 4.78-4.80 (m, 1H), 6.17 (m, 1H), 6.84-6.95 (m, 2H), 7.14-7.26 (m, 1H)

LC-MS m/z: 753[M+]⁺, 775[M+Na]⁺

Example 45

(2S)—N-((3R,4S)-1-((2S,4S)-2-((1R,2R)-3-(2,6-difluorophenethyl)amino)-1-methoxy-2-methyl-3-oxopropyl)-4-(methylamino)pyrrolidin-1-yl)-3-methoxy-5-methyl-1-oxoheptan-4-yl)-2-((S)-2-(dimethylamino)-3-methylbutaneamido)-N,3-dimethylbutanamide (I-45)

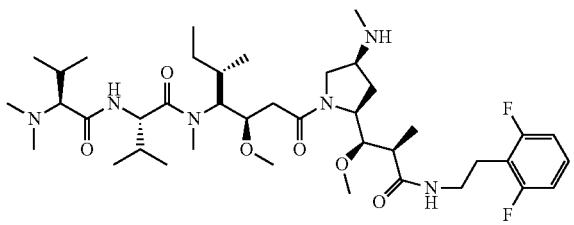 [SMILES: CC[C@H](C)[C@@H]([C@@H](CC(=O)N1C[C@@H](NC)C[C@H]1[C@H](OC)[C@@H](C)C(=O)NCCc1c(F)cccc1F)OC)N(C)C(=O)[C@@H](NC(=O)[C@H](C(C)C)N(C)C)C(C)C]

With the exception that the compound (X-28) obtained in Preparation Example 6-28 and (3R,4S,5S)-4-((S)-2-((S)-2-(dimethylamino)-3-methylbutaneamido)-N,3-dimethylbutaneamido)-3-methoxy-5-methylheptanic acid (compound II-2) were used instead of the compound (X-1) obtained in Preparation Example 6-1 and compound (II-1), respectively, the same procedure as in Example 1 was repeated to afford a compound in which the amino group of compound (I-45) was protected. 0.13 g (64%).

LC-MS m/z: 857.5[M+]⁺

The compound in which the amino group of compound (I-45) was protected was dissolved in 10 mL of methyl alcohol, and reacted in the presence of 20% palladium hydroxide (66 mg) under a hydrogen pressure (55 psi) for 12 hrs while stirring. After completion of the reaction, the reaction mixture was filtered through celite, and washed several times with methanol. Removal of the solvent in a vacuum left the title compound as a white solid. 115 mg (100%).

¹H NMR (400 MHz, CDCl₃): δ 0.79-1.03 (m, 14H), 1.21-1.22 (m, 5H), 2.06-2.45 (m, 6H), 2.89-3.02 (m, 4H), 3.30-3.44 (m, 5H), 3.47-3.52 (m, 2H), 3.67-3.69 (m, 1H), 3.71-4.39 (m, 3H), 4.78-4.80 (m, 1H), 6.17 (m, 1H), 6.84-6.95 (m, 2H), 7.14-7.26 (m, 1H)

LC-MS m/z: 767.6[M+]⁺, 789.4[M+Na]⁺

Test Example 1

Assay for Anticancer Activity

The compounds of the present invention were assayed for inhibitory activity against 7 cancer cell lines as breast cancer (BT-474), human epithelial cancer (A-431), non-small cell lung cancer (NCI-H460), colon cancer (HT-29), colon cancer (SW-620), breast cancer (MDA-MB-231) and breast cancer (MCF-7).

Briefly, a suspension of each cancer cell line was serially diluted, and plated at a density of 2~3×10³ cells/well into 96-well microplates, followed by incubation at 37° C. for 4 day in a 5% CO₂ atmosphere. Cell growth in a monolayer was measured using WST-8 reagemt (Dojindo, Japan).

IC₅₀ values of the compounds against the cancer cell lines were calculated as compound concentrations at which the cells were grown by 50% OD of the control. The results are summarized in Table 1, below.

Meanwhile, the present invention is not limited to the above-described embodiments and may be changed and modified, without departing from the gist of the present invention, and it should be understood that the technical spirit of such changes and modifications also belong to the scope of the accompanying claims.

TABLE 1

| Cpd. | BT-474 | A-431 | NCI-H460 | HT-29 | SW-620 | MDA-MB-231 | MCF-7 |
|---|---|---|---|---|---|---|---|
| Doxorubcin | | | 150 | 1.810 | 290 | 850 | 460 |
| Paclitaxel | 14.4 | 442 | 26.80 | 19.51 | 26.75 | 90 | 27.09 |
| Dolastatin 10 | 0.65 | | | | | | |
| I-1 | 0.12 | | | | | | |
| I-2 | 0.70 | | | | | | |
| I-3 | 1.10 | 37.9 | | | | | |
| I-4 | 2.44 | 21.1 | | | | | |
| I-5 | 0.53 | 61.2 | | | | | |
| I-6 | 0.32 | | | | | | |
| I-7 | 0.62 | | | | | | |
| I-8 | 0.68 | | 1.5 | | 2.9 | | 27.0 |
| I-9 | 5.23 | | 10.9 | | 27.7 | | 27.0 |
| I-10 | 0.24 | | | | | | |
| I-11 | 0.78 | | | | | | |
| I-12 | 0.57 | | | | | | |
| I-13 | 0.41 | | | | | | |
| I-14 | 0.29 | | | | | | |
| I-15 | 0.51 | | | | | | |
| I-16 | 0.65 | | | | | | |
| I-17 | 0.25 | | | | | | |
| I-18 | 0.88 | | | | | | |
| I-19 | 0.09 | | | | | | |
| I-20 | 0.47 | | | | | | |
| I-21 | 0.59 | | | | | | |
| I-22 | 0.91 | | | | | | |
| I-23 | 0.98 | | | | | | |
| I-24 | 1.34 | | | | | | |
| I-25 | 0.41 | | | | | | |
| I-26 | 0.79 | | | | | | |
| I-27 | 0.50 | | | | | | |
| I-28 | 0.65 | | | | | | |
| I-29 | 0.61 | | | | | | |
| I-30 | 0.77 | | | | | | |
| I-31 | 0.54 | | | | | | |
| I-32 | 0.64 | | | | | | |
| I-33 | 0.68 | | 9.4 | 2.82 | 5.49 | 2.23 | 1.82 |
| I-34 | 9.71 | | 10.9 | | | | |
| I-35 | 0.23 | | 1.5 | 4.2 | 2.1 | | |
| I-36 | 0.51 | | | | | | |
| I-37 | 2.82 | | | | | | |
| I-38 | 1.32 | | | | | | |
| I-39 | 0.67 | | | | | | |
| I-40 | 0.23 | | | | | | |
| I-41 | 1.83 | | | | | | |
| I-42 | 0.74 | | | | | | |
| I-43 | 6.43 | | | | | | |
| I-44 | 0.17 | | | | | | |
| I-45 | 0.34 | | | | | | |

The invention claimed is:

1. A dolastatin-10 derivative, represented by the following Chemical Formula I:

[Chemical Formula I]

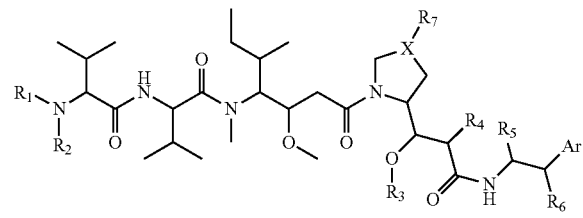

or a pharmaceutically acceptable salt thereof, wherein $R_1$, $R_2$, $R_3$, $R_4$, and $R_5$ are each independently hydrogen or $C_1$-$C_4$ alkyl, $R_6$ is hydrogen, hydroxy, $C_1$-$C_4$ alkoxy, amino, oxo(=O), or hydroxyimino(=N—OH), Ar is aryl, X is a carbon, oxygen or sulfur atom, and $R_7$ is hydroxy, amino, $C_1$-$C_4$ alkoxy, $C_1$-$C_4$ alkylamino, or oxo (=O) when X is a carbon atom, and is absent when X is an oxygen or sulfur atom.

2. The dolastatin-10 derivative or a pharmaceutically acceptable salt thereof of claim 1, wherein $R_1$, $R_3$ and $R_4$ are each $C_1$-$C_4$ alkyl, $R_2$ and $R_5$ are each independently hydrogen or $C_1$-$C_4$ alkyl, $R_6$ is hydrogen, hydroxy, $C_1$-$C_4$ alkoxy, amino, oxo(=O) or hydroxyimino(=N—OH), Ar is phenyl unsubstituted or substituted with at least one selected from the group consisting of $C_1$-$C_4$ alkyl, $C_1$-$C_4$ alkoxy, and halogen, X is a carbon atom, and $R_7$ is hydroxy, amino, $C_1$-$C_4$ alkoxy or $C_1$-$C_4$ alkylamino.

3. The dolastatin-10 derivative or a pharmaceutically acceptable salt thereof of claim 1, wherein $R_1$, $R_3$ and $R_4$ are each methyl, $R_2$ and $R_5$ are each independently hydrogen or methyl,
$R_6$ is hydrogen, hydroxy, methoxy, amino, oxo (=O) or hydroxyimino (=N—OH),
Ar is phenyl unsubstituted or substituted with at least one selected from the group consisting of methyl, methoxy and halogen,
X is a carbon atom, and
$R_7$ is hydroxy, amino, methoxy, or N-methylamino.

4. A dolastatin-10 derivative, represented by the following Chemical Formula Ia:

[Chemical Formula Ia]

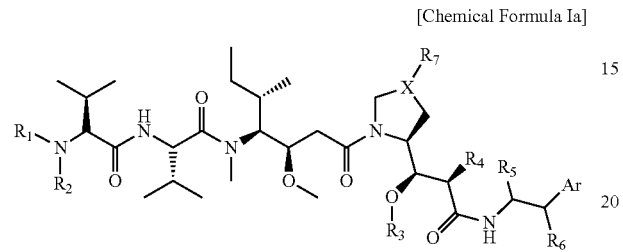

a pharmaceutically acceptable salt thereof,
wherein
$R_1$, $R_2$, $R_3$, $R_4$, and $R_5$ are each independently hydrogen or $C_1$-$C_4$ alkyl,
$R_6$ is hydrogen, hydroxy, $C_1$-$C_4$ alkoxy, amino, oxo(=O), or hydroxyimino(=N—OH),
Ar is aryl,
X is a carbon, oxygen or sulfur atom, and
$R_7$ is hydroxy, amino, $C_1$-$C_4$ alkoxy, $C_1$-$C_4$ alkylamino, or oxo (=O) when X is a carbon atom, and is absent when X is an oxygen or sulfur atom.

5. The dolastatin-10 derivative or a pharmaceutically acceptable salt thereof of claim 1, being selected from the group consisting of:
(S)—N-((3R,4S,5S)-1-((2R,4R)-2-((1R,2R)-3-((2,6-difluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-1);
(S)—N-((3R,4S,5S)-1-((2R,4R)-2-((1R,2R)-3-((3-fluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-2);
(S)—N-((3R,4S,5S)-1-((2R,4R)-2-((1R,2R)-3-((4-fluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-3);
(S)—N-((3R,4S,5 S)-1-((2R,4R)-2-((1R,2R)-3-((2,4-dichloro-5-fluorophenethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-4);
(2S)—N-((3R,4S)-3-methoxy-1-((2R,4R)-4-methoxy-2-((1R,2R)-1-methoxy-3-((2-(4-methoxyphenyl)-2-oxoethyl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-5);
(2S)—N-((3R,4S)-3-methoxy-1-((2R,4R)-4-methoxy-2-((1R,2R)-1-methoxy-2-methyl-3-oxo-3-(((R)-1-oxo-1-phenylpropan-2-yl)amino)propyl)pyrrolidin-1-yl)-5-methyl-1-oxoheptan-4-yl)-N,3-dimethyl-2-((S)-3-methyl-2-(methylamino)butaneamido)butanamide (I-6);
(2S)—N-((3R,4S)-3-methoxy-1-((2S,4R)-4-methoxy-2-((1R,2R)-1-methoxy-2-methyl-3-oxo-3-(((S)-1-oxo-1-phenylpropan-2-yl)amino)propyl)pyrrolidin-1-yl)-5-methyl-1-oxoheptan-4-yl)-N,3-dimethyl-2-((S)-3-methyl-2-(methylamino)butaneamido)butanamide (I-7);
(S)-2-((S)-2-(dimethylamino)-3-methylbutaneamido)-N-((3R,4S,5 S)-1-((2R,4R)-4-hydroxy-2-((1R,2R)-1-methoxy-2-methyl-3-oxo-3-(phenethylamino)propyl)pyrrolidin-1-yl)-3-methoxy-5-methyl-1-oxoheptan-4-yl)-N,3-dimethylbutanamide (I-8);
(S)-2-((S)-2-(dimethylamino)-3-methylbutaneamido)-N-((3R,4S,5 S)-3-methoxy-1-((R)-2-((1R,2R)-1-methoxy-2-methyl-3-oxo-3-(phenethylamino)propyl)-4-oxopyrrolidin-1-yl)-5-methyl-1-oxoheptan-4-yl)-N,3-dimethylbutanamide (I-9);
(S)-2-((S)-2-(dimethylamino)-3-methylbutaneamido)-N-((3R,4S,5 S)-3-methoxy-1-((2R,4S)-4-methoxy-2-((1R,2R)-1-methoxy-2-methyl-3-oxo-3-(phenethylamino)propyl)pyrrolidin-1-yl)-5-methyl-1-oxoheptan-4-yl)-N,3-dimethylbutanamide (I-10);
(S)—N-((3R,4S,5 S)-1-((2R,4R)-2-((1R,2R)-3-(((R)-1-(4-fluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-11);
(S)—N-((3R,4S,5 S)-1-((2R,4R)-2-((1R,2R)-3-(((S)-1-(4-fluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-12);
(S)—N-((3R,4S,5 S)-3-methoxy-1-((2R,4R)-4-methoxy-2-((1R,2R)-1-methoxy-3-(((R)-1-(2-methoxyphenyl)-1-oxopropan-2-yl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-13);
(S)—N-((3R,4S,5 S)-3-methoxy-1-((2R,4R)-4-methoxy-2-((1R,2R)-1-methoxy-3-(((R)-1-(3-methoxyphenyl)-1-oxopropan-2-yl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-14);
(S)—N-((3R,4S,5 S)-3-methoxy-1-((2R,4R)-4-methoxy-2-((1R,2R)-1-methoxy-3-(((R)-1-(4-methoxyphenyl)-1-oxopropan-2-yl)amino)-2-methyl-3-oxopropyl)pyrrolidin-1-yl)-5-methyl-1-oxoheptan-4-yl)-N,3-dimethyl-2-((S)-3-methyl-2-(methylamino)butaneamido)butanamide (I-15);
(S)—N-((3R,4S,5 S)-1-((2R,4R)-2-((1R,2R)-3-(((S)-1-(3,5-difluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-16);
(S)—N-((3R,4S,5 S)-1-((2R,4R)-2-((1R,2R)-3-(((S)-1-(2,6-difluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-17);

(S)—N-((3R,4S,5 S)-1-((2R,4R)-2-((1R,2R)-3-(((R)-1-(2,6-difluorophenyl)-1-oxopropan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-18);

(S)—N-((3R,4S,5 S)-1-((2R,4R)-2-((1R,2R)-3-(((R,Z)-1-(hydroxyimino)-1-(3-methoxyphenyl)propan-2-yl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-19);

(S)-2-((S)-2-(dimethylamino)-3-methylbutaneamido)-N-((3R,4S,5 S)-1-((2R,4R)-2-((1R,2R)-3-(((R)-1-(hydroxyimino)-1-(3-methoxyphenyl)propan-2-yl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-20);

(S)-2-((S)-2-(dimethylamino)-3-methylbutaneamido)-N-((3R,4S,5 S)-1-((2R,4R)-2-((1R,2R)-3-(((R)-1-(4-fluorophenyl)-1-(hydroxyimino)propan-2-yl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-21);

(S)—N-((3R,4S,5S)-1-((2R,4R)-2-((1R,2R)-3-((2-(5-bromo-2-methylphenyl)-2-(hydroxyimino)ethyl)amino)-1-methoxy-2-methyl-3-oxopropyl)-4-methoxypyrrolidin-1-yl)-3-methoxy-5-methyl-1-oxoheptan-4-yl)-2-((S)-2-(dimethylamino)-3-methylbutaneamido)-N,3-dimethylbutanamide (I-22);

(S)-2-((S)-2-(dimethylamino)-3-methylbutaneamido)-N-((3R,4S,5S)-1-((2R,4R)-2-((1R,2R)-3-((2-(4-fluoro-2-methylphenyl)-2-(hydroxyimino)ethyl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-23);

(S)—N-((3R,4S,5S)-1-((2R,4R)-2-((1R,2R)-3-((2-(4-fluoro-2-methylphenyl)-2-(hydroxyimino)ethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-24);

(S)—N-((3R,4S,5S)-1-((2S,4R)-2-((1R,2R)-3-(((E)-2-(2-fluoro-4-methoxyphenyl)-2-hydroxyimino)ethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-25);

(S)-2-((S)-2-(dimethylamino)-3-methylbutaneamido)-N-((3R,4S,5S)-1-((2R,4R)-2-((1R,2R)-3-((2-(4-fluoro-2-methylphenyl)-2-(oxoethyl)amino)-1-methoxy-2-methyl-3-oxopropyl)-4-methoxypyrrolidin-1-yl)-3-methoxy-5-methyl-1-oxoheptan-4-yl)-N,3-dimethylbutanamide (I-26);

(S)—N-((3R,4S,5S)-1-((2R,4R)-2-((1R,2R)-3-((2-(4-fluoro-2-methylphenyl)-2-(oxoethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-27);

(S)—N-((3R,4S,5S)-3-methoxy-1-((2S,4R)-4-methoxy-2-((1R,2R)-1-methoxy-2-methyl-3-oxo-3-((2-oxo-2-(o-tolyl)ethyl)amino)propyl)pyrrolidin-1-yl)-5-methyl-1-oxoheptan-4-yl)-N,3-dimethyl-2-((S)-3-methyl-2-(methylamino)butaneamido)butanamide (I-28);

(S)—N-((3R,4S,5S)-3-methoxy-1-((2S,4R)-4-methoxy-2-((1R,2R)-1-methoxy-2-methyl-3-oxo-3-((2-oxo-2-(p-tolyl)ethyl)amino)propyl)pyrrolidin-1-yl)-5-methyl-1-oxoheptan-4-yl)-N,3-dimethyl-2-((S)-3-methyl-2-(methylamino)butaneamido)butanamide (I-29);

(S)—N-((3R,4S,5S)-1-((2S,4R)-2-((1R,2R)-3-(2-(4-fluorophenyl)-2-oxoethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-30);

(S)—N-((3R,4S,5S)-1-((2S,4R)-2-((1R,2R)-3-(2-(2-fluoro-4-methoxyphenyl)-2-oxoethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-31);

(S)—N-((3R,4S,5S)-1-((S)-4-((1R,2R)-3-((2,6-difluorophenethyl)amino)-1-methoxy-2-methyl-3-oxopropyl)thiazolidin-3-yl)-3-methoxy-5-methyl-1-oxoheptan-4-yl)-N,3-dimethyl-2-((S)-3-methyl-2-(methylamino)butaneamido)butanamide (I-32);

(2S)—N-((3R,4S)-3-methoxy-1-((2S,4S)-4-methoxy-2-((1R,2R)-1-methoxy-2-methyl-3-oxo-3-(phenethylamino)propyl)pyrrolidin-1-yl)-5-methyl-1-oxoheptan-4-yl)-N,3-dimethyl-2-((S)-3-methyl-2-(methylamino)butaneamido)butanamide (I-33);

(2S)—N-((3R,4S)-3-methoxy-1-((2S,4R)-4-methoxy-2-((1R,2R)-1-methoxy-2-methyl-3-oxo-3-((2-oxo-2-phenylethyl)amino)propyl)pyrrolidin-1-yl)-5-methyl-1-oxoheptan-4-yl)-N,3-dimethyl-2-((S)-3-methyl-2-(methylamino)butaneamido)butanamide (I-34);

(2S)—N-((3R,4S)-1-((2S,4R)-2-((1R,2R)-3-(2-(2-hydroxy-2-phenylethyl)amino)-1-methoxy-2-methyl-3-oxopropyl)-4-methoxypyrrolidin-1-yl)-3-methoxy-5-methyl-1-oxoheptan-4-yl)-N,3-dimethyl-2-((S)-3-methyl-2-(methylamino)butaneamido)butanamide (I-35);

(2S)—N-((3R,4S)-1-((2S)-2-((1R,2R)-3-(((2R)-1-amino-1-phenylpropan-2-yl)amino)-1-methoxy-2-methyl-3-oxopropyl)-4-methoxypyrrolidin-1-yl)-3-methoxy-5-methyl-1-oxoheptan-4-yl)-2-((S)-2-(dimethylamino)-3-methylbutaneamido)-N,3-dimethylbutanamide (I-36);

(2S)—N-((3R,4S)-1-((2S,4R)-2-((1R,2R)-3-(((2S)-1-amino-1-phenylpropan-2-yl)amino)-1-methoxy-2-methyl-3-oxopropyl)-4-methoxypyrrolidin-1-yl)-3-methoxy-5-methyl-1-oxoheptan-4-yl)-2-((S)-2-(dimethylamino)-3-methylbutaneamido)-N,3-dimethylbutanamide (I-37);

(2S)—N-((3R,4S)-3-methoxy-1-((2S,4R)-4-methoxy-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N,3-dimethyl-2-((S)-3-methyl-2-(methylamino)butaneamido)butanamide (I-38);

(2S)—N-((3R,4S)-3-methoxy-1-((2S,4R)-4-methoxy-2-((1R,2R)-1-methoxy-2-methyl-3-oxo-3-((2-(thiophen-2-yl)ethyl)amino)propyl)pyrrolidin-1-yl)-5-methyl-1-oxoheptan-4-yl)-N,3-dimethyl-2-((S)-3-methyl-2-(methylamino)butaneamido)butanamide (I-39);

(2S)—N-((3R,4S)-1-((2S,4S)-2-((1R,2R)-3-((2,6-difluorophenethyl)amino)-1-methoxy-2-methyl-3-oxopropyl)-4-hydroxypyrrolidin-1-yl)-3-methoxy-5-methyl-1-oxoheptan-4-yl)-2-((S)-2-(dimethylamino)-3-methylbutaneamido)-N,3-dimethylbutanamide (I-40);

(2S)-2-((S)-2-(dimethylamino)-3-methylbutaneamido)-N-((3R,4S)-1-((2S,4S)-2-((1R,2R)-3-(((S)-1-(4-fluorophenyl)-1-oxopropan-2-yl)amino)-1-methoxy-2-methyl-3-oxopropyl)-4-hydroxypyrrolidin-1-yl)-3- methoxy-5-methyl-1-oxoheptan-4-yl)-N,3-dimethylbutanamide (I-41);

(2S)—N-((3R,4S)-1-((2S,4S)-2-((1R,2R)-3-((2,6-difluorophenethyl)amino)-1-methoxy-2-methyl-3-oxopropyl)-4-hydroxypyrrolidin-1-yl)-3-methoxy-5-methyl-1-oxoheptan-4-yl)-N,3-dimethyl-2-((S)-3-methyl-2-(methylamino)butaneamido)butanamide (I-42);

(2S)—N-((3R,4S)-1-((2S,4S)-2-(((S)-1-(4-fluorophenyl)-1-oxopropan-2-yl)amino)-1-methoxy-2-methyl-3-oxopropyl)-4-hydroxypyrrolidin-1-yl)-3-methoxy-5-methyl-1-oxoheptan-4-yl)-N,3-dimethyl-2-((S)-3-methyl-2-(methylamino)butaneamido)butanamide (I-43);

(2S)—N-((3R,4S)-1-((2S,4S)-4-amino-2-((1R,2R)-3-((2,6-difluorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutaneamido)-N,3-dimethylbutanamide (I-44); and (2S)—N-((3R,4S)-1-((2S,4S)-2-((1R,2R)-3-((2,6-difluorophenethyl)amino)-1-methoxy-2-methyl-3-oxopropyl)-4-(methylamino)pyrrolidin-1-yl)-3-methoxy-5-methyl-1-oxoheptan-4-yl)-2-((S)-2-(dimethylamino)-3-methylbutaneamido)-N,3-dimethylbutanamide (I-45).

6. A method of producing a dolastatin-10 derivative represented by the following Chemical Formula I, comprising condensing a compound represented by the following Chemical Formula II with a compound represented by the following Chemical Formula III, and deprotecting the condensate if a protecting group exists,

[Chemical Formula II]

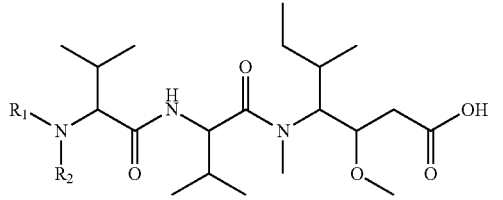

[Chemical Formula III]

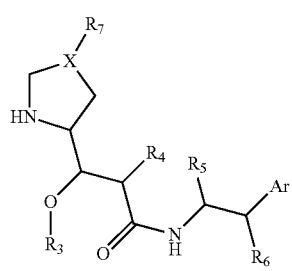

[Chemical Formula I]

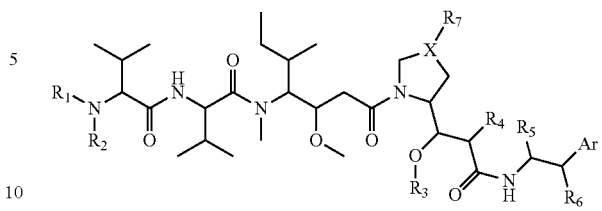

wherein, $R_1$ and $R_2$ are each independently hydrogen, $C_1$-$C_4$ alkyl, or an amino protecting group, $R_3$, $R_4$ and $R_5$ are each independently hydrogen or $C_1$-$C_4$ alkyl, $R_6$ is hydrogen, protected or unprotected hydroxy, $C_1$-$C_4$ alkoxy, protected or unprotected amino, oxo (=O), or hydroxyimino (=N—OH), Ar is aryl, X is a carbon, oxygen or sulfur atom, and $R_7$ is protected or unprotected hydroxy, protected or unprotected amino, $C_1$-$C_4$ alkoxy, protected or unprotected $C_1$-$C_4$ alkylamino, or oxo (=O) when X is a carbon atom, and is absent when X is an oxygen or sulfur atom.

7. The method of claim 6, wherein the amino protecting group is t-butoxycarbonyl (t-Boc), carbobenzyloxy (Cbz), 9-fluorenylmethoxycarbonyl (Fmoc) or benzyl (Bn).

8. The method of claim 6, wherein the hydroxy protecting group is t-butyldimethylsilyl.

9. The method of claim 6, wherein the compound of Chemical Formula III is in a form of hydrochloride or trifluoroacetate (TFA).

10. The method of claim 6, wherein the condensation reaction is carried out in presence of a coupling agent selected from the group consisting of dicyclohexylcarbodiimide (DCC), diphenylphosphorylazide (DPPA), diethyl cyanophosphonate (DEPC) and benzotriazol-1-yl-oxy-tris(dimethylamino)phosphoniumhexafluorophosphate (BOP reagent), and an organic base selected from the group consisting of triethylamine and diisopropylethylamine (DIPEA).

11. The method of claim 6, wherein the deprotecting reaction of the amino protecting group is carried out using 10% palladium carbon or 20% palladium hydroxide.

12. The method of claim 6, wherein the deprotecting reaction of the hydroxy amino protecting group is carried out using tetrabutylammonium fluoride.

13. A method of treating cancer, wherein the cancer is breast cancer, human epithelial cancer, non-small cell lung cancer, or colon cancer, comprising the administration of a therapeutically effective amount of the dolastatin-10 derivative of claim 1 or a pharmaceutically acceptable salt thereof, and a pharmaceutically acceptable carrier, to a mammal in need of treatment.

14. The method of treating cancer of claim 13, wherein the cancer is breast cancer.

* * * * *